(12) United States Patent
Knipp et al.

(10) Patent No.: US 9,849,193 B2
(45) Date of Patent: Dec. 26, 2017

(54) NANOPARTICLES FOR DRUG DELIVERY

(71) Applicants: University of Louisville Research Foundation, Inc., Louisville, KY (US); Ralph J. Knipp, Louisville, KY (US); Michael H. Nantz, Louisville, KY (US)

(72) Inventors: Ralph J. Knipp, Louisville, KY (US); Michael H. Nantz, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/766,726

(22) PCT Filed: Feb. 7, 2014

(86) PCT No.: PCT/US2014/015413
§ 371 (c)(1),
(2) Date: Aug. 7, 2015

(87) PCT Pub. No.: WO2014/124329
PCT Pub. Date: Aug. 14, 2014

(65) Prior Publication Data
US 2015/0374849 A1    Dec. 31, 2015

Related U.S. Application Data

(60) Provisional application No. 61/762,832, filed on Feb. 8, 2013, provisional application No. 61/773,663, filed on Mar. 6, 2013.

(51) Int. Cl.
*A61K 47/48*    (2006.01)
*A61K 9/14*     (2006.01)
*A61K 41/00*    (2006.01)

(52) U.S. Cl.
CPC .... *A61K 47/48884* (2013.01); *A61K 41/0028* (2013.01); *A61K 47/48015* (2013.01); *A61K 47/48023* (2013.01); *A61K 47/48861* (2013.01)

(58) Field of Classification Search
None
See application file for complete search history.

(56) References Cited

U.S. PATENT DOCUMENTS

| 2010/0166665 | A1* | 7/2010 | Butts | A61K 49/0428 424/9.32 |
|---|---|---|---|---|
| 2011/0223255 | A1 | 9/2011 | Thiesen et al. | |
| 2012/0003155 | A1 | 1/2012 | Kannan et al. | |
| 2012/0135530 | A1 | 5/2012 | Bamdad et al. | |
| 2012/0309691 | A1 | 12/2012 | Zhou et al. | |

FOREIGN PATENT DOCUMENTS

| WO | 2005110407 | | 11/2005 |
|---|---|---|---|
| WO | 2006108405 | | 10/2006 |
| WO | 2006125736 | A1 | 11/2006 |
| WO | 2009100716 | A2 | 8/2009 |
| WO | 2011049972 | A1 | 4/2011 |
| WO | 2012082382 | | 6/2012 |

OTHER PUBLICATIONS

Lee et al., Bioconjugate Chem., 2006, 17, 1364-1368.*
Gangopadhyay et al., IEEE Transactions on Magnetics, 2005, 41(10), 4194-4196.*
Prabaharan et al., Biomaterials, 2009, 30, 6065-6075.*
Chen et al., Nanotechnology, 2008, 19, 165103 (9 pages).*
Aryal, et al., "Doxorubicin conjugated gold nanoparticles as water-soluble and pH-responsive anticancer drug nanocarriers", J Mater Chem 19, 7879-7884 (2009).
Bulte, et al., "Iron oxide MR contrast agents for molecular and cellular imaging", NMR Biomed 17(7), 484-499 (2004).
Carrey, et al., "Simple models for dynamic hysteresis loop calculations of magnetic single-domain nanoparticles: Application to magnetic hyperthermia optimization", J Appl Phys 109, 083921 (2011).
Choi, et al., "A photochemical approach for controlled drug release in targeted drug delivery", Bioorg Med Chem 20 (3), 1281-1290 (2012).
Choubey, et al., "Investigation on magnetically controlled delivery of doxorubicin from superparamagnetic nanocarriers of gelatin crosslinked with genipin", J Mater Sci: Mater Med 21, 1573-1586 (2010).
El-Gamel, et al., "SiO2@Fe2(3 core-shell nanoparticles for covalent immobilization and release of sparfloxacin drug", Chem Commun 47, 10076-10078 (2011).
Kievit, et al., "Surface engineering of iron oxide nanoparticles for targeted cancer therapy", Acc Chem Res 44 (10), 853-862 (2011).
Kim, et al., "Designed Fabrication of a Multifunctional Polymer Nanomedical Platform for Simultaneous Cancer-Targeted Imaging and Magnetically Guided Drug Delivery", Advanced Materials vol. 20 (3), 478-483 (2008).
Knipp, et al., "Magnetic Field-Induced Cyclizations of Amino-Esters and -Carbonates Bound to Iron Oxide Nanoparticles", Paper 212, presented at Nanotech 2013, Washington, D. C.; May 12-16, 2013.
Knipp, et al., "Thermally induced substrate release via intramolecular cyclizations of Amino esters and Amino carbonates", Tetrahedron 70, 3422-3429 (2014).
Lee, et al., "Uniform mesoporous dye-doped silica nanoparticles decorated with multiple magnetite nanocrystals for simultaneous enhanced magnetic resonance imaging, fluorescence imaging, and drug delivery", J Am Chem Soc 132 (2), 552-557 (2010).

(Continued)

*Primary Examiner* — Abigail Vanhorn
(74) *Attorney, Agent, or Firm* — Viksnins Harris Padys Malen LLP

(57) ABSTRACT

The invention provides nanoparticles, methods for making nanoparticles, and methods for using nanoparticles. An important attribute of a drug delivery system is its ability to allow for spatial and temporal regulated drug release, thereby minimizing side effects and improving therapeutic efficacy of conventional pharmaceuticals. Iron oxide nanoparticles (NPs), specifically Fe3O4 nanoparticles, possess many appropriate qualities that make them a viable choice for drug delivery.

23 Claims, 16 Drawing Sheets

(56) References Cited

OTHER PUBLICATIONS

Liu, et al., "Instantaneous drug delivery of magnetic/thermally sensitive nanospheres by a high-frequency magnetic field", Langmuir 24 (23), 13306-13311 (2008).
Liu, et al., "Magnetically Sensitive Alginate-Templated Polyelectrolyte Multilayer Microcapsules for Controlled Release of Doxorubicin", Journal of Physical Chemistry C vol. 114 (17), 7673-7679 (2010).
Meng, et al., "Engineered design of mesoporous silica nanoparticles to deliver doxorubicin and P-glycoprotein siRNA to overcome drug resistance in a cancer cell line", ACS Nano 4 (8), 4539-4550 (2010).
Meng, et al., "Iron oxide-based nanomagnets in nanomedicine: fabrication and applications", Nano Reviews 1, 4883, 17 pages (2010).
Patent Cooperation Treaty, International Searching Authority, Search Report and Written Opinion for PCT/US2014/015413, 10 pages, May 12, 2014.
Rahimi, et al., "In vitro evaluation of novel polymer-coated magnetic nanoparticles for controlled drug delivery", Nanomedicine 6 (5), 672-680 (2010).
Yang, et al., "Fe3O4 nanostructures: synthesis, growth mechanism, properties and applications", Chem Commun (Camb.) 47(18), 51305141 (2011).
Yu, et al., "Drug-loaded superparamagnetic iron oxide nanoparticles for combined cancer imaging and therapy in vivo", Angew Chem Int Ed Engl 47 (29), 5362-5365 (2008).
Zhang, et al., "Folate-decorated poly(lactide-co-glycolide)-vitamin E TPGS nanoparticles for targeted drug delivery", Biomaterials 28 (10), 1889-1899 (2007).
Zhang, et al., "Uptake of folate-conjugated albumin nanoparticles to the SKOV3 cells", Int J Pharm 287 (1-2), 155-162 (2004).

* cited by examiner

NANOPARTICLES FOR DRUG DELIVERY

CROSS REFERENCE TO RELATED APPLICATIONS

This patent application claims the benefit of priority of U.S. application Ser. No. 61/762,832 filed Feb. 8, 2013 and U.S. application Ser. No. 61/773,663 filed Mar. 6, 2013, which applications are hereby incorporated by reference.

BACKGROUND

An important attribute of a drug delivery system is its ability to allow for spatial and temporal regulated drug release, thereby minimizing side effects and improving therapeutic efficacy of conventional pharmaceuticals. Iron oxide nanoparticles (NPs), specifically $Fe_3O_4$ nanoparticles, possess many appropriate qualities that make them a viable choice for drug delivery. $Fe_3O_4$ NPs are biocompatible (Kievit, F. M., et al., *Accounts of Chemical Research* 2011, 44 (10), 853-862), have low cytotoxicity (Bulte, J. W. M., et al., *NMR in Biomedicine* 2004, 17, 484-499), and provide multiple means for surface modification. Though these attributes are needed in a drug delivery vehicle, there are multiple different NPs that possess similar qualities including gold and silica. $Fe_3O_4$ is set apart from these NPs due to its paramagnetic or superparamagnetic (SPM) qualities (Yang, C., et al., *Chemical Communications* 2011, 47, 5130-5141). The SPM properties of $Fe_3O_4$ NPs have been used for a variety of applications. A basic utilization of SPM capability is to induce non-invasive hyperthermia within cancer cells. Alternating electromagnetic field (AMF)-induced $Fe_3O_4$ NPs heat body tissue to temperatures as high as 45° C., and this causes cell death. In addition, when functionalized either by ionic interactions or through entrapment via a polymer gel coating, drugs can be guided to tumor regions through the use of a magnet, as first demonstrated by Meyers in 1963 (Meyers, P. H., et al., *American Journal of Roentgenology, Radium Therapy, and Nuclear Medicine* 1963, 90, 1068-1077). Through more advanced methods, $Fe_3O_4$ NPs are now extensively functionalized with complex delivery mechanisms and can be directed by taking advantage of tumor folate receptors (Kim, J., et al., *Advanced Materials* 2008, 20, 478-483, Zhang, Z., et al., *Biomaterials* 2007, 28 (10), 1889-1899, Zhang, L., et al., *International Journal of Pharmaceutics* 2004, 287 (1-2), 155-162). Finally, iron oxide also can be used as a magnetic resonance imaging contrast agent, so delivery systems based on this material can be visualized (Lee, J. E.; et al., *Journal of the American Chemical Society* 2010, 132, 552-557).

Some of the most common methods of functionalization or attachment of drug payloads to $Fe_3O_4$ NPs involve the use of ionic attraction (Nantz, M. H., et al., PCT Int. Appl. 2011, WO 2011049972 A1 20110428), the addition of a mesoporous silica shell around the $Fe_3O_4$ NPs followed by further functionalization of the silica (Meng, H., et al., A. E., *ACS Nano* 2010, 4 (8), 4539-4550, Lin, Meng M., et al., *Nano Reviews* 2010, 1, 4883) or the use of a polymer coating around the $Fe_3O_4$ NPs (Yu, M. K., et al., *Angewandte Chemie International Edition* 2008, 47 (29), 5362-5365, Rahimi, M., et al., *Nanomedicine: Nanotechnology, Biology, and Medicine* 2010, 6, 672-680). Once the NPs reach target (e.g., cancerous) tissue, a release mechanism is initiated so that the drug payloads are available only to the target tissue. One of the most common release methods involves use of a pH sensitive trigger, such as when using a hydrazone linkage (Aryal, S., et al., *Journal of Materials Chemistry* 2009, 19, 7879-7884). For example, when the loaded NP enters into a tumor, the reduced pH of the tumor can hydrolyze the hydrazone linkage to unmask the drug (a carbonyl-based drug). Another method of release is photochemical. By adding a photolabile group into a linker, usually an aromatic ring with a nitro-group ortho to a leaving group, the drug can be released upon exposure to a specific wavelength of light (Choi, S. K., et al., *Bioorganic & Medicinal Chemistry* 2012, 20, 1281-1290).

Another method to release the drug involves the use of an alternating electromagnetic field (AMF). An AMF, similar to an AC current, switches the poles of the magnetic current at a quick pace, and this causes resident iron oxide NPs to heat as they struggle to stay aligned with the applied magnetic field (Carrey, J., et al., *Journal of Applied Physics* 2011, 109, 083921). AMF-mediated drug delivery has a distinct advantage over the pH sensitive linker approach in that drug release relies on a controllable external stimulus whereas the acid labile linker requires a stimulus within the patient that cannot be easily controlled. If the tumor is not sufficiently acidic, then the linker-bound drug will not be released. In the same way, if certain healthy cells happen to be overly acidic, then the drug is released and can exert its pharmacological effect on healthy cells. In contrast, AMF exposure allows for the controlled release in a specific region and at a specific time without the need for precise, and often unpredictable, internal conditions. Thus AMF-mediated delivery systems offer the advantages of spatial and temporal control.

Despite the advantages in controlled release using an AMF trigger, many present NP drug delivery systems have a problem of premature drug release (i.e., leakage). In these instances, drugs are slowly released prior to application of the external stimulus. This is largely due to the inability of the drugs in these delivery systems to be covalently retained until the stimulus is applied. For example, AMF-induced NP heating commonly is used to reduce ionic interactions and/or hydrogen bonding interactions (Biswas, S. Functionalized Nanoparticles for AMF-Induced Gene and Drug Delivery. University of Louisville, Louisville, Ky., 2011), or to cause a polymer shell to squeeze out the drug payload (Liu, T.-Y., et al., *Langmuir* 2008, 24, 13306-13311) or to expand and allow the drug payload to diffuse away (Liu, J., et al., *Journal of Physical Chemistry C* 2010, 114, 7673-7679). In these cases, the ambient heat or biological milieu of a living system can reduce the ionic/hydrogen bonding interactions between NP and drug, or cause polymer contractions or expansions. Premature drug release occurs since the drug is not covalently attached to the NP carrier.

Thus, there is a need for a drug delivery system with reduced premature release of its drug payload and that can optionally target the drug spatially, temporally, or both spatially and temporally.

SUMMARY OF CERTAIN EMBODIMENTS

Accordingly, certain embodiments provide a therapeutic magnetic nanoparticle, or a salt thereof, comprising a magnetic nanoparticle covalently bonded to one or more -L-D groups wherein D is a residue of a therapeutic agent (e.g., a residue of a therapeutic agent, a residue of a prodrug of a therapeutic agent or a residue of a functional group derivative of a therapeutic agent) and L is a linker capable of undergoing an intramolecular cyclization.

In certain embodiments the linker capable of undergoing an intramolecular cyclization is suitable to release the therapeutic agent from the linker upon intramolecular cyclization.

In certain embodiments the linker capable of undergoing an intramolecular cyclization that is suitable to release the therapeutic agent from the linker can form a 3-8 membered heterocycle upon intramolecular cyclization.

In certain embodiments the linker capable of undergoing an intramolecular cyclization that is suitable to release the therapeutic agent from the linker forms a 3-8 membered heterocycle upon intramolecular cyclization.

In certain embodiments the linker capable of undergoing an intramolecular cyclization that is suitable to release the therapeutic agent from the linker can form a 3-8 membered heterocycle upon intramolecular cyclization, wherein the 3-8 membered heterocycle has a functional group within the ring selected from an amide, carbamate, urea, carbamothioate, thioamide, thiocarbamate, thiourea and carbamodithioate.

In certain embodiments the linker capable of undergoing an intramolecular cyclization that is suitable to release the therapeutic agent from the linker forms a 4-8 membered heterocycle upon intramolecular cyclization, wherein the 4-8 heterocycle has a functional group within the ring selected from an amide, carbamate, urea, carbamothioate, thioamide, thiocarbamate, thiourea and carbamodithioate.

In certain embodiments the linker capable of undergoing an intramolecular cyclization that is suitable to release the therapeutic agent from the linker forms a 5-8 membered heterocycle upon intramolecular cyclization, wherein the 5-8 membered heterocycle has a functional group within the ring selected from an amide, carbamate, urea, carbamothioate, thioamide, thiocarbamate, thiourea and carbamodithioate.

In certain embodiments the linker capable of undergoing an intramolecular cyclization that is suitable to release the therapeutic agent from the linker forms a 5-7 membered heterocycle upon intramolecular cyclization, wherein the 5-7 membered heterocycle has a functional group within the ring selected from an amide, carbamate, urea, carbamothioate, thioamide, thiocarbamate, thiourea and carbamodithioate.

In certain embodiments the linker capable of undergoing an intramolecular cyclization that is suitable to release the therapeutic agent from the linker forms a 3-8 membered heterocycle upon intramolecular cyclization, wherein the 3-8 membered heterocycle has an amide or carbamate functional group within the ring.

In certain embodiments the linker capable of undergoing an intramolecular cyclization that is suitable to release the therapeutic agent from the linker forms a 4-8 membered heterocycle upon intramolecular cyclization, wherein the 4-8 membered heterocycle has an amide or carbamate functional group within the ring.

In certain embodiments the linker capable of undergoing an intramolecular cyclization that is suitable to release the therapeutic agent from the linker forms a 5-8 membered heterocycle upon intramolecular cyclization, wherein the 5-8 membered heterocycle has an amide or carbamate functional group within the ring.

In certain embodiments the linker capable of undergoing an intramolecular cyclization that is suitable to release the therapeutic agent from the linker forms a 5-7 membered heterocycle upon intramolecular cyclization, wherein the 5-7 membered heterocycle has an amide or carbamate functional group within the ring.

It is to be understood that the 3-8, 4-8, 5-8 and 5-7 membered heterocycles discussed herein above may be substituted depending on the linker from which they are formed.

In certain embodiments the magnetic nanoparticle further comprises a coating.

In certain embodiments the magnetic nanoparticle further comprises a gold coating.

In certain embodiments the magnetic nanoparticle further comprises a silica coating.

In certain embodiments a magnetic nanoparticle is an iron oxide nanoparticle or a coated iron oxide nanoparticle.

In certain embodiments a magnetic nanoparticle comprises iron.

In certain embodiments a magnetic nanoparticle is an iron alloy.

In certain embodiments a magnetic nanoparticle comprises iron oxide.

In certain embodiments a magnetic nanoparticle is an iron oxide alloy.

In certain embodiments a magnetic nanoparticle is a coated iron oxide nanoparticle.

In certain embodiments a magnetic nanoparticle is an iron oxide nanoparticle.

In certain embodiments a coated iron oxide nanoparticle is an iron oxide nanoparticle coated with silica.

In certain embodiments a coated iron oxide nanoparticle is an iron oxide nanoparticle coated with gold.

In certain embodiments the magnetic nanoparticle is an iron oxide nanoparticle coated with silica.

In certain embodiments the magnetic nanoparticle is an iron oxide nanoparticle coated with gold.

Certain embodiments provide a linker capable of undergoing an intramolecular cyclization wherein the intramolecular cyclization can be induced by heating the magnetic nanoparticle.

Certain embodiments provide a linker capable of undergoing an intramolecular cyclization wherein the intramolecular cyclization can be induced by application of an alternating electromagnetic field to the magnetic nanoparticle.

Certain embodiments provide a therapeutic magnetic nanoparticle, or a salt thereof comprising a magnetic nanoparticle covalently bonded to one or more -L-D groups wherein -L-D is a compound of formula I:

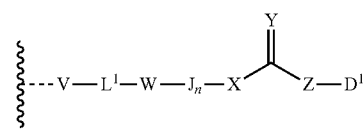

I wherein

V is $-OSi(G)_2-$, and the dashed line represents a covalent bond between the oxygen atom of $-OSi(G)_2-$ and the magnetic nanoparticle; or V is $-S-$, and the dashed line represents a covalent bond between $-S-$ and the magnetic nanoparticle;

$L^1$ is $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene, wherein $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene are optionally substituted with one or more halogen;

each J is $C(R^b)_2$ wherein one $C(R^b)_2$ of J may be replaced by $-O-$ $-S-$ or $-N(R^e)-$;

(a) W is NH, X is $CR^cR^d$, and n is an integer from 0-5; or (b) W is NH, X is O, $NR^e$ or S, and n is an integer from 1-5; or (c) W is

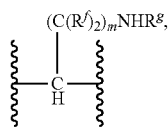

X is $CR^cR^d$, O, $NR^e$, S or absent, m is an integer from 0-5 and n is an integer from 0-5, wherein the sum of m and n is 0-5;

Y is O or S;

$Z-D^1$ is a residue of a therapeutic agent wherein Z is O, $NR^h$ or S;

each G is independently —$OR^{a1}$, —$OR^{a2}$ or $(C_1-C_6)$alkyl;

$R^{a1}$ is a covalent bond between the oxygen atom of —$OR^{a1}$ and the iron oxide nanoparticle optionally coated in silica;

each $R^{a2}$ is independently H or $(C_1-C_6)$alkyl; or two —$OR^{a2}$ groups of two adjacent L-D groups together form —O—;

each $R^b$ is independently selected from H and $(C_1-C_3)$alkyl; or two $R^b$ groups together with the carbon to which they are attached form a $(C_3-C_7)$carbocycle;

each $R^c$ is independently selected from H and $(C_1-C_6)$alkyl, and each $R^d$ is independently selected from H and $(C_1-C_6)$alkyl; or an $R^c$ group and an $R^d$ group together with the carbon to which they are attached form a $(C_3-C_7)$carbocycle;

each $R^e$ is independently selected from H and $(C_1-C_6)$alkyl;

each $R^f$ is independently selected from H and $(C_1-C_6)$alkyl; or two $R_f$ groups together with the carbon to which they are attached form a $(C_3-C_7)$carbocycle;

$R^g$ is selected from H and $(C_1-C_6)$alkyl; and $R^h$ is selected from H and $(C_1-C_6)$alkyl.

In certain embodiments the therapeutic nanoparticle further comprises a targeting element.

One embodiment provides a pharmaceutical composition comprising a therapeutic magnetic nanoparticle or a pharmaceutically acceptable salt thereof (e.g., a magnetic nanoparticle covalently bonded to one or more -L-D groups or a pharmaceutically acceptable salt thereof as described herein) and a pharmaceutically acceptable carrier.

One embodiment provides a method for administering a therapeutic agent to an animal (e.g., a mammal) comprising administering a therapeutic magnetic nanoparticle or a pharmaceutically acceptable salt thereof (e.g., a magnetic nanoparticle covalently bonded to one or more -L-D groups, or a pharmaceutically acceptable salt thereof as described herein), to the animal.

One embodiment provides a method for treating cancer, a bacterial infection, a fungal infection, a parasitic infection or an antiviral infection in an animal (e.g., a mammal) in need thereof that has been administered an effective amount of a therapeutic magnetic nanoparticle or a pharmaceutically acceptable salt thereof (e.g., a magnetic nanoparticle covalently bonded to one or more -L-D groups, or a pharmaceutically acceptable salt thereof as described herein), comprising providing conditions to release the therapeutic agent from the therapeutic magnetic nanoparticle.

One embodiment provides a method for treating cancer, a bacterial infection, a fungal infection, a parasitic infection or an antiviral infection in an animal (e.g., a mammal such as a human) comprising treating the animal with a therapeutic magnetic nanoparticle or a pharmaceutically acceptable salt thereof (e.g., a magnetic nanoparticle covalently bonded to one or more -L-D groups, or a pharmaceutically acceptable salt thereof as described herein), to the animal.

One embodiment provides a method for treating cancer, a bacterial infection, a fungal infection, a parasitic infection or an antiviral infection in an animal (e.g., a mammal such as a human) in need thereof, comprising treating the animal with an effective amount of a therapeutic magnetic nanoparticle or a pharmaceutically acceptable salt thereof (e.g., a magnetic nanoparticle covalently bonded to one or more -L-D groups, or a pharmaceutically acceptable salt thereof as described herein), to the animal.

Certain embodiments provide magnetically targeting the therapeutic magnetic nanoparticle to a specific location in the animal (e.g., a mammal such as a human).

Certain embodiments provide delivering a source of heat to the therapeutic magnetic nanoparticle to induce cyclization of the linker thereby releasing the therapeutic agent from the therapeutic magnetic nanoparticle.

Certain embodiments provide applying an alternating electromagnetic field to the therapeutic magnetic nanoparticle to induce cyclization of the linker thereby releasing the therapeutic agent from the therapeutic nanoparticle (e.g., a mammal).

Certain embodiments provide for further treating the animal (e.g., a mammal) with one or more additional therapeutic agents.

In certain embodiments the additional therapeutic agent is iron oxide nanoparticle.

One embodiment provides a therapeutic magnetic nanoparticle or a pharmaceutically acceptable salt thereof (e.g., a magnetic nanoparticle covalently bonded to one or more -L-D groups, or a pharmaceutically acceptable salt thereof as described herein), for use in medical therapy.

One embodiment provides the use of a therapeutic magnetic or a pharmaceutically acceptable salt thereof (e.g., a magnetic nanoparticle covalently bonded to one or more -L-D groups, or a pharmaceutically acceptable salt thereof as described herein), to prepare a medicament for treating cancer, a bacterial infection, a fungal infection, a parasitic infection or an antiviral infection in an animal (e.g., a mammal such as a human).

One embodiment provides a therapeutic magnetic nanoparticle or a pharmaceutically acceptable salt thereof (e.g., a magnetic nanoparticle covalently bonded to one or more -L-D groups, or a pharmaceutically acceptable salt thereof as described herein), for the therapeutic or prophylactic treatment of cancer, a bacterial infection, a fungal infection, a parasitic infection or an antiviral infection.

One embodiment provides a method for preparing a therapeutic magnetic nanoparticle, or a salt thereof comprising contacting a compound of formula II:

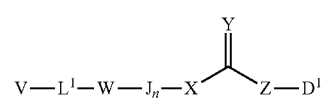

II with a magnetic nanoparticle to prepare the therapeutic nanoparticle;

wherein:

V is —$Si(OR^a)_3$ or —SH;

$L^1$ is $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene, wherein $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene is optionally substituted with one or more halogen;

each J is $C(R^b)_2$ wherein one $C(R^b)_2$ of J may be replaced by —O— —S— or —N($R^e$)—;
(a) W is NH, X is $CR^cR^d$, and n is an integer from 0-5; or
(b) W is NH, X is O, $NR^e$ or S, and n is an integer from 1-5; or
(c) W is

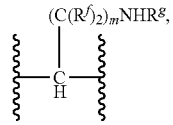

X is $CR^cR^d$, O, $NR^e$, S or absent, m is an integer from 0-5 and n is an integer from 0-5, wherein the sum of m and n is 0-5;
Y is O or S;
Z-$D^1$ is a residue of a therapeutic agent wherein Z is O, $NR^h$ or S;
$R^a$ is $(C_1-C_6)$alkyl;
each $R^b$ is independently selected from H and $(C_1-C_3)$alkyl; or two $R^b$ groups together with the carbon to which they are attached form a $(C_3-C_7)$carbocycle;
each $R^c$ is independently selected from H and $(C_1-C_6)$alkyl, and each $R^d$ is independently selected from H and $(C_1-C_6)$alkyl; or an $R^c$ group and an $R^d$ group together with the carbon to which they are attached form a $(C_3-C_7)$carbocycle;
each $R^e$ is independently selected from H and $(C_1-C_6)$alkyl;
each $R^f$ is independently selected from H and $(C_1-C_6)$alkyl; or two $R_f$ groups together with the carbon to which they are attached form a $(C_3-C_7)$carbocycle;
$R^g$ is selected from H and $(C_1-C_6)$alkyl; and
$R^h$ is selected from H and $(C_1-C_6)$alkyl.

One embodiment provides a therapeutic magnetic nanoparticle or a salt thereof, prepared by contacting a compound of formula II:

$$V-L^1-W-J_n-X\overset{Y}{\underset{}{\diagup\hspace{-0.5em}\diagdown}}Z-D^1$$ II with a magnetic nanoparticle to prepare the therapeutic nanoparticle;
wherein:
V is —Si(O$R^a$)$_3$ or —SH;
$L^1$ is $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene, wherein $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene is optionally substituted with one or more halogen;
each J is $C(R^b)_2$ wherein one $C(R^b)_2$ of J may be replaced by —O— —S— or —N($R^e$)—;
(a) W is NH, X is $CR^cR^d$, and n is an integer from 0-5; or
(b) W is NH, X is O, $NR^e$ or S, and n is an integer from 1-5; or (c) W is

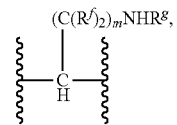

X is $CR^cR^d$, O, $NR^e$, S or absent, m is an integer from 0-5 and n is an integer from 0-5, wherein the sum of m and n is 0-5;
Y is O or S;
Z-$D^1$ is a residue of a therapeutic agent wherein Z is O, $NR^h$ or S;
$R^a$ is $(C_1-C_6)$alkyl;
each $R^b$ is independently selected from H and $(C_1-C_3)$alkyl; or two $R^b$ groups together with the carbon to which they are attached form a $(C_3-C_7)$carbocycle;
each $R^c$ is independently selected from H and $(C_1-C_6)$alkyl, and each $R^d$ is independently selected from H and $(C_1-C_6)$alkyl; or an $R^c$ group and an $R^d$ group together with the carbon to which they are attached form a $(C_3-C_7)$carbocycle;
each $R^e$ is independently selected from H and $(C_1-C_6)$alkyl;
each $R^f$ is independently selected from H and $(C_1-C_6)$alkyl; or two $R_f$ groups together with the carbon to which they are attached form a $(C_3-C_7)$carbocycle;
$R^g$ is selected from H and $(C_1-C_6)$alkyl; and
$R^h$ is selected from H and $(C_1-C_6)$alkyl.

BRIEF DESCRIPTION OF THE FIGURES

FIG. 16 illustrates a coated magnetic nanoparticle.

DETAILED DESCRIPTION

Figure 1:
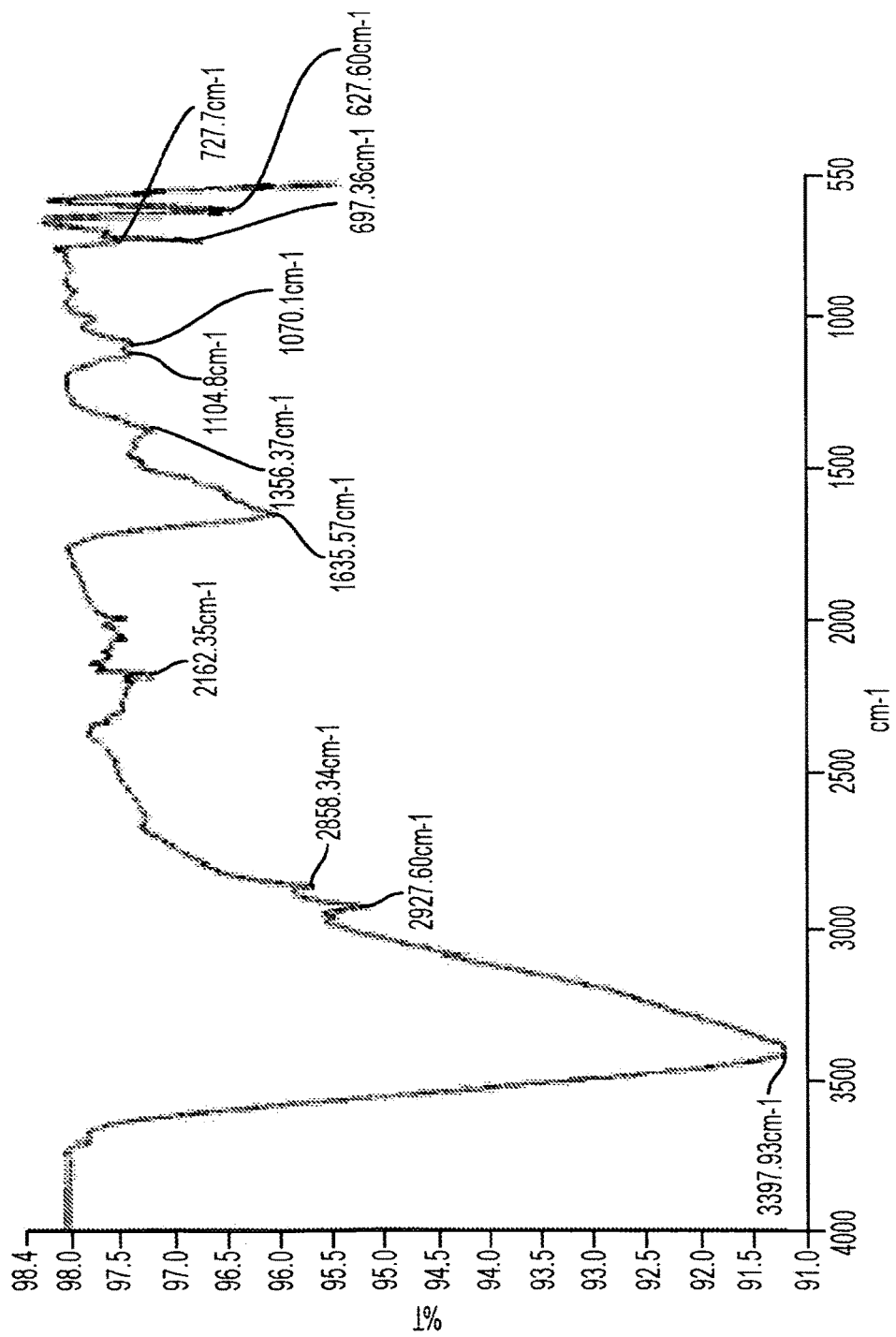
FIG. 1 illustrates the IR spectrum of $Fe_3O_4$ NPs (20-30 nm diameter).

Described herein, is a therapeutic magnetic nanoparticle drug delivery system that is designed to reduce the problem of payload leakage. Magnetic nanoparticles can be covalently attached to a molecular linker wherein the linker is also covalently bound to a therapeutic agent (e.g., drug) such as through an ester, carbonate or carbamate functional group. By placing a reactive moiety such as an amine moiety within the linker at a specified distance from the ester, carbonate or carbamate carbonyl group, the linker can undergo an intramolecular cyclization that causes release of the bound therapeutic agent. In one embodiment the heat generated by the magnetic nanoparticle on AMF exposure induces the intramolecular cyclization. This release mechanism provides a platform for the purposes of drug delivery with both spatial and temporal control.

It is possible to target the therapeutic magnetic nanoparticles to a specific location in a patient's body, e.g., by magnetically guiding the nanoparticles to the target tissue and/or by conjugating appropriate targeting elements (e.g., an antibody fragment, a small molecule ligand of a cellular receptor) to therapeutic nanoparticle.

In certain embodiments, the nanoparticles can be magnetically guided to the desired location in the body of the patient. This delivery system provides a method for delivering therapeutic agents including agents that are toxic when administered systemically by allowing for targeting of the drug to a specific location. Thus, this system is particularly useful for delivering drugs that are beneficially delivered to a specific location at a high concentration, e.g., anticancer, antibiotic, antifungal, antiparasitic, and antiviral drugs. An advantage of this delivery system is the delivery of a therapeutic agent to a specific location and the release of the therapeutic agent at a specific time through the selective heating of the magnetic nanoparticle by exposure to an AMF.

The following definitions are used, unless otherwise described.

Magnetic Nanoparticle.

Magnetic nanoparticles include any nanoparticles that possess paramagnetic or superparamagnetic (SPM) properties such as those paramagnetic or SPM properties of nanoparticles that comprise iron (iron nanoparticles) which for example include nanoparticles that comprise iron oxide (e.g., iron oxide nanoparticles). The desirable paramagnetic or superparamagnetic (SPM) properties include properties that make the magnetic nanoparticle responsive to a magnetic field (e.g., the magnetic nanoparticles will heat when exposed to an AMF). Thus, magnetic nanoparticles include iron nanoparticles such as nanoparticles comprising iron oxide (e.g., $Fe_3O_4$, the partially oxidized preparations $Fe_2O_3/Fe_3O_4$ or the fully oxidized $Fe_2O_3$). Magnetic nanoparticles also include metal alloys that possess the desired paramagnetic or superparamagnetic (SPM) properties such as those paramagnetic and SPM properties of iron nanoparticles (e.g., iron oxide nanoparticles). Accordingly the term "magnetic nanoparticle" includes nanoparticle alloys, that possess magnetic properties such as but not limited to alloys of iron oxide (for a discussion on magnetic nanoparticle alloys see: Tang, Q., et al., Using Thermal Energy Produced by Irradiation of Mn—Zn Ferrite magnetic Nanoparticles (MZF-NPs) for Heat-Inducible Gene Expression. *Biomaterials* 2008, 29, 2673-2679 which reference is incorporated herein in its entirety). It is to be understood that the amount of magnetic material (such as iron) in a magnetic nanoparticle can vary as long as the nanoparticle possesses the desired magnetic properties. Magnetic nanoparticles also include magnetic nanoparticles that are coated (e.g., coated magnetic nanoparticles) by another substance or material such as but not limited to gold, graphene or silica. As used herein the term "coated magnetic nanoparticle" includes magnetic nanoparticles wherein the surface of the magnetic nanoparticle is coated (e.g., fully or partially) by the substance or material. It is to be understood the surface of the coated magnetic nanoparticle may be fully coated or partially coated and that when the coated magnetic nanoparticle is partially coated the coating may or may not be contiguous and the coating may be of any shape (e.g., spotted). In one embodiment the surface is at least 1%, at least 10%, at least 20%, at least 40%, at least 60%, at least 80%, at least 90% or completely covered by the substance or material. In one embodiment the core of a coated magnetic nanoparticle is magnetic but the coating may not be magnetic. In one embodiment the magnetic nanoparticle is coated with two or more different coatings. The size of the magnetic nanoparticle can vary. In one embodiment the size of the magnetic nanoparticle is about 1-750 nM in diameter. In one embodiment the size of the magnetic nanoparticle is about 1-500 nM in diameter. In one embodiment the size of the magnetic nanoparticle is about 1-250 nM in diameter. In one embodiment the size of the magnetic nanoparticle is about 1-150 nM in diameter. In one embodiment the size of the magnetic nanoparticle is about 1-50 nM in diameter. In one embodiment the size of the magnetic nanoparticle is about 5-750 nM in diameter. In one embodiment the size of the magnetic nanoparticle is about 5-500 nM in diameter. In one embodiment the size of the magnetic nanoparticle is about 5-250 nM in diameter. In one embodiment the size of the magnetic nanoparticle is about 5-150 nM in diameter. In one embodiment the size of the magnetic nanoparticle is about 5-50 nM in diameter.

Linker.

As described herein, the magnetic nanoparticles can be connected to a therapeutic agent through a linker. The linker can be (a) covalently bonded to the magnetic nanoparticle by at least one atom of the linker and (b) covalently bonded to a therapeutic agent at another atom of the linker. Thus, the linker can be covalently bonded to the magnetic nanoparticle or if the magnetic nanoparticle is coated it can be covalently bonded to the coating. It is also to be understood that if a magnetic nanoparticle is coated some of the linkers can be covalently bonded to the coating and some of the linkers can be covalently bonded to the magnetic nanoparticle. For example, the linker can be covalently bonded to the iron oxide magnetic nanoparticle through a silicon atom of the linker. The linker can also be bonded to a coated magnetic nanoparticle, such as a silica coated magnetic nanoparticle through a silicon atom of the linker. The linker can also be bonded to a coated magnetic nanoparticle, such as a gold-coated magnetic nanoparticle. For example, a sulfur atom of a linker can be covalently bonded to a gold atom of a gold-coated magnetic nanoparticle.

The linker can be covalently bound to the therapeutic agent via a functional group (e.g., ester, amide, carbonate, carbamate, urea, thioester, thioamide, thiocarbonate, thiocarbamate, thiourea) that allows the therapeutic agent to be cleaved from the functional group when the linker undergoes intramolecular cyclization as described herein. The therapeutic agent is generally connected to a carbonyl or thiocarbonyl moiety of the functional group via a labile bond. Thus, when the linker undergoes intramolecular cyclization the bond connecting the therapeutic agent to the carbonyl or thiocarbonyl moiety (for example a bond such as an oxygen, nitrogen or sulfur bonded to either the carbonyl or thiocarbonyl) of the functional group is broken thereby releasing the therapeutic agent from the linker. Accordingly, hydroxy, amine, or thioether groups of a therapeutic agent are particularly useful for forming the labile bond to the carbonyl or thiocarbonyl moiety of the functional group.

The linkers described herein can vary in length and composition and be branched or non-branched. In general the linker can comprise atoms selected from carbon, oxygen, nitrogen, sulfur and silicon. In one embodiment the linker comprises a carbonyl or thiocarbonyl and an amine nitrogen such as a primary amine nitrogen or secondary amine nitrogen. In one embodiment, the linker, upon heating (e.g., upon AMF irradiation of the attached magnetic NP), undergoes intramolecular cyclization thereby releasing the therapeutic agent from the linker. The intramolecular cyclization generally occurs through reaction of an amine nitrogen within the linker and the carbon of the carbonyl carbon or thiocarbonyl carbon of the functional group that connects the therapeutic agent to the linker.

In one embodiment the linker comprises about 4-50 atoms in the linker. In one embodiment the linker comprises about 4-40 atoms in the linker. In one embodiment the linker comprises about 4-30 atoms in the linker. In one embodiment the linker comprises about 4-20 atoms in the linker. In one embodiment the linker comprises about 4-15 atoms in the linker. In one embodiment the linker comprises about 7-50 atoms in the linker. In one embodiment the linker comprises about 7-40 atoms in the linker. In one embodiment the linker comprises about 7-30 atoms in the linker. In one embodiment the linker comprises about 7-20 atoms in the linker. In one embodiment the linker comprises about 7-15 atoms in the linker. In one embodiment the linker comprises about 6-15 atoms in the linker. In one embodiment the linker comprises about 7-14 atoms in the linker. In one embodiment the linker comprises about 8-14 atoms in the linker. In one embodiment the linker comprises about 9-13 atoms in the linker. In one embodiment any of the above the atoms are independently selected from carbon, nitrogen, oxygen, sulfur and silicon. In one embodiment any of the above the atoms are independently selected from carbon, nitrogen, oxygen, sulfur and silicon provided the linker contains at least one NH group and one group selected from (C=O) and (C=S). In one embodiment no oxygen, nitrogen, silicon or sulfur are directed bonded (e.g., adjacent) to another oxygen, nitrogen, silicon or sulfur. In one embodiment no oxygen, nitrogen or sulfur are directed bonded (e.g., adjacent) to another oxygen, nitrogen or sulfur.

It is to be understood that the magnetic nanoparticle may be bonded with multiple linker groups and that some of these groups are adjacent (e.g., in close proximity) to one another. In such situations it is possible that certain groups of the adjacent linkers may interact (e.g., be bonded to each other). One example of this would include linkers which comprise a silicon atom wherein the silicon atoms on adjacent linkers can be connected to one another via a bridging oxygen atom (e.g., —O—).

Therapeutic Agent

The term "therapeutic agent" includes agents that are useful for the treatment of a disease or a physiological condition in an animal (e.g., a mammal such as a human) and thus includes known drugs. Thus, the term "therapeutic agent" includes but is not limited to known drugs and/or drugs that have been approved for sale in the United States. For example, therapeutic agents include but are not limited to chemotherapeutic agents, antibiotic agents, antifungal agents, antiparasitic agents and antiviral agents. The term "therapeutic agent" agent also includes "prodrugs" of such therapeutic agents or drugs. The term "therapeutic agent" agent also includes functional group derivatives of such therapeutic agents or drugs. Such functional group derivatives include for example, but are not be limited to alcohols of the corresponding ketone of a therapeutic agent. Accordingly, the term "therapeutic agent" includes a therapeutic agent, a prodrug of a therapeutic agent and a functional group derivatives of therapeutic agent. It is to be understood that the bond between the therapeutic agent and the linker can be at any suitable atom of the therapeutic agent such as (a) the therapeutic agent itself, (b) the prodrug portion of the prodrug of a therapeutic agent or (c) the functional group derivative portion of the functional group derivative of a therapeutic agent.

Therapeutic agent can connected to the linker described herein by the removal of a hydrogen from the therapeutic agent (e.g., a residue of a therapeutic agent) which provides the open valency to be connected to the linker. In one embodiment the term —Z-$D^1$ of formula I can be a residue of a therapeutic agent and the corresponding group H—Z-$D^1$ can be the corresponding therapeutic agent. Thus, one embodiment provides therapeutic agents comprising one or more hydroxyl (—OH), thiol (—SH) or amine (e.g., primary (—$NH_2$) or secondary (—NH—, —NH($C_1$-$C_6$)alkyl), groups which groups can be connected to the linker as described herein.

In one embodiment the therapeutic agent is a therapeutic agent (e.g., a drug) or a prodrug of the therapeutic agent.

In one embodiment the therapeutic agent is a therapeutic agent (e.g., drug) and not a prodrug and not a functional group derivative of the therapeutic agent.

In one embodiment the therapeutic agent is selected from Cladribine, Azacitidine, Abraxane, Adcetris, Doxorubicin, Afinitor, Vinblastine, Amifostine, Amifostine, Arabinosylcytosine, Cytarabine, Pamidronic Acid, Nelarabine, Bicalutamide, Blemycin, Bortezomib, Cabazitaxel, Irinotecan, Camptothecin, Capecitabine, Temsirolimus, Daunorubicin, Cortisone, Decitabine, Dasatinib, Dexamethasone, Prednisolone, Dexamethasone Acetate, Mitoxantrone, Docetaxel, Hydroxycarbamide, Methylprednisolone, Epirubicin, Curcumin, Estramustine, Eribulin, Etoposide, Everolimus, Raloxifene, Fulvestrant, Floxuridine, Fludarabine, Fluoxymesterone, Gemcitabine, Goserelin, Topotecan, Hydrocortisone, Hydrocortone Phosphate, Idarubicin, Ixabepilone, Vincristine, Leuprolide (Leuprorelin), Megestrol, Vinorelbine, Nelarabine, Pentostatin, Octreotide, Paclitaxel, Streptozotocin, Teniposide, Valrubicin, Vorinostat, Zoledronic Acid Cladribine, Azacitidine, Mecaptopurine, Tioguanine, Actinomycin D, Doxorubicin, Anagrelide, Pemetrexed, Vinblastine, Melphalan, Methotrexate, Amifostine, Aminoglutethimide, Arabinosylcytosine, Cytarabine, Pamidronic Acid, Nelarabine, Axitinib, Bleomycin, Bosutinib, Folinic Acid (Na or Ca), Leucovorin, Vandetanib, Lenalidomide, Daunorubicin, Crizotinib, Dacarbazine, Decitabine, Dasatinib, Mitoxantrone, Eribulin, Erlotinib, Fludarabine, Pralatrexate, Gefitinib, Gemcitabine, Imatinib, Goserelin, Idarubicin, Lapatinib, Vincristine, Leuprolide, Procarbazine, Methotrexate, Mitomycin, Vinorebine, Nelarabine, Nilotinib, Pentostatin, Octreotide, Pazopanib, Sunitinib, Abraxane, Actinomycin D, Doxorubicin, Afinitor, Exemestane, Carfilzomib, Daunorubicin, Cortisone, Prednisolone, Prednisone, Dexamethasone Acetate, Docetaxel, Methylprednisolone, Epirubicin, Curcumin, Everolimus, Fluoxymesterone, Hydrocortisone, Hydrocortone Phosphate, Idarubicin, Ixabepilone, Vincristine, Megestrol, Valrubicin, Mesna, 13-cis-Retinoic Acid, Isotretinoin, Alitretinoin, Melphalan, Tretinoin, Methotrexate, Anastrozole, Bendamustine, Bexarotene, Carmustine, Lomustine, Chlorambucil and IbritumomabTiuxetan.

In one embodiment the therapeutic agent is a chemotherapeutic agent, an antibiotic agent, an antifungal agent, an antiparasitic agent or an antiviral agent or a prodrug thereof.

In one embodiment the therapeutic agent is a chemotherapeutic agent, an antibiotic agent, an antifungal agent, an antiparasitic agent or an antiviral agent.

In one embodiment the therapeutic agent has at least one amine (e.g., —NH$_2$ or —NH(C$_1$-C$_6$)alkyl), hydroxy or a thiol group.

In one embodiment the therapeutic agent has at least one hydroxy (—OH), thiol (—SH) or amine (e.g., primary (—NH$_2$) or secondary (—NH—, —NH(C$_1$-C$_6$)alkyl)) group.

In one embodiment the therapeutic agent has at least one hydroxy (—OH), thiol (—SH) or amine (e.g., primary (—NH$_2$) or secondary (—NH—)) group.

In one embodiment the therapeutic agent has at least one hydroxy or thiol group.

In one embodiment the therapeutic agent has at least one hydroxy group.

In one embodiment the therapeutic agent has at least one amine (e.g., —NH$_2$ or —NH(C$_1$-C$_6$)alkyl), hydroxy (—OH) or a thiol group and is attached to the linker through the amine (e.g., —NH$_2$ or —NH(C$_1$-C$_6$)alkyl), hydroxy (—OH) or a thiol group of the therapeutic agent.

In one embodiment the therapeutic agent has at least one hydroxyl (—OH), thiol (—SH) or amine (e.g., primary (—NH$_2$) or secondary (—NH—, —NH(C$_1$-C$_6$)alkyl)) group and is attached to the linker through the hydroxyl (—OH), thiol (—SH) or amine (e.g., primary (—NH$_2$) or secondary (—NH—, —NH(C$_1$-C$_6$)alkyl)) group of the therapeutic agent.

In one embodiment the therapeutic agent has at least one hydroxy (—OH), thiol (—SH) or amine (e.g., primary (—NH$_2$) or secondary (—NH—)) group and is attached to the linker through the hydroxyl (—OH), thiol (—SH) or amine (e.g., primary (—NH$_2$) or secondary (—NH—)) group of the therapeutic agent.

In one embodiment the therapeutic agent has at least one hydroxy or thiol (—SH) group and is attached to the linker through the hydroxy (—OH) or thiol (—SH) group of the therapeutic agent.

In one embodiment the therapeutic agent has at least one hydroxy group (—OH) and is attached to the linker through the hydroxy (—OH) group of the therapeutic agent.

In one embodiment the therapeutic agent has at least one amine (e.g., primary (—NH$_2$) or secondary (—NH—)) and is attached to the linker through the amine (e.g., primary (—NH$_2$) or secondary (—NH—)) group of the therapeutic agent.

In one embodiment the therapeutic agent has at least one thiol (—SH) group and is attached to the linker through the thiol (—SH) group of the therapeutic agent.

In one embodiment the therapeutic agent is selected from Cladribine, Azacitidine, Abraxane, Adcetris, Doxorubicin, Afinitor, Vinblastine, Amifostine, Amifostine, Arabinosylcytosine, Cytarabine, Pamidronic Acid, Nelarabine, Bicalutamide, Blemycin, Bortezomib, Cabazitaxel, Irinotecan, Camptothecin, Capecitabine, Temsirolimus, Daunorubicin, Cortisone, Decitabine, Dasatinib, Dexamethasone, Prednisolone, Dexamethasone Acetate, Mitoxantrone, Docetaxel, Hydroxycarbamide, Methylprednisolone, Epirubicin, Curcumin, Estramustine, Eribulin, Etoposide, Everolimus, Raloxifene, Fulvestrant, Floxuridine, Fludarabine, Fluoxymesterone, Gemcitabine, Goserelin, Topotecan, Hydrocortisone, Hydrocortone Phosphate, Idarubicin, Ixabepilone, Vincristine, Leuprolide (Leuprorelin), Megestrol, Vinorelbine, Nelarabine, Pentostatin, Octreotide, Paclitaxel, Streptozotocin, Teniposide, Valrubicin, Vorinostat and Zoledronic Acid.

In one embodiment the therapeutic agent is selected from Cladribine, Azacitidine, Mecaptopurine, Tioguanine, Actinomycin D, Doxorubicin, Anagrelide, Pemetrexed, Vinblastine, Melphalan, Methotrexate, Amifostine, Aminoglutethimide, Arabinosylcytosine, Cytarabine, Pamidronic Acid, Nelarabine, Axitinib, Bleomycin, Bosutinib, Folinic Acid (Na or Ca), Leucovorin, Vandetanib, Lenalidomide, Daunorubicin, Crizotinib, Dacarbazine, Decitabine, Dasatinib, Mitoxantrone, Eribulin, Erlotinib, Fludarabine, Pralatrexate, Gefitinib, Gemcitabine, Imatinib, Goserelin, Idarubicin, Lapatinib, Vincristine, Leuprolide, Procarbazine, Methotrexate, Mitomycin, Vinorebine, Nelarabine, Nilotinib, Pentostatin, Octreotide, Pazopanib and Sunitinib.

In one embodiment the therapeutic agent is selected from Abraxane, Actinomycin D, Doxorubicin, Afinitor, Exemestane, Carfilzomib, Daunorubicin, Cortisone, Prednisolone, Prednisone, Dexamethasone Acetate, Docetaxel, Methylprednisolone, Epirubicin, Curcumin, Everolimus, Fluoxymesterone, Hydrocortisone, Hydrocortone Phosphate, Idarubicin, Ixabepilone, Vincristine, Megestrol, Valrubicin and Mesna.

In one embodiment the therapeutic agent is selected from 13-cis-Retinoic Acid, Isotretinoin, Alitretinoin, Melphalan, Tretinoin, Methotrexate, Bendamustine, Bexarotene, Chlorambucil, and Ibritumomab Tiuxetan.

In one embodiment the therapeutic agent is selected from Carmustine, Lomustine, Chlorambucil and Bendamustine.

Targeting elements (e.g., an antibody fragment, a small molecule ligand of a cellular receptor) can be attached to the therapeutic nanoparticle at any suitable location including the magnetic nanoparticle, linker or therapeutic agent by any suitable means.

"Prodrug" of a therapeutic agent refers to a labile functional group which separates from the active compound during metabolism, systemically, inside a cell, by hydrolysis, enzymatic cleavage, or by some other process (Bundgaard, Hans, "Design and Application of Prodrugs" in A Textbook of Drug Design and Development (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug may include an active metabolite of drug itself.

"Alkyl" is a straight or branched saturated hydrocarbon. For example, an alkyl group can have 1 to 8 carbon atoms (i.e., $(C_1\text{-}C_8)$alkyl) or 1 to 6 carbon atoms (i.e., $(C_1\text{-}C_6$ alkyl) or 1 to 4 carbon atoms. "Alkylene" refers to an alkyl group having two monovalent radical centers derived by the removal of two hydrogen atoms from the same or two different carbon atoms of the alkyl.

"Alkenyl" is a straight or branched hydrocarbon with at least one (e.g., one or more) carbon-carbon double bond. For example, an alkenyl group can have 2 to 8 carbon atoms (i.e., $C_2\text{-}C_8$ alkenyl), or 2 to 6 carbon atoms (i.e., $C_2\text{-}C_6$ alkenyl). "Alkenylene" refers to an alkenyl group having two monovalent radical centers derived by the removal of two hydrogen atoms from the same or two different carbon atoms of the alkenyl.

"Alkynyl" is a straight or branched hydrocarbon with at least one (e.g., one or more) carbon-carbon, triple bond. For example, an alkynyl group can have 2 to 8 carbon atoms (i.e., $C_2\text{-}C_8$ alkyne), or 2 to 6 carbon atoms (i.e., $C_2\text{-}C_6$ alkynyl). "Alkynylene" refers to an alkynyl group having two monovalent radical centers derived by the removal of two hydrogen atoms from the same or two different carbon atoms of the alkyne.

The term "halo" or "halogen" as used herein refers to fluoro, chloro, bromo and iodo.

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e. $(C_3\text{-}C_7)$carbocycle). "Carbocyclene" refers to an carbocycle group having two monovalent radical centers derived by the removal of two hydrogen atoms from the same or two different carbon atoms of the carbocycle.

"Phenylene" refers to a phenyl group having two monovalent radical centers derived by the removal of two hydrogen atoms from two different carbon atoms of the phenyl.

The term "heteroalkyl" as used herein refers to an alkyl as defined herein, wherein one or more of the carbon atoms of the alkyl are replaced by an O, S, or $NR_q$, (or if the carbon atom being replaced is a terminal carbon with an OH, SH or $NR_{q2}$) wherein each $R_q$ is independently H or $(C_1\text{-}C_6)$alkyl. "Heteroalkylene" refers to a heteroalkyl group having two monovalent radical centers derived by the removal of two hydrogen atoms from a same or two different carbon atoms or an OH, SH or $NHR_q$ of the heteroalkyl.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur. Thus, the term includes 3, 4, 5, 6, 7 or 8-membered single saturated or partially unsaturated rings from about 1 to 7 carbon atoms and from about 1 to 4 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl.

Silica (silicon dioxide ($SiO_2$)) includes all forms of silica such as amorphous silica, silica gel, mesoporous silica and fumed silica.

Specific values listed below for radicals, substituents, and ranges are for illustration only; they do not exclude other defined values or other values within defined ranges for the radicals and substituents. It is to be understood that two or more values may be combined.

A specific group of compounds of formula I are compounds wherein V is —$OSi(G)_2$-, the magnetic nanoparticle is optionally coated with silica, and the dashed line represents a covalent bond between the oxygen atom of —OSi $(G)_2$- and the magnetic nanoparticle optionally coated with silica; or V is —S—, the magnetic nanoparticle is magnetic nanoparticle coated with gold, and the dashed line represents a covalent bond between —S— and the magnetic nanoparticle coated with gold.

A specific group of compounds of formula I are compounds wherein V is —$OSi(G)_2$-, the magnetic nanoparticle is coated with silica, and the dashed line represents a covalent bond between the oxygen atom of —$OSi(G)_2$- and the magnetic nanoparticle coated with silica.

A specific group of compounds of formula I are compounds wherein V is —$OSi(G)_2$-, the magnetic nanoparticle is an iron oxide nanoparticle coated with silica, and the dashed line represents a covalent bond between the oxygen atom of —$OSi(G)_2$- and the iron oxide nanoparticle coated with silica.

A specific group of compounds of formula I are compounds wherein V is —$OSi(G)_2$-, the magnetic nanoparticle is an iron oxide nanoparticle, and the dashed line represents a covalent bond between the oxygen atom of —$OSi(G)_2$- and the iron oxide nanoparticle.

A specific group of compounds of formula I are compounds wherein V is —$OSi(G)_2$-, the magnetic nanoparticle is an iron oxide nanoparticle optionally coated with silica, and the dashed line represents a covalent bond between the oxygen atom of —$OSi(G)_2$- and the iron oxide nanoparticle optionally coated with silica.

A specific group of compounds of formula I are compounds wherein V is —$OSi(G)_2$-, the magnetic nanoparticle is an iron oxide nanoparticle coated with silica, and the dashed line represents a covalent bond between the oxygen atom of —$OSi(G)_2$- and the iron oxide nanoparticle coated in silica.

A specific group of compounds of formula I are compounds wherein -L-D has the following formula Ia:

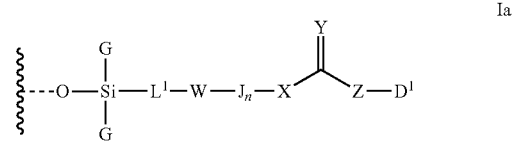

wherein the dashed bond represents a covalent bond to the magnetic nanoparticle.

A specific group of compounds of formula I are compounds wherein the magnetic nanoparticle is further coated in silica and wherein -L-D has the following formula Ia:

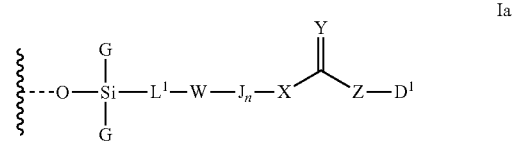

wherein the dashed bond represents a covalent bond to the magnetic nanoparticle further coated with silica.

A specific group of compounds of formula I are compounds wherein the magnetic nanoparticle is an iron oxide nanoparticle coated with silica and wherein -L-D has the following formula Ia:

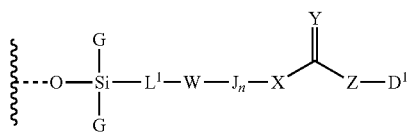

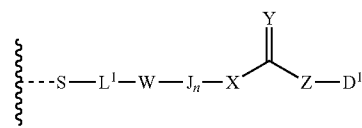

or a salt thereof, wherein the dashed bond represents a covalent bond to the iron oxide nanoparticle coated with silica.

A specific value for G is —OR$^{a1}$.

A specific group of compounds of formula I are compounds wherein each G is —OR$^{a2}$, wherein each —OR$^{a2}$ together with another —OR$^{a2}$ group on an adjacent -L-D group forms an —O—.

A specific group of compounds of formula I are compounds wherein each G is —OR$^{a1}$ or —OR$^{a2}$, wherein each —OR$^{a2}$ together with another —OR$^{a2}$ group on an adjacent -L-D group form an —O—.

A specific group of compounds of formula I are compounds wherein V is —S—, the magnetic nanoparticle is coated in gold, and the dashed line represents a covalent bond between —S— and the magnetic nanoparticle coated in gold.

A specific group of compounds of formula I are compounds wherein the dashed line represents a covalent bond between —S— and a gold atom of the magnetic nanoparticle coated in gold.

A specific group of compounds of formula I are compounds wherein V is —S—, the magnetic nanoparticle is an iron oxide nanoparticle coated in gold, and the dashed line represents a covalent bond between —S— and the iron oxide nanoparticle coated in gold.

A specific group of compounds of formula I are compounds wherein the dashed line represents a covalent bond between —S— and a gold atom of the iron oxide nanoparticle coated in gold.

A specific group of compounds of formula I are compounds wherein -L-D has the following formula Ib:

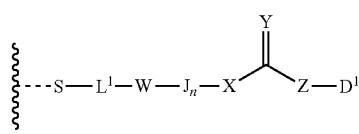

wherein the dashed bonds represent a covalent bond to the magnetic nanoparticle.

A specific group of compounds of formula I are compounds wherein the magnetic nanoparticle is coated with gold and wherein -L-D has the following formula Ib:

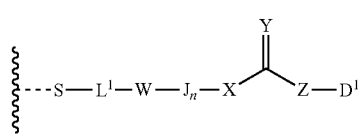

wherein the dashed bonds represent a covalent bond to the magnetic nanoparticle coated with gold.

A specific group of compounds of formula I are compounds wherein the magnetic nanoparticle is an iron oxide nanoparticle coated with gold and wherein -L-D is a compound of formula Ib:

or a salt thereof, wherein the dashed bonds represent a covalent bond to the iron oxide nanoparticle coated with gold.

A specific value for L$^1$ is (C$_1$-C$_6$)alkylene.

A specific value for L$^1$ is (C$_2$-C$_4$)alkylene.

A specific value for L$^1$ is (C$_1$-C$_6$)alkylene optionally substituted with one or more halogen.

A specific value for L$^1$ is (C$_2$-C$_4$)alkylene optionally substituted with one or more halogen.

A specific value for L$^1$ is —(CH$_2$)$_2$—, —(CH$_2$)$_3$— or —(CH$_2$)$_4$—.

A specific value for L$^1$ is —(CH$_2$)$_3$—.

A specific group of compounds of formula I are compounds wherein:
 (a) W is NH, X is CR$^c$R$^d$, and n is an integer from 0-5; or
 (b) W is NH, X is O, NR$^e$ or S, and n is an integer from 1-5.

A specific group of compounds of formula I are compounds wherein:
 (a) W is NH, X is CR$^c$R$^d$, and n is an integer from 0-5; or
 (b) W is NH, X is O, and n is an integer from 1-5.

A specific group of compounds of formula I are compounds wherein W is NH, X is CR$^c$R$^d$ and n is an integer from 0-5.

A specific group of compounds of formula I are compounds wherein R$^c$ and R$^d$ are each independently selected from H and methyl.

A specific group of compounds of formula I are compounds wherein R$^c$ and R$^d$ are each H.

A specific group of compounds of formula I are compounds wherein R$^c$ and R$^d$ are each methyl.

A specific group of compounds of formula I are compounds wherein W is —NH—, X is O, and n is an integer from 1-5.

A specific value for n is 2, 3 or 4.

A specific value for n is 1, 2, 3, 4 or 5.

A specific group of compounds of formula A are compounds wherein the sum of m and n is 1, 2, 3, 4 or 5.

A specific group of compounds of formula A are compounds wherein the sum of m and n is 1, 2, 3 or 4.

A specific group of compounds of formula A are compounds wherein the sum of m and n is 1, 2 or 3.

A specific group of compounds of formula I are compounds wherein each J is C(R$^b$)$_2$.

A specific group of compounds of formula I are compounds wherein each R$_b$ is independently H or methyl.

A specific value for R$_b$ is H.

A specific value for J$_n$ is —(CH$_2$)$_2$—, —(CH$_2$)$_3$—, —(CH$_2$)$_4$—, —CH$_2$CH$_2$CMe$_2$CH$_2$—.

A specific value for Y is O.

A specific value for Z is O, NH or S.

A specific group of compounds of formula I are compounds wherein the portion of formula I as shown in the formula below:

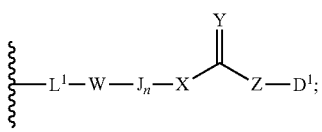

is selected from;

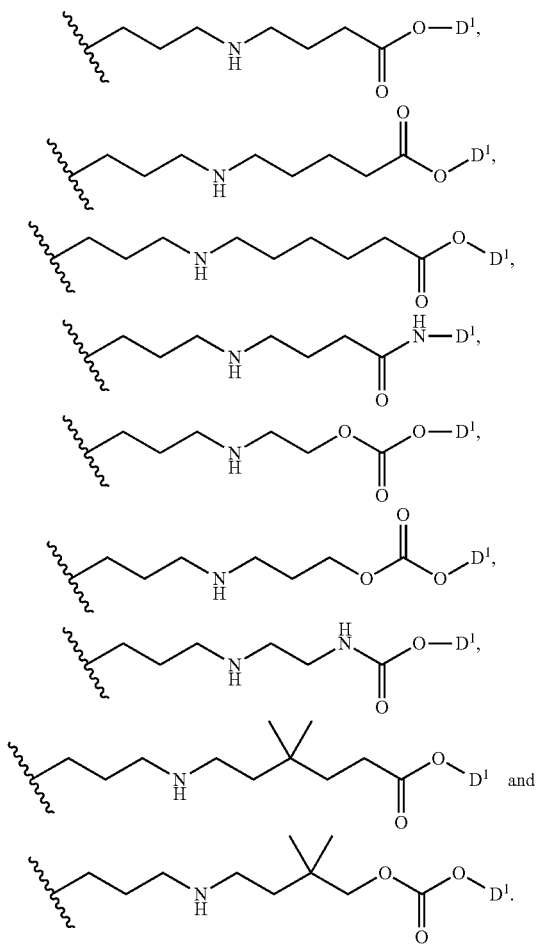

One embodiment provides a therapeutic magnetic nanoparticle comprising a magnetic nanoparticle covalently bonded to one or more -L-D groups wherein D is a therapeutic agent and L is a linker capable of undergoing an intramolecular cyclization.

One embodiment provides a therapeutic magnetic nanoparticle comprising a magnetic nanoparticle covalently bonded to one or more -L-D groups wherein -L-D is a compound of formula I:

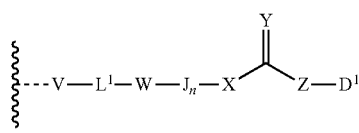

wherein

V is —OSi(G)$_2$-, the magnetic nanoparticle is an iron oxide nanoparticle, and the dashed line represents a covalent bond between the oxygen atom of —OSi(G)$_2$- and the iron oxide nanoparticle; or V is —S— the magnetic nanoparticle is an iron oxide nanoparticle coated in gold, and the dashed line represents a covalent bond between —S— and the iron oxide nanoparticle coated in gold;

L$^1$ is (C$_1$-C$_6$)alkylene, (C$_1$-C$_6$)heteroalkylene, (C$_2$-C$_6$)alkenylene, (C$_2$-C$_6$)alkynylene, phenylene or (C$_3$-C$_7$)carbocyclene;

each J is C(R$^b$)$_2$ wherein one C(R$^b$)$_2$ of J may be replaced by —O—;

(a) W is NH, X is CR$^c$R$^d$, and n is an integer from 0-5; or
(b) W is NH, X is O, NR$^e$ or S, and n is an integer from 1-5; or
(c) W is

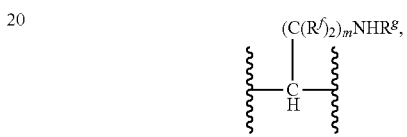

X is CR$^c$R$^d$, O, NR$^e$, S or absent, m is an integer from 0- and n is an integer from 0-5, wherein the sum of m and n is 0-5;

Y is O or S;

Z-D$^1$ is a residue of a therapeutic agent wherein Z is O, NR$^h$ or S;

each G is independently —OR$^{a1}$, —OR$^{a2}$ or (C$_1$-C$_6$)alkyl;

R$^{a1}$ is a covalent bond between the oxygen atom of —OR$^{a1}$ and the iron oxide nanoparticle;

each R$^{a2}$ is H or (C$_1$-C$_6$)alkyl; or two —OR$^{a2}$ groups of two adjacent L-D groups together form —O—;

each R$^b$ is independently selected from H and (C$_1$-C$_3$)alkyl; or two R$^b$ groups together with the carbon to which they are attached form a (C$_3$-C$_7$)carbocycle;

each R$^c$ is independently selected from H and (C$_1$-C$_6$)alkyl, and each R$^d$ is independently selected from H and (C$_1$-C$_6$)alkyl; or an R$^c$ group and an R$^d$ group together with the carbon to which they are attached form a (C$_3$-C$_7$)carbocycle;

each R$^e$ is independently selected from H and (C$_1$-C$_6$)alkyl;

each R$^f$ is independently selected from H and (C$_1$-C$_6$)alkyl; or two R$_f$ groups together with the carbon to which they are attached form a (C$_3$-C$_7$)carbocycle;

R$^g$ is selected from H and (C$_1$-C$_6$)alkyl; and

R$^h$ is selected from H and (C$_1$-C$_6$)alkyl;

or a salt thereof.

One embodiment provides a method for preparing a therapeutic magnetic nanoparticle, comprising reacting a compound of formula II:

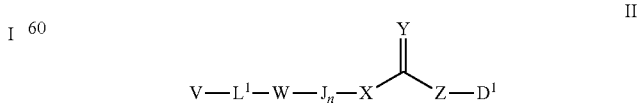

with an iron oxide nanoparticle when V is —Si(OR$^a$)$_3$; or with an iron oxide nanoparticle coated in gold when V is —SH;

wherein:
L¹ is $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene;
each J is $C(R^b)_2$ wherein one $C(R^b)_2$ of J may be replaced by —O—;
(a) W is NH, X is $CR^cR^d$, and n is an integer from 0-5; or
(b) W is NH, X is O, $NR^e$ or S, and n is an integer from 1-5; or
(c) W is

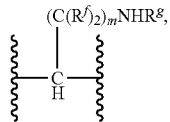

X is $CR^cR^d$, O, $NR^e$, S or absent, m is an integer from 0-5 and n is an integer from 0-5, wherein the sum of m and n is 0-5;
Y is O or S;
Z-D¹ is a residue of a therapeutic agent wherein Z is O, $NR^h$ or S;
$R^a$ is $(C_1-C_6)$alkyl;
each $R^b$ is independently selected from H and $(C_1-C_3)$alkyl; or two $R^b$ groups together with the carbon to which they are attached form a $(C_3-C_7)$carbocycle;
each $R^c$ is independently selected from H and $(C_1-C_6)$alkyl, and each $R^d$ is independently selected from H and $(C_1-C_6)$alkyl; or an $R^c$ group and an $R^d$ group together with the carbon to which they are attached form a $(C_3-C_7)$carbocycle;
each $R^e$ is independently selected from H and $(C_1-C_6)$alkyl;
each $R^f$ is independently selected from H and $(C_1-C_6)$alkyl; or two $R_f$ groups together with the carbon to which they are attached form a $(C_3-C_7)$carbocycle;
$R^g$ is selected from H and $(C_1-C_6)$alkyl; and
$R^h$ is selected from H and $(C_1-C_6)$alkyl;
or a salt thereof.

Salts

In cases where compounds are sufficiently basic or acidic, a salt of a therapeutic magnetic nanoparticle as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable salt. Alkali metal (for example, sodium, potassium or lithium) or alkaline earth metal (for example calcium) salts of carboxylic acids can also be made.

Administration

The method of administering the therapeutic magnetic nanoparticle to the desired area for treatment and the dosage may depend upon, but is not limited to, the type and location of the disease material. The size range of the nanoparticles may allow for microfiltration for sterilization. Some methods of administration include intravascular injection, intravenous injection, intraperitoneal injection, subcutaneous injection, and intramuscular injection. The nanoparticles may be formulated in an injectable format (e.g., suspension, emulsion) in a medium such as, for example, water, saline, Ringer's solution, dextrose, dimethylsulfoxide, albumin solution, and oils. The nanoparticles may also be administered to the patient through topical application via a salve or lotion, transdermally through a patch, orally ingested as a pill or capsule or suspended in a liquid or rectally inserted in suppository form. Nanoparticles may also be suspended in an aerosol or pre-aerosol formulation suitable for inhalation via the mouth or nose. Once administered to the patient, delivery of the nanoparticles to the target site may be assisted by an applied static magnetic field due to the magnetic nature of the nanoparticles. Assisted delivery may depend on the location of the targeted tissue. The nanoparticles may also be delivered to the patient using other methods. For example, the nanoparticles may be administered to the patient orally, or may be administered rectally. It is to be understood the therapeutic magnetic nanoparticles described herein may also be useful in diagnostics as well as studies in cells, tissues and animals.

The invention will now be illustrated by the following non-limiting Examples.

Example 1

Iron Oxide Nanoparticles

Iron oxide $(Fe_3O_4)$ NPs were prepared following the procedure described by Mikhaylova (Mikhaylova, M.; Kim, D. K.; Bobrysheva, N.; Osmolowsky, M.; Semenov, V.; Tsakalakos, T.; Muhammed, M., Superparamagnetism of Magnetite Nanoparticles: Dependence on Surface Modification. Langmuir 2004, 20, 2472-2477) using $FeCl_2$ and $FeCl_3$ in an aqueous caustic soda solution. Transmission Electron Microscopy (TEM) imaging was used to find that the average particle diameter was 5-10 nm. The zeta potential was measured to be ~−32 mV. Iron oxide $(Fe_3O_4)$ NPs with a diameter of 20-30 nm also were purchased from US Research Nanomaterials, Inc. IR analysis confirmed that the purchased NPs have the characteristic Fe-0 bond stretch at ~630 cm⁻¹ along with the OH stretch of the surface alcohols and hydrogen bound water (FIG. 1).

Linker Synthesis

The syntheses of the linkers (Scheme 1 and Examples herein below) started with commercial ω-amino acids. The amines were Boc-protected and then alkylated by treatment with NaH and allyl bromide. The protected N-allylamino acids then were esterified by reaction with a fluorescent alcohol (2-(9-anthracenyl)ethanol) serving as a model drug surrogate. Subsequent Boc deprotections were accomplished using trifluoroacetic acid (TFA). Hydrosilylations then were performed to incorporate the triethoxysilane group for subsequent loadings onto the $Fe_3O_4$ NPs.

Scheme 1 Linker synthesis where n = 3-5

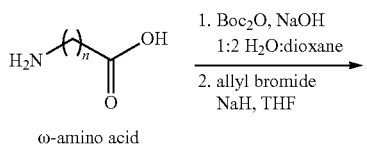

ω-amino acid

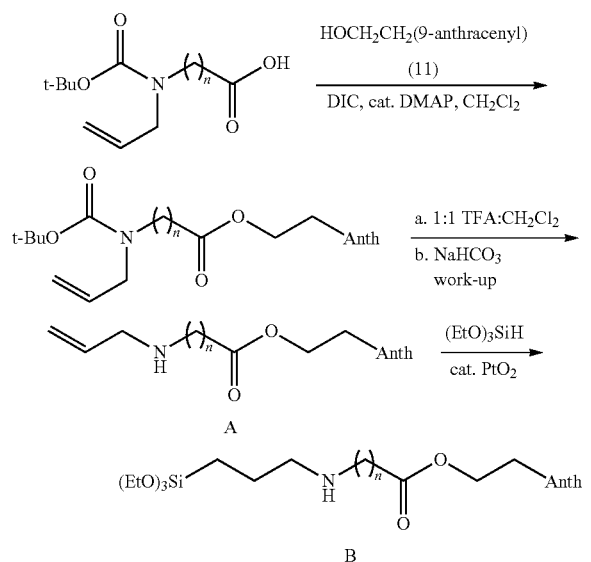

Attachment of a Drug Surrogate

Development of the thermo-labile linkers began with commercially available 9-anthracenecarboxaldehyde. The high ultraviolet (UV) and fluorescence capability of the anthracene ring ($\lambda_{max}$ 413 nm) allows for quantitative detections at low concentrations. An additional methylene group was synthetically inserted and the carbonyl group reduced to afford the model drug surrogate 2-(9-anthracenyl)ethanol (11) as depicted in Scheme 2.

Scheme 2
Synthesis of the model drug surrogate 2-(9-anthracenyl)ethanol (11)

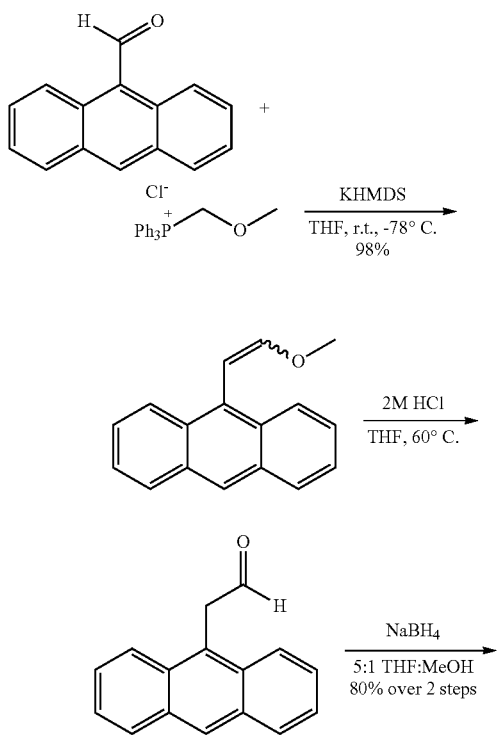

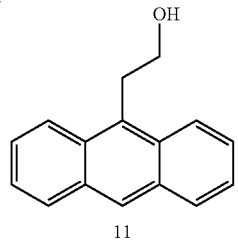

Demonstration of Heat-Induced Probe Release

Experiments were performed to verify that an alcohol-functionalized compound could be released from the linker in its original alcohol form. The four, five, and six carbon amino esters (compound family A, Scheme 1) were heated in toluene, starting at room temperature and heating to reflux in ~10° C. increments with a one-hour waiting time at each temperature. At the end of each hour the solutions were analyzed by thin-layer chromatography (TLC). The released anthracene alcohol 11 was first observed for the five-membered lactam at room temperature, the six-membered lactam was seen at ~35° C., and the seven-membered ring was not seen until the solution temperature had reached 100° C. The six-carbon amino ester was also tested under simulated biological conditions (PBS:dioxane solution) with similar results.

Next, the 5-10 nm iron oxide NPs were covalently bound to the silylated linkers (compound family B, Scheme 1) and the coated NPs then were heated in toluene where, once again, the released anthracene alcohol was observed by TLC analysis of the reaction solutions at the above indicated temperatures.

Attachment of the Linker to Fe$_3$O$_4$ NPs

Figure 2:
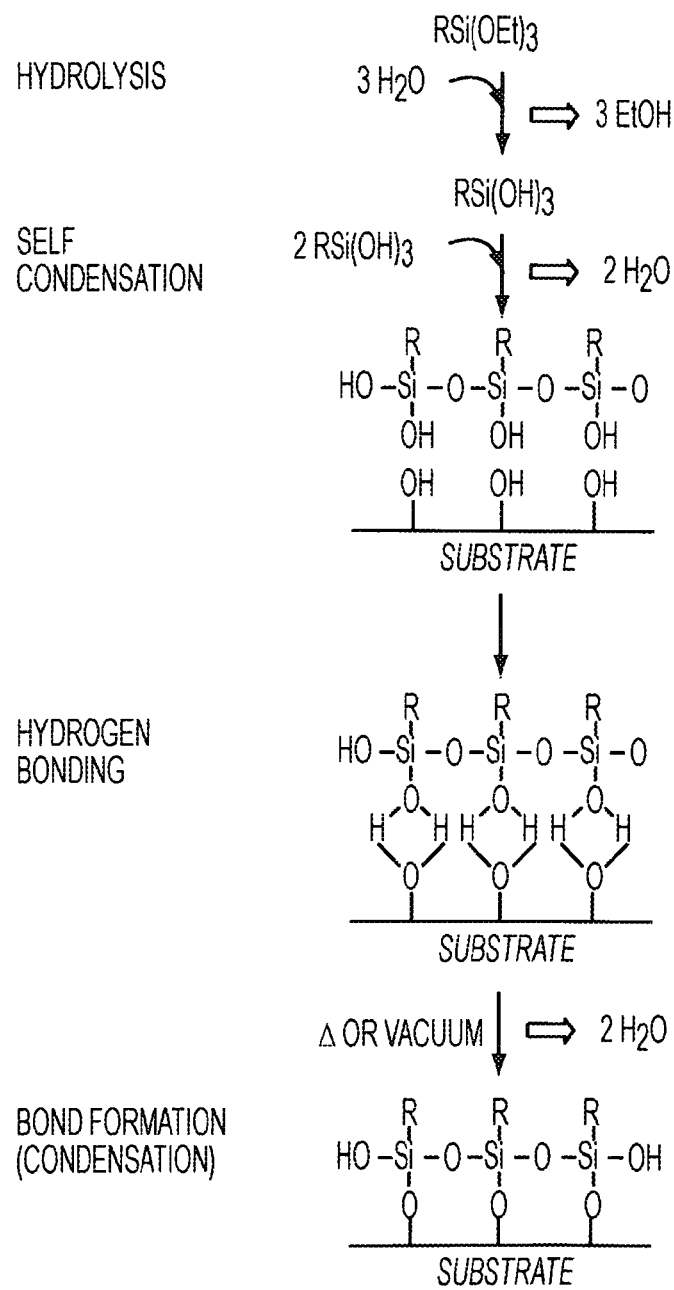
FIG. 2 illustrates the hydrolysis and condensation loading of alkoxysilane.
Figure 3:
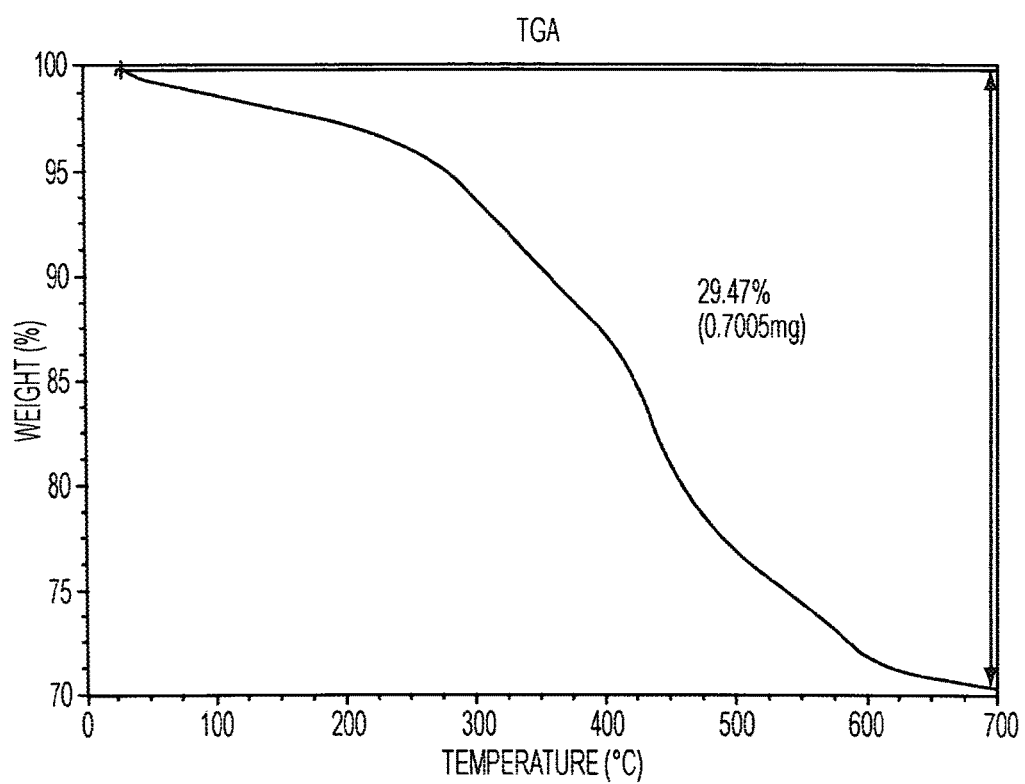
FIG. 3 illustrates the TGA of polymerized coating on $Fe_3O_4$ NPs.
Figure 4:
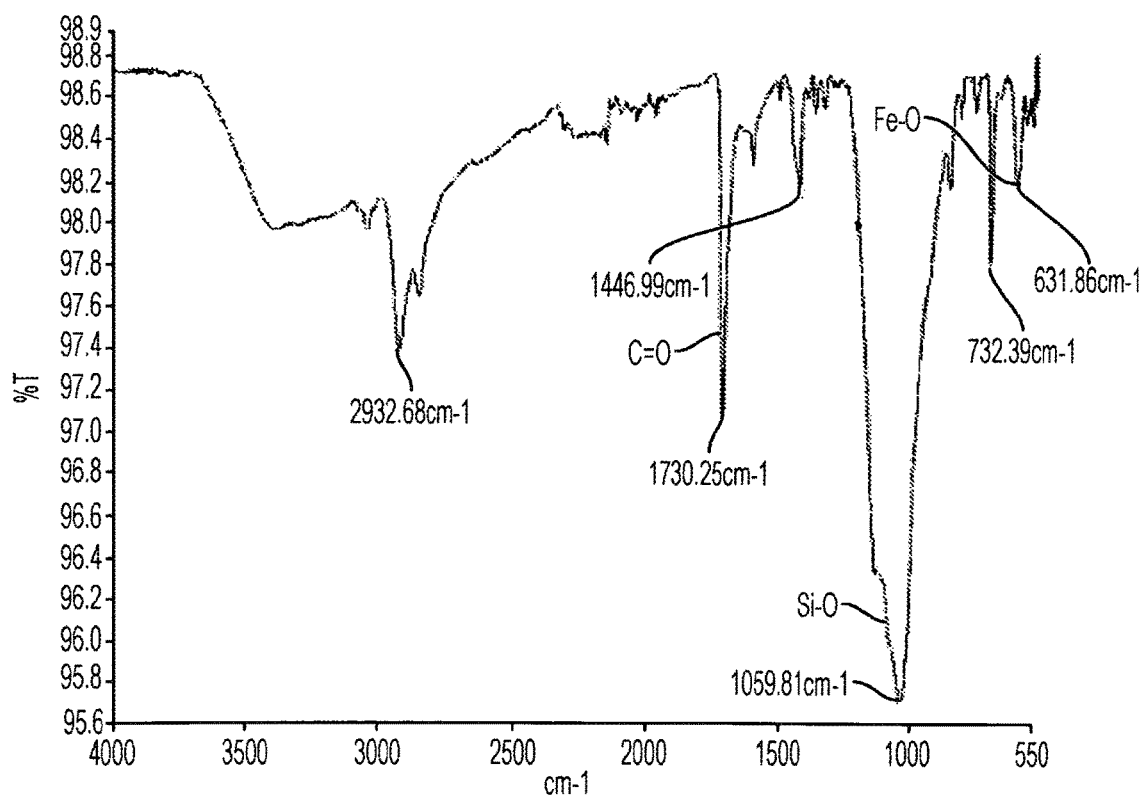
FIG. 4 illustrates the IR spectrum of polymerized coating on $Fe_3O_4$ NPs.
Figure 5A:
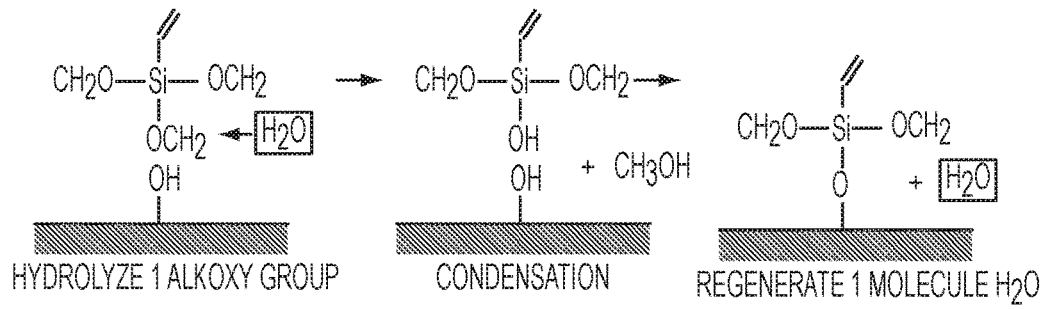
FIG. 5 illustrates the disordered polymerization of alkoxysilanes (a—desired; b+c—problematic polymerization).
Figure 5B:
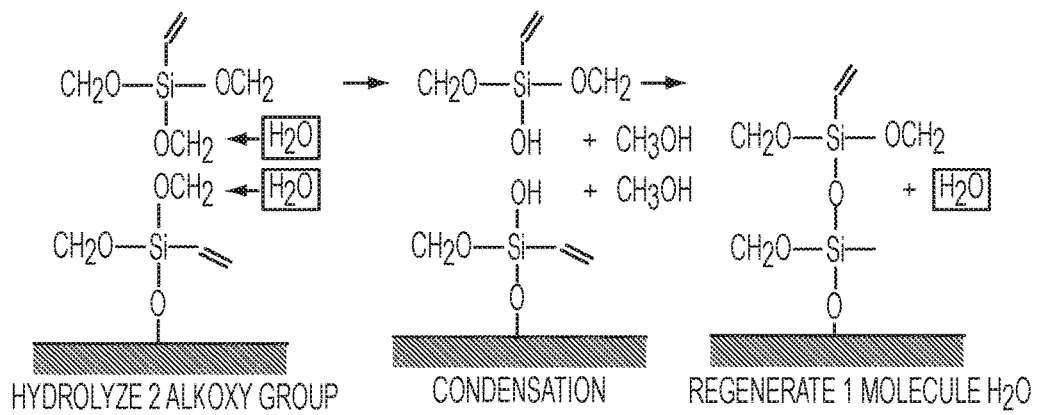
Figure 5C:
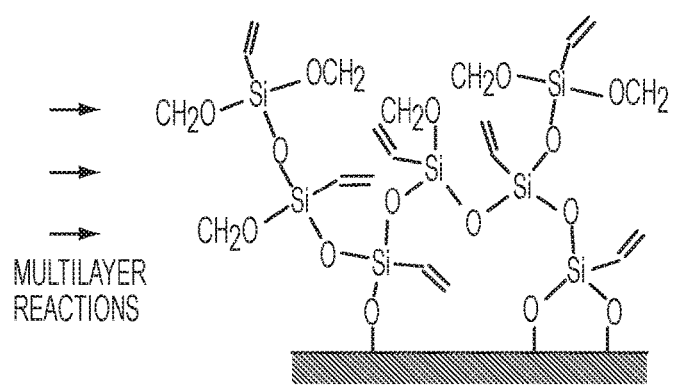

Witucki (Witucki, G. L. In *A Silane Primer: Chemistry and Applications of Alkoxy Silanes*, 57th Annual Meeting of the Federation of Societies for Coatings Technology, Chicago, Ill., Coating Technology: Chicago, Ill., 1992) outlined the first loading method that was employed in the system described herein (FIG. 2). Following the procedure described by Ma et. al. (Ming, M.; Zhang, Y.; Yu, W.; Shen, H.-y.; Zhang, H.-q.; Gu, N., Preparation and Characterization of Magnetite Nanoparticles Coated by Amino Silane. *Colloids and Surfaces, A: Physicochemical and Engineering Aspects* 2003, 212 (2-3), 219-226), Fe$_3$O$_4$ NPs were suspended in EtOH containing a small amount of water and then sonicated for 30 minutes. The alkoxysilane (~3 mmol per gram of NPs) was added to the suspension and sonicated for 10 minutes. An overhead stirrer was then affixed to the flask and the suspension was stirred overnight. Upon completion, the magnetic NPs were magnetically separated, washed five-times with EtOH, twice with Et$_2$O, and then dried under pump vacuum. Thermogravimetric analysis (TGA), along with IR spectroscopy, were used to confirm that linker attachment had occurred. The TGA (FIG. 3) showed a loading of 29.3% (w/w) and the IR spectrum (FIG. 4) showed intense peaks for Si—O, Si—O—Si, and Fe—O—Si bonds. Further support was provided by the presence of the ester carbonyl peak. Using equations outlined by Galeotti, (Galeotti, F.; Bertini, F.; Scavia, G.; Bolognesi, A., A Controlled Approach to Iron Oxide Nanoparticles Functionalization for Magnetic Polymer Brushes. *Journal of Colloid and Interface Science* 2011, 360, 540-547) the grafting density was found to be 6.79 molecules per nm$^2$. This density suggested excess polymerization prior to attachment to the iron oxide NP (FIG. 5).

Figure 6:
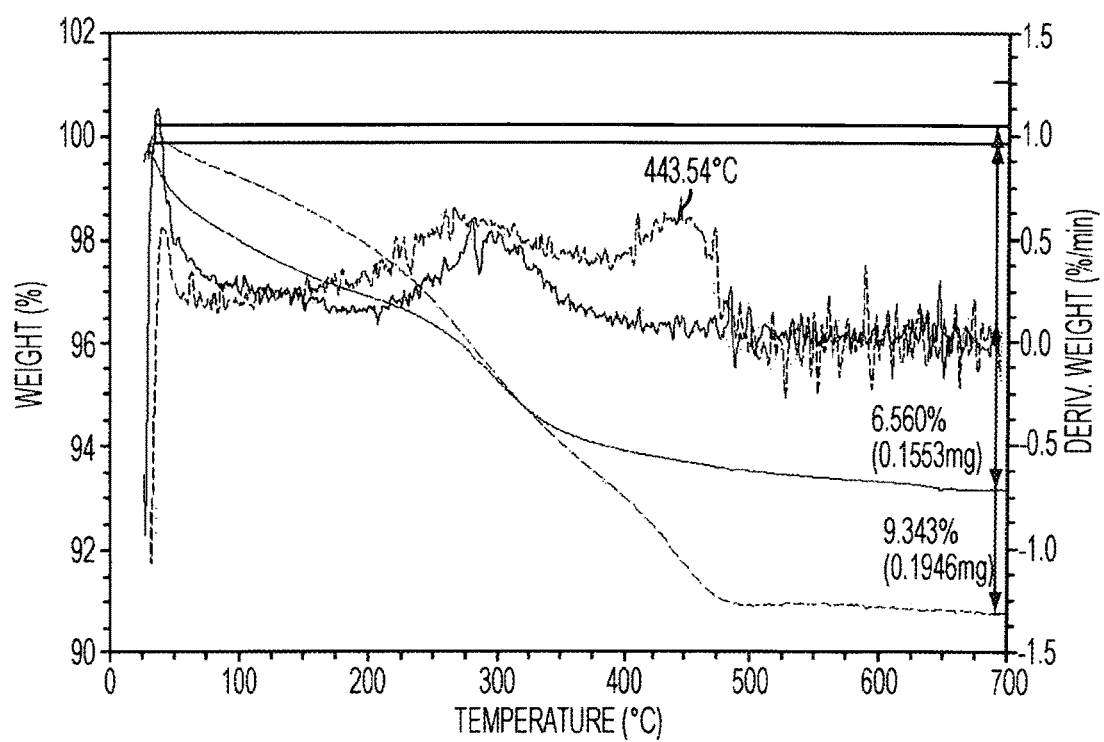
FIG. 6 illustrates the TGA of bare and coated $Fe_3O_4$ NPs.
Figure 7:
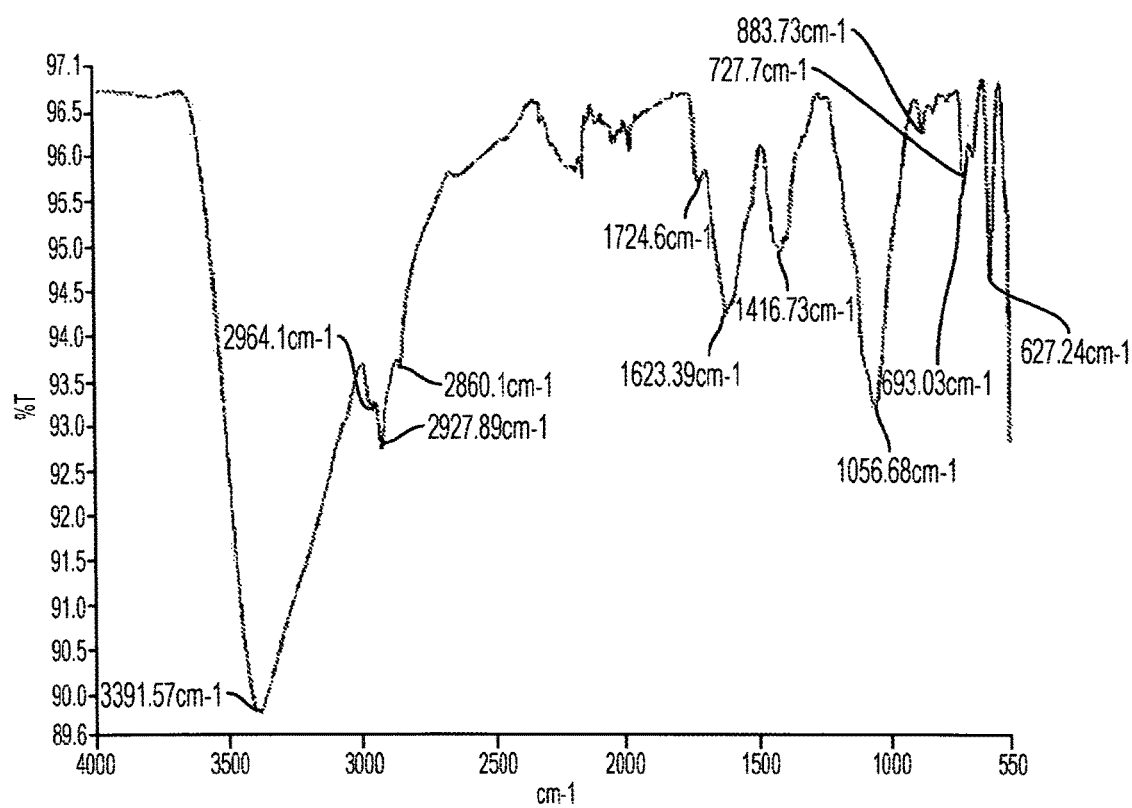
FIG. 7 illustrates the IR spectrum of coated $Fe_3O_4$ NPs.

To eliminate this problem, the loading method described by Galeotti was used. The NPs were placed in a flask flushed with nitrogen, CHCl₃ was then added via syringe and the suspension was sonicated for 30 minutes. The alkoxysilane (20 mmol per gram of NPs) was dissolved in a small amount of CHCl₃ and added to the suspension dropwise while sonication was continued. After the addition was complete, the sonication was continued for 10 minutes and then switched to an overhead stirrer at room temperature for two hours and then heated to 60° C. overnight. The coated NPs were magnetically separated and washed five-times with CHCl₃ and dried under pump vacuum. TGA analysis (FIG. 6) showed 9.3% (w/w) organic coating with a grafting density of 1.04 molecules per nm² and the IR spectrum (FIG. 7) displayed the presence of the ester and Si—O bonds with less intense peaks. These numbers are in agreement with Galeotti's results.

It is possible that reacting the coated NPs under vacuum at room temperature may not be enough to form the covalent Si—O bonds. While most published articles use a vacuum pump step at room temperature to form the 'covalent' bonds, higher temperatures (e.g., 100-110° C.) may be needed to effect the condensation reaction. The formation of the covalent bond happens in two steps as can be seen in FIG. 2. The first reaction is the hydrolysis of the alkoxysilane, followed by the hydrogen bonding of the linker to the surface hydroxyl groups on the NP. The second reaction is a condensation reaction between silanol and hydroxy-iron that is difficult to initiate.

Thus, the covalent loading procedures using different concentrations at the hydrolysis stage, heating temperatures for the condensation, and heating times for the condensation were evaluated. In general, as described by Galeotti, 20 mmol/g NPs maximize the graphing density, but such concentrations are not always needed. Also, though current condensation conditions (100-110° C. for 24 hours) work well, it may be preferable if milder conditions would suffice.

Figure 8:
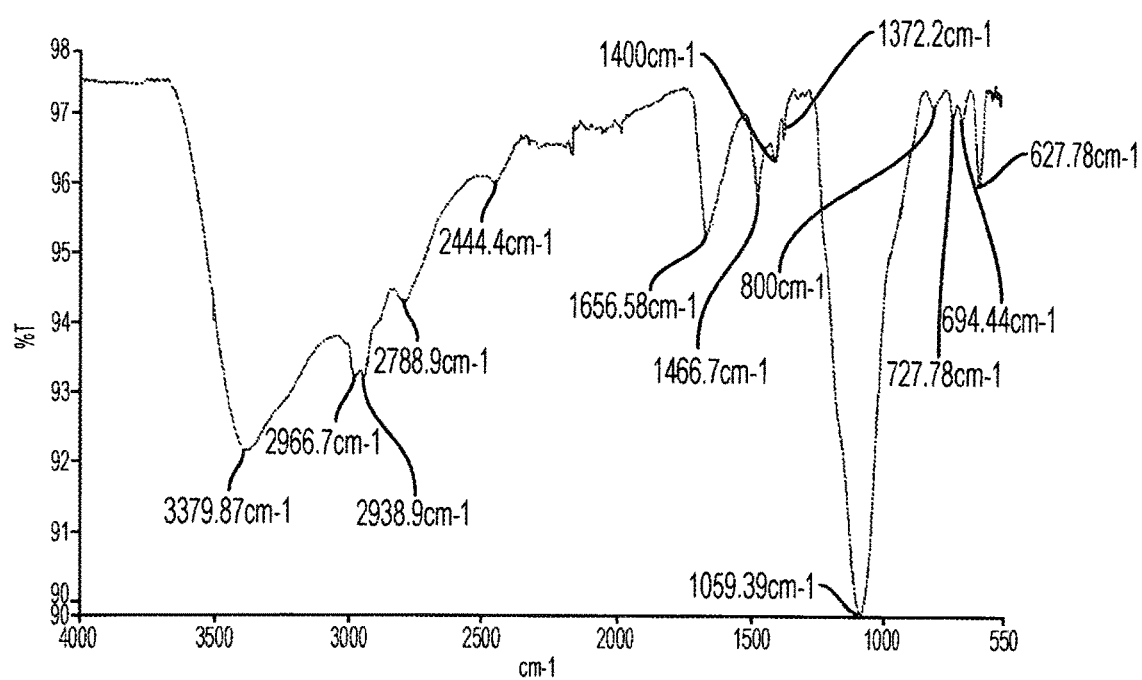
FIG. 8 illustrates the IR spectrum of Boc protected amine.
Figure 9:
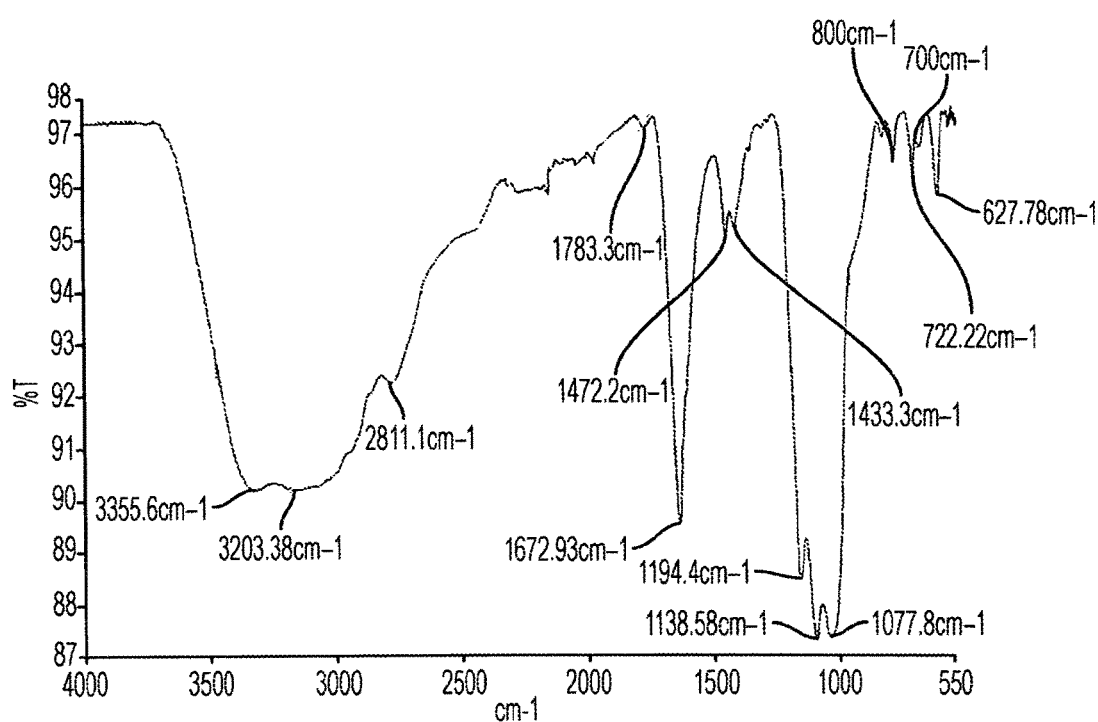
FIG. 9 illustrates the IR spectrum of the deprotected ammonium salt.
Figure 10:
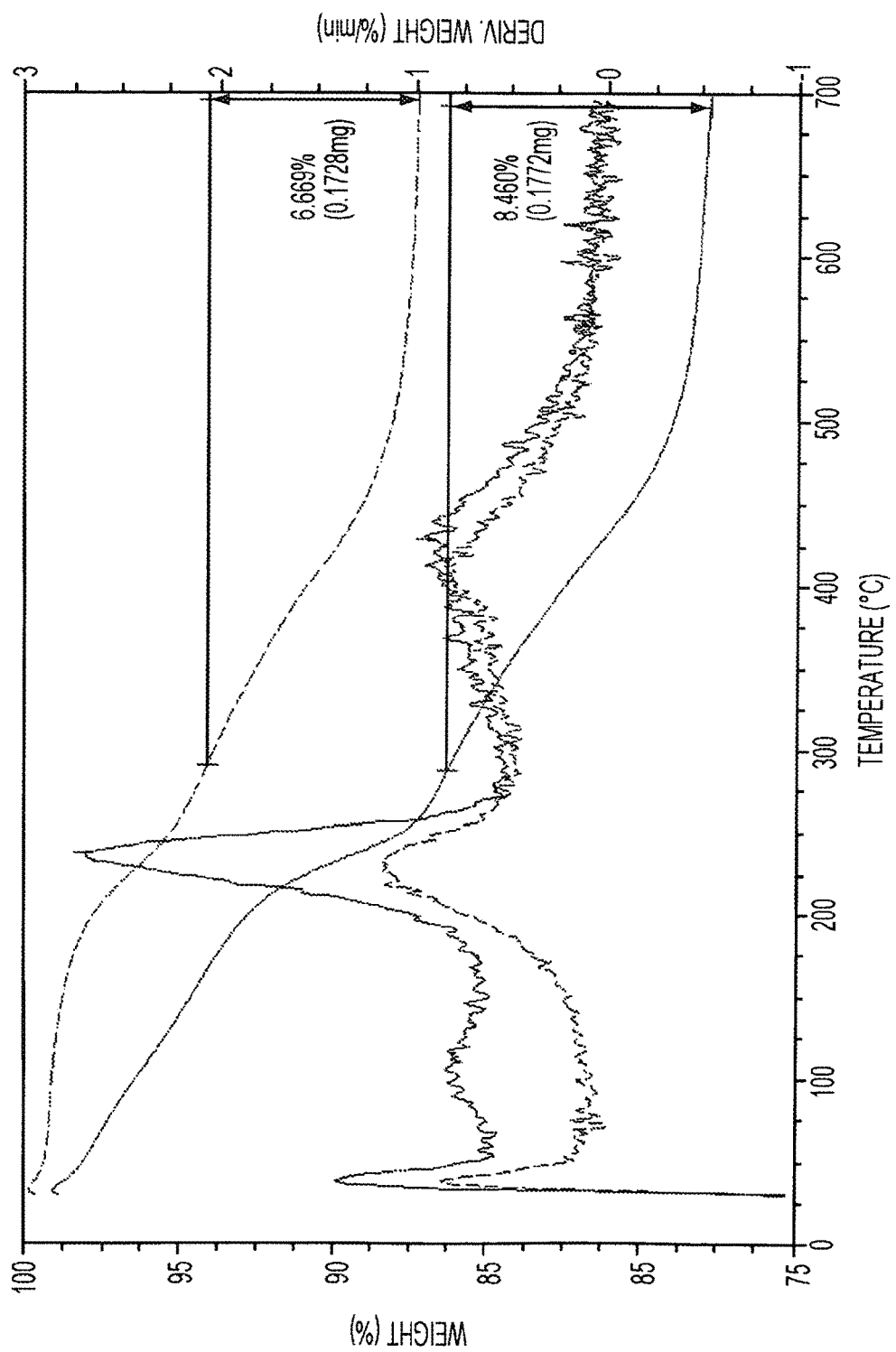
FIG. 10 illustrates the TGA of the Boc protected amine and deprotected ammonium salt.

To prevent lactamization during the loading condensation reaction, the secondary amine was Boc protected. After loading, the secondary amine would then be deprotected using trifluoroacetic acid (TFA), which might be acidic enough to dissolve some, if not all, of the NPs. An experiment was performed to show that little to no Fe₃O₄ was lost when subjected to 1:1 TFA:DCM (dichloromethane) for one hour. After magnetic separation and removal of the acidic solution, the NPs were dried on a vacuum pump for three-hours and reweighed to determine the amount of Fe₃O₄ removed by the TFA. To determine if the Si—O bond could withstand an hour in 1:1 TFA:DCM solution a new chain, N-Boc-N,N-methylallylamine, was synthesized, hydrosilylated, and affixed onto the NPs. IR spectroscopy (FIG. 8) and TGA (FIG. 10) verified the loading. The coated NPs were placed in a 1:1 TFA:DCM solution for one-hour at 0° C. At completion, the coated NPs were magnetically separated and the solution was removed followed by washing the coated NPs five times with DCM and drying under vacuum. IR spectroscopy (FIG. 9) and TGA (FIG. 10) verified the removal of Boc and the formation of an ammonium salt.

After the deprotection, the NPs were rinsed with NaHCO₃ solution to provide the secondary amine from the ammonium salt. To further verify the presence of the nucleophilic amine, FITC (fluorescein isothiocyanate) was added to the coated NPs in THF (tetrahydrofuran) and allowed to react overnight to form the FITC-NP thiourea bond. The FITC-NPs were magnetically separated and wash five-times with THF and dried under vacuum. Fluoresence measurements showed the presence of FITC ($\lambda_{max}$ 521 nm), verifying the deprotection and reaction of the amine.

To test the effectiveness of these results the six carbon Boc-protected linker was chosen. Following hydrosilylation, the linker was loaded onto the NPs and heated at ~110° C. for 24 hours. After heating, 6.4 mg of coated NPs were placed in a vial followed by 1:1 TFA:DCM for 30 minutes. The NPs were then magnetically separated and washed once with DCM, three times with saturated NaHCO₃ solution, five times with MeOH to remove water and NaHCO₃ salts, and finally twice with Et₂O. The NPs were then dried under vacuum to remove residual solvent.

Figure 11:
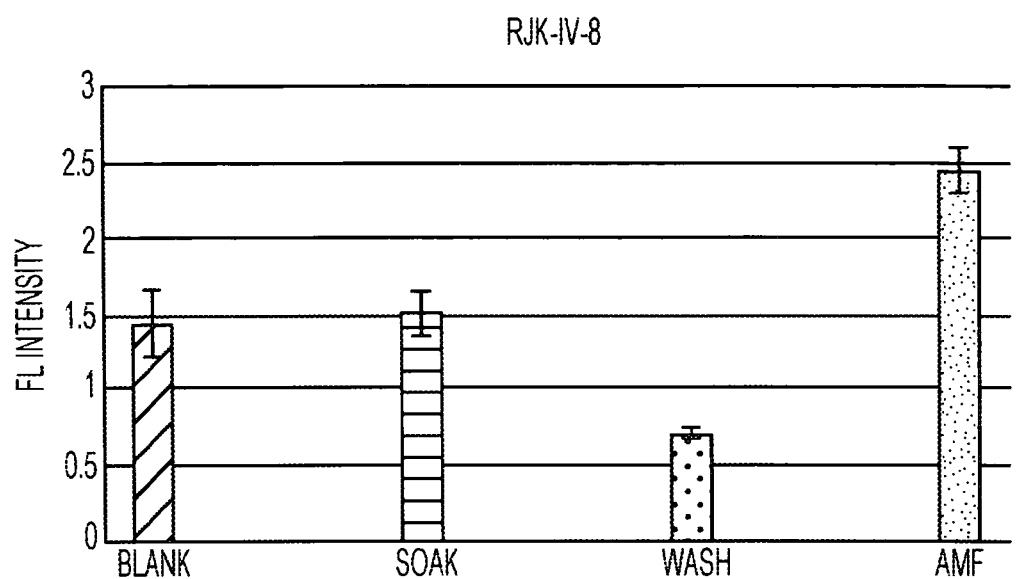
FIG. 11 illustrates the fluorescence (FL) measurements taken after Boc deprotection, soaking, and AMF steps.

Following work-up, the NPs were suspended in 1.5 mL 2:1 PBS:MeCN and soaked for 30 minutes followed by magnetic separation. The NPs were washed once with 1.5 mL of the PBS:MeCN solution and magnetically separated. A third 1.5 mL slug of 2:1 PBS:MeCN was added to the NPs and the suspension was subjected to 750 A AMF for 30 minutes. After AMF treatment, the NPs were magnetically separated. The three solutions obtained from the separations were centrifuged at 12,000 rpm for 25 minutes and the supernatant fluoresence was measured (FIG. 11). The data shows that AMF-treatment caused release of the drug surrogate from the NPs.

Example 2

Preparation of Ester Compounds 4.1, 4.2 and 4.3 and Carbonate Compounds 8.1 and 8.2

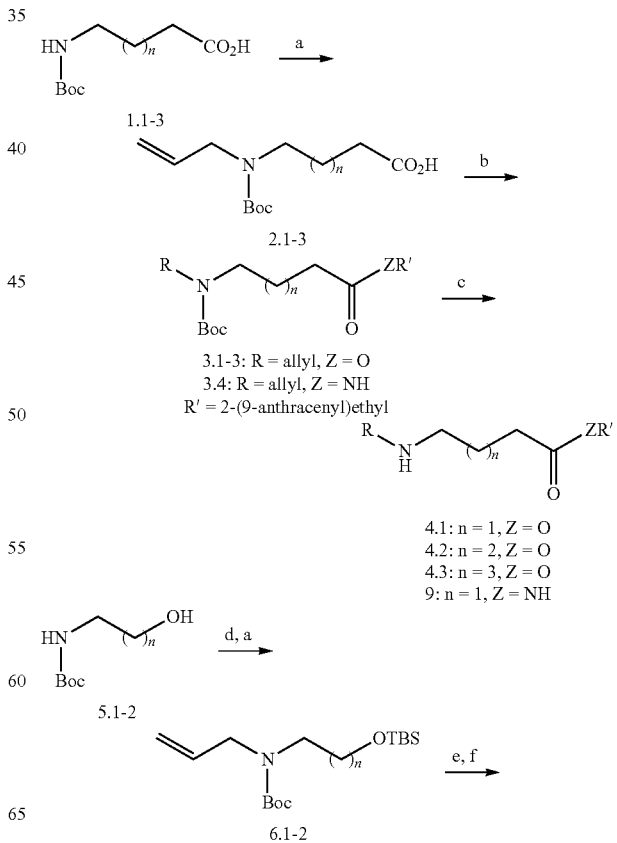

-continued

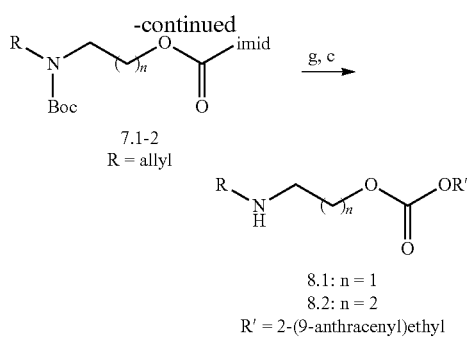

7.1-2
R = allyl 8.1: n = 1
8.2: n = 2
R' = 2-(9-anthracenyl)ethyl

Conditions: a. allyl bromide, NaH, THF, 0° C. to rt, 87%; b. 2-(9-anthracenyl)ethanol (or 2-(9-anthracenyl)ethanamine), DIC, cat. DMAP, $CH_2Cl_2$, 12 h, 59%; c. TFA, $CH_2Cl_2$, 0° C., 1 h, 100%; d. TBSCl, $Et_3N$, imidazole, $CH_2Cl_2$, 0° C. to rt, 98%; e. TBAF, THF, 0° C. to rt, 95%; f. $(imid)_2C=O$, $(i-Pr)_2NEt$, $CH_2Cl_2$, 0° C. to rt, 95%; g. 2-(9-anthracenyl)ethanol, KOH, toluene, 60° C., 45%.

Ester Analogs 4.1, 4.2 and 4.3

Preparation of 5-((tert-butoxycarbonyl)amino)pentanoic acid (1.2)

5-Aminopentanoic acid (1.99 g, 17.0 mmol) was dissolved in a 2:1 mixture of 1,4-dioxane:$H_2O$ (51 mL) and cooled to 0° C. A 1 M solution of NaOH (0.68 g, 17.1 mmol) was added, followed by the addition of di-tert-butyl dicarbonate ($Boc_2O$) (4.10 g, 18.8 mmol). After 18 h, the dioxane was removed in vacuo and the remaining aqueous layer was washed with EtOAc (19 mL). The aqueous phase was then acidified to pH ~3 with 1 M HCl and extracted with EtOAc (3×19 mL). The combined organics were dried over $MgSO_4$, filtered, and concentrated in vacuo to give crude 1.2 (white crystals) which was used in the next step without further purification. $^1$H NMR (400 MHz, $CDCl_3$) δ 1.43 (s, 9H), 1.52 (dt, J=7.2 Hz, 2H), 1.65 (dt, J=7.4 Hz, 2H), 2.36 (t, J=7.2 Hz, 2H), 4.61 (br s, 1H); $^{13}$C NMR (100 MHz, $CDCl_3$) δ 22.0, 28.6, 29.6, 33.7, 40.4, 79.5, 156.3, 178.9.

Preparation of 4-((tert-butoxycarbonyl)amino)butanoic acid (1.1)

$^1$H NMR (400 MHz, $CDCl_3$) δ 1.43 (s, 9H), 1.80 (dt, J=7.2 Hz, 2H), 2.38 (t, J=7.0 Hz, 2H), 3.16 (br s, 2H), 4.72 (br s, 1H), 9.34 (br s, 1H); $^{13}$C NMR (100 MHz, $CDCl_3$) δ 25.3, 28.6, 31.5, 40.0, 79.8, 156.4, 178.5.

Preparation of 6-((tert-butoxycarbonyl)amino)hexanoic acid (1.3)

$^1$H NMR (400 MHz, $CDCl_3$) δ 1.31-1.52 (m, 13H), 1.63 (dt, J=7.6 Hz, 2H), 2.33 (t, J=7.4 Hz, 2H), 3.08 (br s, 2H), 4.60 (br s, 1H), 10.44 (br s, 1H); $^{13}$C NMR (100 MHz, $CDCl_3$) δ 24.5, 26.4, 28.6, 29.9, 34.1, 40.6, 79.6, 156.1, 179.2.

Preparation of 5-(allyl(tert-butoxycarbonyl)amino)pentanoic acid (2.2)

Boc-protected amine 1.2 (4.65 g, 21.4 mmol) was added to a slurry of 60% NaH (4.28 g, 107.1 mmol) in dry tetrahydrofuran (THF) (140 mL) at 0° C. After one-hour of stirring, allyl bromide (5.56 mL, 64.2 mmol) was added dropwise. After 24 h, the reaction mixture was cooled to 0° C. and quenched with water until the reaction became transparent. The reaction was acidified to pH ~3 with 1 M HCl and the layers were separated. The aqueous phase was extracted with EtOAc (2×30 mL) and the combined organics washed with brine (50 mL), dried over $Na_2SO_4$, filtered and concentrated in vacuo. The crude material was purified by column chromatography ($SiO_2$, 1:1, EtOAc:hexanes) to give a light yellow oil 2.2 (4.77 g, 87%). $R_f$: 0.36 (1:1 EtOAc:hexanes); $^1$H NMR (400 MHz, $CDCl_3$) δ 1.43 (s, 9H), 1.51-1.64 (m, 4H), 2.35 (t, J=7.0 Hz, 2H), 3.17 (br s, 2H), 3.78 (br s, 2H), 5.09 (d, J=11.6 Hz, 2H), 5.70-5.78 (m, 1H); $^{13}$C NMR (100 MHz, $CDCl_3$) δ 22.1, 27.8, 28.6, 33.9, 46.2, 49.7, 79.9, 116.5, 134.4, 155.8, 179.6.

Preparation of 4-(allyl(tert-butoxycarbonyl)amino)butanoic acid (2.1)

$^1$H NMR (400 MHz, $CDCl_3$) δ 1.44 (s, 9H), 1.83 (dt, 2H), 2.34 (t, J=7.2 Hz, 2H), 3.24 (br s, 2H), 3.79 (br s, 2H), 5.08-5.12 (m, 2H), 5.71-5.80 (m, 1H); $^{13}$C NMR (100 MHz, $CDCl_3$) δ 23.5, 28.6, 31.4, 45.8, 49.7, 80.1, 116.7, 134.1, 155.9, 178.9.

6-(allyl(tert-butoxycarbonyl)amino)hexanoic acid (2.3)

$^1$H NMR (400 MHz, $CDCl_3$) δ 1.30 (dt, J=7.6 Hz, 2H), 1.43 (s, 9H), 1.83 (dt, J=7.6 Hz, 2H), 1.63 (dt, J=7.6 Hz, 2H), 2.33 (t, J=7.4 Hz, 2H), 3.15 (t, J=7.0 Hz, 2H), 3.77 (br s, 2H), 5.07-5.11 (m, 2H), 5.70-5.80 (m, 1H), 10.02 (br s, 1H); $^{13}$C NMR (100 MHz, $CDCl_3$) δ 24.6, 26.4, 28.1, 28.6, 34.2, 46.6, 49.7, 79.7, 116.3, 134.5, 155.8, 179.7.

Preparation of 2-(anthracen-9-yl)ethyl 5-(allyl(tert-butoxycarbonyl)amino)-pentanoate (3.2)

2.2 (255 mg, 0.99 mmol) and 2-(9-anthracenyl)ethanol (11) (196 mg, 0.88 mmol) were dissolved in dry $CH_2Cl_2$ (8 mL) with stirring. N,N'-Diisopropylcarbodiimide (DIC) (211.4 μL, 1.35 mmol) was added to the reaction solution followed by cat. 4-dimethylaminopyridine (DMAP). After 3 h, the white solids were filtered out and the filter cake was washed with $CH_2Cl_2$. The filtrate was condensed in vacuo and the crude material was purified by column chromatography ($SiO_2$, 0:100 to 1:19, EtOAc:$CH_2Cl_2$ gradient) to give a yellow oil 3.2 (242 mg, 59%). $R_f$: 0.46 (1:19, EtOAc:$CH_2Cl_2$); FT-IR 3058, 2981, 1729, 1685 cm$^{-1}$; $^1$H NMR (400 MHz, $CDCl_3$) δ 1.46 (s, 9H), 1.50-1.61 (m, 4H), 2.33 (t, J=7.4 Hz, 2H), 3.16 (br s, 2H), 3.79 (br s, 2H), 3.97 (t, J=7.8 Hz, 2H), 4.48 (t, J=7.8 Hz, 2H), 5.11 (d, J=11.6 Hz, 2H), 5.72-5.82 (m, 1H), 7.45-7.49 (m, 2H), 7.51-7.59 (m, 2H), 8.01 (d, J=8.4 Hz, 2H), 8.34 (d, J=9.2 Hz, 2H), 8.39 (s, 1H); $^{13}$C NMR (100 MHz, $CDCl_3$) δ 22.3, 27.5, 27.9, 28.6, 34.2, 46.3, 49.9, 64.3, 79.6, 116.2, 124.3, 125.1, 126.2, 127.0, 129.2, 129.4, 130.5, 131.7, 134.5, 155.7, 173.8.

Preparation of 2-(anthracen-9-yl)ethyl 4-(allyl(tert butoxycarbonyl)-amino)butanoate (3.1)

FT-IR 3058, 2981, 1730, 1685 cm$^{-1}$; $^1$H NMR (400 MHz, $CDCl_3$) δ 1.45 (s, 9H), 1.81 (br s, 2H), 2.31 (br s, 2H), 3.17 (br s, 2H), 3.78 (br s, 2H), 3.98 (t, J=7.8 Hz, 2H), 4.48 (t, J=7.8 Hz, 2H), 5.07-5.12 (m, 2H), 5.71-5.80 (m, 1H), 7.45-7.49 (m, 2H), 7.53-7.56 (m, 2H), 8.00 (d, J=8.4 Hz, 2H), 8.34 (d, J=8.8 Hz, 2H), 8.38 (s, 1H); $^{13}$C NMR (100

MHz, CDCl$_3$) δ 23.7, 27.5, 28.6, 31.7, 45.8, 49.9, 64.4, 79.8, 116.7, 124.3, 125.1, 126.2, 127.0, 129.2, 129.4, 130.5, 131.7, 134.3, 155.7, 173.5.

Preparation of 1-(anthracen-9-yl)propan-2-yl 4-(allyl(tert-butoxycarbonyl)amino)butanoate (Boc-Protected 15)

FT-IR 3058, 2980, 1726, 1686 cm$^{-1}$; $^1$H NMR (400 MHz, CDCl$_3$) δ 1.29 (br s, 3H), 1.44 (s, 9H), 1.64 (br s, 2H), 2.18 (br s, 2H), 3.03 (br s, 2H), 3.69 (br s, 2H), 3.78 (dd, J=7.2 Hz, 1H), 4.00 (dd, J=7.2 Hz, 1H), 5.03-5.09 (m, 2H), 5.29-5.44 (m, 1H), 5.66-5.76 (m, 1H), 7.44-7.48 (m, 2H), 7.52-7.56 (m, 2H), 7.99 (d, J=8.4 Hz, 2H), 8.37 (s, 1H), 8.39 (d, J=9.2 Hz, 2H); $^{13}$C NMR (100 MHz, CDCl$_3$) δ 20.2, 23.8, 28.6, 31.9, 33.8, 45.8, 49.9, 72.2, 79.7, 116.7, 125.0, 125.1, 126.0, 127.0, 129.4, 130.0, 130.8, 131.7, 134.3, 155.6, 173.0; FT-ICR-MS calcd for C$_{24}$H$_{28}$NO$_2^+$ [M−t-BuCO$_2$+2H]$^+$ (m/z) 362.2115, found 362.2124.

Preparation of 2-(anthracen-9-yl)ethyl 6-(allyl(tert-butoxycarbonyl)amino)hexanoate (3.3)

FT-IR 3058, 2936, 1730, 1684 cm$^{-1}$; $^1$H NMR (400 MHz, CDCl$_3$) δ 1.26 (dt, J=7.8 Hz, 2H), 1.42-1.54 (m, 11H), 1.58-1.64 (dt, J=7.6 Hz, 2H), 2.31 (t, J=7.6 Hz, 2H), 3.15 (br s, 2H), 3.80 (br s, 2H), 3.97 (t, J=7.8 Hz, 2H), 4.47 (t, J=8.0 Hz, 2H), 5.11 (d, J=12.0 Hz, 2H), 5.73-5.83 (m, 1H), 7.45-7.48 (m, 2H), 7.52-7.56 (m, 2H), 8.00 (d, J=8.4 Hz, 2H), 8.34 (d, J=8.8 Hz, 2H), 8.38 (s, 1H); $^{13}$C NMR (100 MHz, CDCl$_3$) δ 24.8, 26.5, 27.5, 28.2, 28.6, 34.4, 46.6, 49.6, 64.2, 79.5, 116.2, 124.3, 125.1, 126.2, 126.8, 126.9, 129.2, 129.4, 130.5, 131.7, 134.6, 155.7, 173.9.

Preparation of 2-(anthracen-9-yl)ethyl 5-(allylamino)pentanoate (4.2)

Trifluoroacetic acid (TFA) (0.74 mL, 9.60 mmol) was added to a solution of 3.2 (67.7 mg, 0.147 mmol) in dry CH$_2$Cl$_2$ (0.74 mL) at 0° C. and stirred for 1 h. The volatiles were removed in vacuo and the remaining residue was diluted with Et$_2$O (10 mL) and washed with NaHCO$_3$ (3×5 mL). The organic phase was washed with brine (5 mL), dried over Na$_2$SO$_4$, filtered and concentrated in vacuo to give a crude material 4.2 (53.0 mg orange oil, 100% yield) that was used in the next step without further purification. R$_f$: 0.20 (1:9, MeOH:CH$_2$Cl$_2$); $^1$H NMR (400 MHz, CDCl$_3$) δ 1.49 (dt, J=7.4 Hz, 2H), 1.64 (dt, J=7.6 Hz, 2H), 1.84 (br s, 1H), 2.32 (t, J=7.4 Hz, 2H), 2.59 (t, J=7.2 Hz, 2H), 3.24 (d, J=5.6 Hz, 2H), 3.97 (t, J=7.8 Hz, 2H), 4.48 (t, J=7.8 Hz, 2H), 5.11 (d, J=10.4 Hz, 1H), 5.18 (d, J=17.2 Hz, 1H), 5.86-5.96 (m, 1H), 7.47 (t, J=7.4 Hz, 2H), 7.55 (t, J=7.6 Hz, 2H), 8.01 (d, J=8.4 Hz, 2H), 8.34 (d, J=9.6 Hz, 2H), 8.38 (s, 1H); $^{13}$C NMR (100 MHz, CDCl$_3$) δ 22.8, 27.5, 29.5, 34.3, 48.9, 52.5, 64.3, 116.4, 124.3, 124.6, 125.1, 126.2, 126.9, 129.4, 130.5, 131.7, 136.7, 173.9; FT-ICR-MS calcd for C$_{24}$H$_{28}$NO$_2^+$ [M+H]$^+$ (m/z) 362.2115, found 362.2141.

Preparation of 2-(anthracen-9-yl)ethyl 4-(allylamino)butanoate (4.1)

$^1$H NMR (400 MHz, CDCl$_3$) δ 1.64 (br s, 1H), 1.79 (dt, J=7.2 Hz, 2H), 2.37 (t, J=7.2 Hz, 2H), 2.59 (t, J=7.2 Hz, 2H), 3.21 (d, J=6.4 Hz, 2H), 3.97 (t, J=7.8 Hz, 2H), 4.48 (t, J=7.8 Hz, 2H), 5.09 (d, J=10.0 Hz, 1H), 5.17 (dd, J=17.2, 1.4 Hz, 1H), 5.83-5.93 (m, 1H), 7.45-7.49 (m, 2H), 7.52-7.55 (m, 2H), 8.01 (d, J=8.4 Hz, 2H), 8.34 (d, J=8.8 Hz, 2H), 8.38 (s, 1H); $^{13}$C NMR (100 MHz, CDCl$_3$) δ 25.3, 27.5, 32.3, 48.6, 52.3, 64.3, 116.3, 124.4, 124.9, 125.7, 126.8, 129.3, 129.5, 130.5, 131.7, 136.7, 173.8; FT-ICR-MS calcd for C$_{23}$H$_{26}$NO$_2^+$ [M+H]$^+$ (m/z) 348.1958, found 348.1964.

Preparation of 2-(anthracen-9-yl)ethyl 6-(allylamino)hexanoate (4.3)

$^1$H NMR (400 MHz, CDCl$_3$) δ 1.32 (dt, J=7.8 Hz, 2H), 1.49 (dt, J=7.4 Hz, 2H), 1.62 (quin, J=7.6 Hz, 2H), 1.77 (br s, 1H), 2.31 (t, J=7.6 Hz, 2H), 2.60 (t, J=7.0 Hz, 2H), 3.26 (d, J=5.6 Hz, 2H), 3.98 (t, J=7.8 Hz, 2H), 4.48 (t, J=8.0 Hz, 2H), 5.10 (d, J=10.4 Hz, 1H), 5.19 (d, J=17.6 Hz, 1H), 5.87-5.97 (m, 1H), 7.45-7.49 (m, 2H), 7.53-7.57 (m, 2H), 8.01 (d, J=8.4 Hz, 2H), 8.34 (d, J=8.8 Hz, 2H), 8.38 (s, 1H); $^{13}$C NMR (100 MHz, CDCl$_3$) δ 24.9, 27.0, 27.5, 29.8, 34.4, 49.2, 52.6, 64.2, 116.3, 124.3, 125.1, 126.2, 126.9, 129.3, 129.4, 130.5, 131.7, 136.8, 174.0; FT-ICR-MS calcd for C$_{25}$H$_{30}$NO$_2^+$ [M+H]$^+$ (m/z) 376.2271, found 376.2278.

Carbonate Analogs 8.1 and 8.2

Preparation of tert-butyl(2-hydroxyethyl)carbamate (5.1)

Et$_3$N (2.51 mL, 18.0 mmol) was added to a solution of 2-ethanolamine (1.02 g, 16.7 mmol) in dry CH$_2$Cl$_2$ (33 mL) with stirring at 0° C. Boc$_2$O (3.93 g, 18.0 mmol) was then added to the reaction, turning the solution to an opaque white color that slowly cleared as the reaction proceeded. The reaction was stirred for 19 h and then was quenched with sat. NH$_4$Cl (30 mL) and the aqueous phase was extracted with CH$_2$Cl$_2$ (2×20 mL). The combined organics were washed with brine (30 mL), dried over Na$_2$SO$_4$, filtered and concentrated in vacuo to give a crude material 5.1 (light yellow oil) which was used in the next step without further purification. R$_f$: 0.38 (1:19, MeOH:CH$_2$Cl$_2$); $^1$H NMR (400 MHz, CDCl$_3$) δ 1.40 (s, 9H), 2.86 (br s, 1H), 3.23 (br s, 2H), 3.63 (br s, 5.03 (br s, 1H); $^{13}$C NMR (100 MHz, CDCl$_3$) δ 28.6, 43.3, 62.6, 79.8, 157.0.

Preparation of tert-butyl(3-hydroxypropyl)carbamate (5.2)

$^1$H NMR (400 MHz, CDCl$_3$) δ 1.42 (s, 9H), 1.64 (dt, J=5.8 Hz, 2H), 3.18 (br s, 1H), 3.25 (dt, J=6.4, 5.6 Hz, 2H), 3.63 (br s, 2H), 4.87 (br s, 1H); $^{13}$C NMR (100 MHz, CDCl$_3$) δ 28.6, 33.0, 37.1, 59.4, 79.8, 157.3.

Preparation of tert-butyl allyl(2-((tert-butyldimethylsilyl)oxy)ethyl)carbamate (6.1)

tert-Butyldimethylsilyl chloride (TBSCl) (3.06 g, 20.3 mmol) was added to a solution of 5.1 (2.70 g, 16.7 mmol), Et$_3$N (2.85 mL, 20.3 mmol) and imidazole (3.14 g, 46.1 mmol) in dry CH$_2$Cl$_2$ (40 mL) with stirring at 0° C. After 23 h, the reaction was quenched with water (25 mL) and the aqueous phase was extracted with CH$_2$Cl$_2$ (2×10 mL). The combined organics were washed with sat. NH$_4$Cl, dried over Na$_2$SO$_4$, filtered and condensed in vacuo. The crude material was purified by column chromatography (SiO$_2$, 3:7, EtOAc:hexanes) to give the silyl ether tert-butyl(2-((tert-butyldimethylsilyl)oxy)ethyl)carbamate as a colorless oil (4.52 g, 98%). R$_f$: 0.67 (1:1, EtOAc:hexanes); $^1$H NMR (400 MHz, CDCl$_3$) δ 0.06 (s, 6H), 0.89 (s, 9H), 1.44 (s, 9H), 3.23

(br s, 2H), 3.65 (br s, 2H), 4.84 (br s, 1H); $^{13}$C NMR (100 MHz, CDCl$_3$) δ −5.1, 18.5, 26.1, 28.6, 43.1, 62.5, 79.4, 156.2.

The silyl ether (4.52 g, 16.4 mmol) was then added to a slurry of NaH (1.08 g of 60% in mineral oil, 26.9 mmol) in dry THF (36 mL) at 0° C. and stirred for 1 h, and then allyl bromide (3.88 mL, 44.8 mmol) was added dropwise. The slurry was stirred for two days before cooling it to 0° C. and quenching it with water (20 mL). The aqueous phase was extracted with EtOAc (2×15 mL). The combined organics were washed with brine (20 mL), dried over Na$_2$SO$_4$, filtered and concentrated in vacuo. The crude material was purified by column chromatography (SiO$_2$, 1:19, Et$_2$O:hexanes) to give a light yellow oil 6.1 (4.36 g, 84%). R$_f$: 0.25 (1:19, Et$_2$O:hexanes); $^1$H NMR (400 MHz, CDCl$_3$) δ 0.04 (s, 6H), 0.88 (s, 9H), 1.44 (s, 9H), 3.29 (br s, 2H), 3.71 (br s, 2H), 3.89 (br s, 2H), 5.10 (br s, 2H), 5.76 (br s, 1H); $^{13}$C NMR (100 MHz, CDCl$_3$) δ −5.2, 18.5, 26.1, 28.7, 49.0, 51.6, 62.0, 79.6, 116.5, 134.6, 155.6.

Preparation of tert-butyl(3-((tert-butyldimethylsilyl)oxy)propyl)carbamate (Silyl Ether of 5.2)

$^1$H NMR (400 MHz, CDCl$_3$) δ 0.05 (s, 6H), 0.89 (s, 9H), 1.42 (s, 9H), 1.68 (dt, J=6.0 Hz, 2H), 3.23 (br s, 2H), 3.70 (t, J=5.6 Hz, 2H), 5.10 (br s, 1H); $^{13}$C NMR (100 MHz, CDCl$_3$) δ −3.4, 18.4, 26.1, 28.6, 32.2, 39.4, 62.4, 79.0, 156.2.

Preparation of tert-butyl allyl(3-((tert-butyldimethylsilyl)oxy)propyl)carbamate (6.2)

$^1$H NMR (400 MHz, CDCl$_3$) δ 0.04 (s, 6H), 0.88 (s, 9H), 1.44 (s, 9H), 1.72 (dt, J=6.0 Hz, 2H), 3.23 (br s, 2H), 3.61 (t, J=6.0 Hz, 2H), 3.82 (br s, 2H), 5.10 (d, J=11.2 Hz, 2H), 5.72-5.80 (m, 1H); $^{13}$C NMR (100 MHz, CDCl$_3$) δ −5.1, 26.1, 28.7, 32.0, 44.0, 49.2, 61.0, 79.5, 116.5, 134.6, 155.7.

Preparation of 2-(allyl(tert-butoxycarbonyl)amino) ethyl 1H-imidazole-1-carboxylate (7.1)

TBAF (18.0 mL of a 1 M solution, 18.0 mmol) was added dropwise to a solution of 6.1 (4.36 g, 13.8 mmol) in dry THF (28 mL) with stirring at 0° C. After 20 h, the reaction solution was diluted with Et$_2$O (50 mL) and washed with sat. NaHCO$_3$ (3×40 mL). The reaction solution was then washed with brine (40 mL), dried over Na$_2$SO$_4$, filtered and concentrated in vacuo. The crude material was purified by column chromatography (SiO$_2$, 1:1, EtOAc:hexanes) to give the corresponding alcohol tert-butyl allyl(2-hydroxyethyl)carbamate as a light yellow oil (2.65 g, 95%). R$_f$: 0.33 (1:1, EtOAc:hexanes); $^1$H NMR (400 MHz, CDCl$_3$) δ 1.45 (s, 9H), 3.07 (br s, 1H), 3.37 (br s, 2H), 3.72 (br s, 2H), 3.84 (br s, 2H), 5.10-5.14 (m, 2H), 5.78 (br s, 1H); $^{13}$C NMR (100 MHz, CDCl$_3$) δ 28.5, 50.0, 51.4, 62.5, 80.4, 116.6, 134.2, 157.4. N,N-Diisopropylethylamine (390 μL, 2.24 mmol) was added to a solution of the alcohol (296 mg, 1.47 mmol) in dry CH$_2$Cl$_2$ (37 mL) at 0° C. 1,1'-Carbonyldiimidazole (363 mg, 2.24 mmol) was then added to the cooled solution then the cooling bath was removed, allowing the reaction to slowly come to room temperature. After 24 h, the reaction was washed with water (2×20 mL), brine (20 mL), was dried over Na$_2$SO$_4$, filtered and concentrated in vacuo. The crude material was purified by column chromatography (SiO$_2$, EtOAc) to give a colorless oil 7.1 (404 mg, 93%). R$_f$: 0.50 (EtOAc); $^1$H NMR (400 MHz, CDCl$_3$) δ 1.41 (s, 9H), 3.59 (br s, 2H), 3.87 (br s, 2H), 4.48 (t, J=5.2 Hz, 2H), 5.11 (d, J=10.8 Hz, 2H), 5.76 (br s, 1H), 7.05 (s, 1H), 7.41 (s, 1H), 8.12 (s, 1H); $^{13}$C NMR (100 MHz, CDCl$_3$) δ 28.5, 45.4, 51.0, 66.0, 80.5, 116.7, 117.3, 130.9, 133.9, 137.3, 148.8, 155.7.

Preparation of tert-butyl allyl(3-hydroxypropyl)carbamate (Desilylated 6.2)

$^1$H NMR (400 MHz, CDCl$_3$) δ 1.45 (s, 9H), 1.66 (br s, 2H), 3.37 (br s, 2H), 3.55 (br s, 2H), 3.75 (br s, 2H), 5.12 (d, J=11.2 Hz, 2H), 5.71-5.81 (m, 1H); $^{13}$C NMR (100 MHz, CDCl$_3$) δ 28.5, 30.7, 42.6, 50.0, 58.5, 80.4, 116.7, 134.1, 157.1.

Preparation of 3-(allyl(tert-butoxycarbonyl)amino) propyl 1H-imidazole-1-carboxylate (7.2)

$^1$H NMR (400 MHz, CDCl$_3$) δ 1.43 (s, 9H), 2.01 (dt, J=6.6 Hz, 2H), 3.34 (br s, 2H), 3.82 (br s, 2H), 4.43 (t, J=6.4 Hz, 2H), 5.09-5.14 (m, 2H), 5.74-5.81 (m, 1H), 7.06 (s, 1H), 7.41 (s, 1H), 8.12 (s, 1H); $^{13}$C NMR (100 MHz, CDCl$_3$) δ 27.7, 28.6, 43.5, 50.3, 66.4, 80.2, 116.7, 117.3, 130.9, 134.2, 137.3, 148.8, 155.6.

Preparation of 2-(allylamino)ethyl(2-(anthracen-9-yl)ethyl) carbonate (8.1)

11 (85.5 mg, 0.385 mmol) was added to a solution of 7.1 (120 mg, 0.408 mmol) and 1 pellet of KOH in dry toluene (2 mL) at 60° C. After 5 h the reaction was concentrated in vacuo and the residue was diluted with CH$_2$Cl$_2$ (5 mL). The solution was washed with water (3×5 mL), dried over Na$_2$SO$_4$, filtered and concentrated in vacuo. The crude material was purified by column chromatography (SiO$_2$, 1:19 EtOAc:CH$_2$Cl$_2$) to give the corresponding carbonate tert-butyl allyl(2-(((2-(anthracen-9-yl)ethoxy)carbonyl)oxy)ethyl)carbamate as an orange oil (73.0 mg, 45%). R$_f$: 0.64 (1:19, EtOAc:hexanes); FT-IR 3017, 2971, 1740, 1230 cm$^{-1}$; $^1$H NMR (400 MHz, CDCl$_3$) δ 1.47 (s, 9H), 3.46 (br s, 2H), 3.95 (br s, 2H), 4.04 (t, J=8.0 Hz, 2H), 4.27 (br s, 2H), 4.50 (t, J=8.2 Hz, 2H), 5.13 (br s, 2H), 5.77 (br s, 1H), 7.44-7.50 (m, 2H), 7.51-7.58 (m, 2H), 8.02 (d, J=8.0 Hz, 2H), 8.34 (d, J=8.8 Hz, 2H), 8.40 (s, 1H); $^{13}$C NMR (100 MHz, CDCl$_3$) δ 27.5, 28.6, 45.5, 50.4, 66.2, 67.5, 79.4, 117.1, 124.1, 125.2, 126.4, 127.2, 128.3, 129.5, 130.5, 131.7, 134.1, 155.0, 155.4; FT-ICR-MS calcd for C$_{22}$H$_{24}$NO$_3^+$ [M−t-BuCO$_2$+2H]$^+$ (m/z) 350.1751, found 350.1758. This material was Boc-deprotected using the procedure outlined for synthesis of 4.2 above to afford carbonate 8.1.

Preparation of 3-(allylamino)propyl(2-(anthracen-9-yl)ethyl) carbonate (8.2)

Data for corresponding N-Boc analog tert-butyl allyl(3-(((2-(anthracen-9-yl)ethoxy)carbonyl)oxy)propyl)carbamate: FT-IR 3017, 2971, 1739, 1229 cm$^{-1}$; $^1$H NMR (400 MHz, CDCl$_3$) δ 1.47 (s, 9H), 1.92 (br s, 2H), 3.30 (br s, 2H), 3.83 (br s, 2H), 4.05 (t, J=8.0 Hz, 2H), 4.19 (t, J=6.2 Hz, 2H), 4.49 (t, J=8.2 Hz, 2H), 5.13 (d, J=11.2 Hz, 2H), 5.74-5.84 (m, 1H), 7.46-7.50 (m, 2H), 7.54-7.58 (m, 2H), 8.02 (d, J=8.0 Hz, 2H), 8.34 (d, J=8.8 Hz, 2H), 8.40 (s, 1H); $^{13}$C NMR (100 MHz, CDCl$_3$) δ 27.6, 28.0, 28.6, 43.9, 49.8, 66.0, 67.3, 79.9, 116.8, 124.1, 125.2, 126.4, 127.2, 128.3, 129.5, 130.5, 131.7, 134.3, 155.5, 155.6; FT-ICR-MS calcd for C$_{23}$H$_{26}$NO$_3^+$ [M−t-BuCO$_2$+2H]$^+$ (m/z) 364.1907, found 364.1911. This material was Boc-deprotected using the procedure outlined for synthesis of 4.2 above to afford carbonate 8.2.

Example 3

Preparation of Amide Compound 9

Preparation of 4-(allylamino)-N-(2-(anthracen-9-yl)ethyl)butanamide (9)

DIC (33 μL, 0.21 mmol) and cat. DMAP were added to a solution of 2.1 (38 mg, 0.15 mmol) and 2-(9-anthracenyl)ethanamine (12) (31 mg, 0.14 mmol) in dry $CH_2Cl_2$ at room temperature with stirring. After 2 h, the white precipitate was filtered out and the filter cake was washed with $CH_2Cl_2$ and concentrated in vacuo. The crude material was purified by column chromatography ($SiO_2$, 0:100 to 1:1, EtOAc:hexanes gradient) to give tert-butyl allyl(4-((2-(anthracen-9-yl)ethyl)amino)-4-oxobutyl)carbamate as a yellow oil (45 mg, 72%). $R_f$: 0.59 (EtOAc); FT-IR 3445, 3058, 2970, 1679, 1520 cm$^{-1}$; $^1$H NMR (400 MHz, CDCl$_3$) δ 1.43 (s, 9H), 1.80 (quin, J=6.8 Hz, 2H), 2.11 (br s, 2H), 3.19 (br s, 2H), 3.65-3.70 (m, 2H), 3.76 (br s, 2H), 3.87 (t, J=7.6 Hz, 2H), 5.08-5.11 (m, 2H), 2H), 5.70-5.79 (m, 1H), 6.74 (br s, 1H), 7.43-7.46 (m, 2H), 7.49-7.53 (m, 2H), 7.98 (d, J=8.4 Hz, 2H), 8.34 (br s, 2H); $^{13}$C NMR (100 MHz, CDCl$_3$) δ 24.4, 27.9, 28.6, 33.7, 40.6, 45.7, 49.8, 79.9, 116.5, 124.5, 125.1, 126.0, 126.5, 129.3, 130.3, 131.3, 131.7, 134.2, 156.3, 173.1; FT-ICR-MS calcd for $C_{23}H_{27}N_2O^+$ [M−t-BuCO$_2$+2H]$^+$ (m/z) 347.2118, found 347.2143. This material was Boc-deprotected using the procedure outlined for synthesis of 4.2 above to afford amide 9.

Example 4

Preparation of Carbamate Compound 10

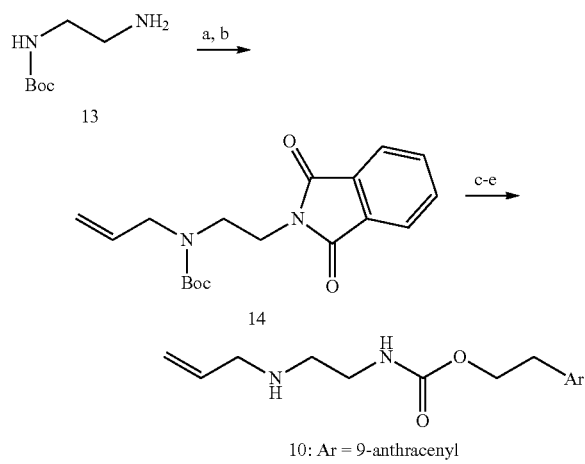

10: Ar = 9-anthracenyl

Conditions: a. phthalic anhydride, toluene, reflux, 77%; b. allyl bromide, NaH, THF, 0° C. to rt, 58%; c. hydrazine monohydrate, 2:1 CH$_2$Cl$_2$:EtOH, 0° C. to rt, 92%; d. ArCH$_2$CH$_2$OC(O)Cl, Et$_3$N, CH$_2$Cl$_2$, 0° C. to rt, 12 h, 41%; e. TFA, CH$_2$Cl$_2$, 0° C. 1 h.

Preparation of tert-butyl(2-aminoethyl)carbamate (13)

Ethylenediamine (9.2 mL, 137.6 mmol) was added dropwise via syringe to dry $CH_2Cl_2$ (82 mL) at 0° C. with stirring. A solution of Boc$_2$O (5.60 g, 25.7 mmol) in dry $CH_2Cl_2$ (76 mL) was added dropwise over 8 h with continued chilling. The reaction was stirred overnight. Precipitated solids were filtered and the filter cake was washed with $CH_2Cl_2$. The filtrate was condensed in vacuo, and then poured into NaHCO$_3$ solution (75 mL), which produced an exotherm, and shaken. The aqueous solution was extracted with $CH_2Cl_2$ (3×50 mL), and then the combined organics were dried over Na$_2$SO$_4$, filtered and condensed in vacuo to give a crude material 13 (turbid oil, 4.50 g) which was used in the next step without further purification. $R_f$: 0.24 (10:2:88, MeOH:NH$_4$OH:CH$_2$Cl$_2$); $^1$H NMR (400 MHz, CDCl$_3$) δ 1.40 (s, 9H), 2.76 (br s, 2H), 3.14 (br s, 2H), 5.05 (br s, 1H); $^{13}$C NMR (100 MHz, CDCl$_3$) δ 28.5, 41.9, 43.4, 79.3, 156.4.

Preparation of tert-butyl allyl(2-(1,3-dioxoisoindolin-2-yl)ethyl)carbamate (14)

Phthalic anhydride (4.18 g, 28.2 mmol) was added to a solution of 13 (4.11 g, 25.7 mmol) in toluene (86 mL) with stirring and the reaction flask was fitted with a Dean-Stark apparatus. The mixture was heated to reflux for 6.5 h with the phthalic anhydride slowly going into solution. After the heat was removed, the solution was allowed to stir overnight where a precipitate dropped out of solution. The mixture was washed with water (3×50 mL) and the combined aqueous phases were extracted with EtOAc (2×30 mL). The combined organics were washed with brine (50 mL), dried over Na$_2$SO$_4$, filtered and concentrated in vacuo. The crude material was purified by column chromatography (SiO$_2$, 1:19 to 1:1, EtOAc:CH$_2$Cl$_2$ gradient) to give the corresponding phthalimide tert-butyl(2-(1,3-dioxoisoindolin-2-yl)ethyl)carbamate as a white solid (5.76 g, 77%). $R_f$: 0.27 (1:19, EtOAc:hexanes); $^1$H NMR (400 MHz, CDCl$_3$) δ 1.33 (s, 9H), 3.42 (br s, 2H), 3.82 (t, J=5.6 Hz, 2H), 4.83 (br s, 1H), 7.70-7.72 (m, 2H), 7.82-7.86 (m, 2H); $^{13}$C NMR (100 MHz, CDCl$_3$) δ 28.4, 38.3, 39.8, 79.7, 123.5, 132.3, 134.2, 156.2, 168.7.

The phthalimide (5.76 g, 19.8 mmol) was added to a slurry of NaH (1.59 g of 60% in mineral oil, 39.7 mmol) in dry THF (83 mL) at 0° C. and stirred for 1 h, and then allyl bromide (2.23 mL, 25.8 mmol) was added dropwise. The slurry was stirred for three days, then forward quenched into water (50 mL) and the aqueous phase was extracted with EtO$_2$ (2×35 mL). The combined organics were washed with brine (50 mL), dried over Na$_2$SO$_4$, filtered and concentrated in vacuo. The crude material was purified by column chromatography (SiO$_2$, 1:19, EtOAc:CH$_2$Cl$_2$) to give a white solid 14 (3.77 g, 58%). $R_f$: 0.55 (1:19, EtOAc:hexanes); $^1$H NMR (400 MHz, CDCl$_3$) δ 1.27 (s, 9H), 3.46 (br s, 2H), 3.81 (br s, 2H), 3.87 (br s, 2H), 5.01-5.13 (m, 2H), 5.71-5.77 (m, 1H), 7.70 (br s, 2H), 7.82 (br s, 2H); $^{13}$C NMR (100 MHz, CDCl$_3$) δ 28.2, 44.5, 49.3, 50.2, 80.1, 117.2, 123.4, 132.3, 133.9, 134.2, 155.3, 168.3.

Preparation of 2-(anthracen-9-yl)ethyl(2-(allylamino)ethyl)carbamate (10)

Hydrazine monohydrate (147 μL, 3.03 mmol) was added to a solution of 14 (217 mg, 0.66 mmol) in 2:1 CH$_2$Cl$_2$:EtOH (6 mL) with stirring at 0° C. The reaction was stirred for 18 h, allowing it to warm slowly to room temperature. The white precipitate was then filtered and the filter cake was washed with CH$_2$Cl$_2$ and concentrated in vacuo. The concentrate was diluted with CH$_2$Cl$_2$ and the precipitate was filtered, the cake washed with CH$_2$Cl$_2$ and concentrated in vacuo again to give the corresponding amine tert-butyl allyl(2-aminoethyl)carbamate as a light yellow oil (122 mg, 92%) which was used in the next step without further purification. $R_f$: 0.47 (10:2:88, MeOH:NH$_4$OH:CH$_2$Cl$_2$); $^1$H NMR (500 MHz, CDCl$_3$) δ 1.40 (s, 2H), 1.43 (s, 9H), 2.79 (t, J=5.0 Hz, 2H), 3.22 (br s, 2H), 3.81 (br s, 2H), 5.09-5.12 (m, 2H), 5.74-5.79 (m, 1H); $^{13}$C NMR (100 MHz, CDCl$_3$) δ 28.6, 40.8, 50.1, 79.8, 116.4, 134.3, 156.0.

The amine (188 mg, 0.94 mmol) was added dropwise with stirring to a solution of ClC(O)OCH$_2$CH$_2$ (9-anthracenyl) (303 mg, 1.06 mmol) in dry CH$_2$Cl$_2$ (3.5 mL) at 0° C. After 10 minutes, Et$_3$N (148 μL, 1.06 mmol) was added dropwise to the reaction, causing the solution to darken, and was stirred for 17 h. The reaction was quenched with sat. NH$_4$Cl (5 mL) and the aqueous phase was extracted with CH$_2$Cl$_2$ (5 mL). Combined organics were dried over Na$_2$SO$_4$, filtered and concentrated in vacuo. The crude material was purified by column chromatography (SiO$_2$, 5:1:4, CH$_2$Cl$_2$:hexanes: EtOAc) to give a yellow gum 1.6 (171 mg, 41%). $R_f$: 0.33 (1:19, EtOAc:CH$_2$Cl$_2$); FT-IR 3449, 3058, 2971, 1724, 1514 cm$^{-1}$; $^1$H NMR (400 MHz, CDCl$_3$) δ 1.46 (s, 9H), 3.13 (br s, 2H), 3.36 (br s, 2H), 3.83 (br s, 2H), 3.97 (t, J=8.0 Hz, 2H), 4.43 (br s, 2H), 5.10-5.15 (m, 2H), 5.75-5.81 (m, 1H), 7.44-7.48 (m, 2H), 7.52-7.56 (m, 2H), 8.00 (d, J=8.4 Hz, 2H), 8.35-8.37 (m, 3H); $^{13}$C NMR (100 MHz, CDCl$_3$) δ 28.1, 28.5, 40.5, 46.2, 50.6, 64.6, 80.3, 116.6, 124.4, 125.1, 126.1, 126.8, 129.3, 130.5, 131.7, 134.0, 155.3, 157.0; FT-ICR-MS calcd for C$_{22}$H$_{25}$N$_2$O$_2^+$ [M–t-BuCO$_2$+2H]$^+$ (m/z) 349.1910, found 349.1913.

Example 5

Preparation of Gem-Dimethyl Ester Compound 20

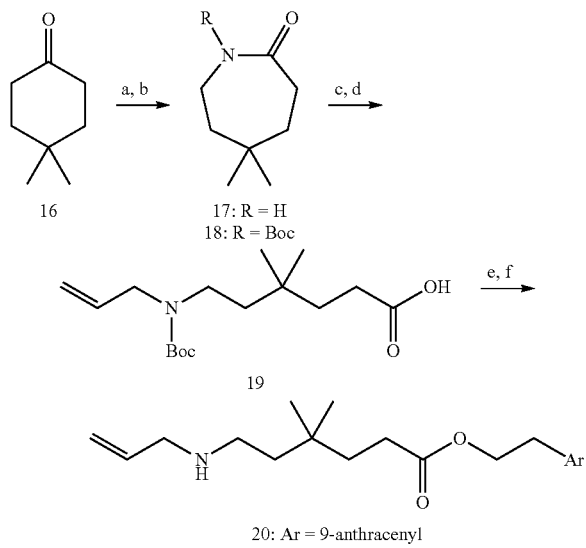

20: Ar = 9-anthracenyl

Conditions: a. H$_2$NOSO$_3$H, HCO$_2$H, reflux, 73%; b. Boc$_2$O, DMAP, THF, reflux, 4 h, 68%; c. LiOH, H$_2$O, THF, 60° C., 96%; d. allyl bromide, NaH, THF, 0° C. to rt, 68%; e. 11, DIC, cat. DMAP, CH$_2$Cl$_2$, 12 h, 87%; f. TFA, CH$_2$Cl$_2$, 0° C., 1 h.

Preparation of 4,4-dimethylcyclohexanone (16)

10% Pd/C (10 mg, 0.0094 mmol) was added to a solution of 4,4-dimethyl-2-cyclohexen-1-one (1.52 g, 12.2 mmol) in hexanes (15 mL). The atmosphere was purged with H$_2$ and sealed with a H$_2$ balloon attached. After 48 h the reaction was filtered through Celite and the filter cake was rinsed with hexanes. The filtrate was concentrated in vacuo to give a crude material 16 (1.29 g white crystals, 83%) which was used in the next step without further purification. $R_f$: 0.46 (1:3, EtOAc:Hexanes); $^1$H NMR (400 MHz, CDCl$_3$) δ 1.09 (s, 6H), 1.66 (t, J=6.0 Hz, 4H), 2.33 (t, J=6.0 Hz, 4H); $^{13}$C NMR (100 MHz, CDCl$_3$) δ 27.7, 30.1, 38.2, 39.3, 212.8.

Preparation of 5,5-dimethylazepan-2-one (17)

A solution of 16 (1.29 g, 10.2 mmol) in formic acid (10 mL) was added dropwise to a solution of hydroxylamine-O-sulfonic acid (1.73 g, 15.3 mmol) in formic acid (7 mL) and allowed to stir at room temperature for 15 min. The reaction flask was then heated to reflux. After 24 h, the reaction solution was cooled to room temperature and quenched with NaOH (40 mL of a 10 N solution). The aqueous mixture was extracted with chloroform (4×20 mL) and the combined organics were washed with water (2×10 mL) and brine (10 mL). The solution was dried over MgSO$_4$, filtered and concentrated in vacuo to give a crude material 17 (1.06 g brown crystals, 73%) which was used in the next step without further purification. $R_f$: 0.13 (EtOAc); $^1$H NMR (400 MHz, CDCl$_3$) δ 0.97 (s, 6H), 1.42-1.44 (m, 2H), 1.48-1.50 (m, 2H), 2.39-2.42 (m, 2H), 3.15 (q, J=5.2 Hz, 2H), 6.50 (br s, 1H); $^{13}$C NMR (100 MHz, CDCl$_3$) δ 29.0, 32.0, 33.0, 36.0, 38.3, 42.4, 179.1.

Preparation of tert-butyl 5,5-dimethyl-2-oxoazepane-1-carboxylate (18)

Di-tert-butyl dicarbonate (1.54 g, 7.01 mmol) and DMAP (856 mg, 7.01 mmol) were added to a solution of 17 (899 mg, 6.37 mmol) in dry THF (16 mL) at rt. After purging the headspace with N$_2$, the reaction was heated to reflux. After 2.5 h the reaction was cooled to room temperature and the volatiles were removed in vacuo and the crude material was purified by column chromatography (SiO$_2$, 1:9 to 3:7, EtOAc:hexanes gradient) to give yellow crystals 18 (1.05 g, 68%). $R_f$: 0.68 (EtOAc); $^1$H NMR (400 MHz, CDCl$_3$) δ 0.94 (s, 6H), 1.46-1.49 (m, 11H), 1.52-1.55 (m, 2H), 2.54-2.57 (m, 2H), 3.67-3.70 (m, 2H); $^{13}$C NMR (100 MHz, CDCl$_3$) δ 28.2, 28.8, 32.2, 35.2, 36.5, 41.8, 41.9, 83.0, 153.0, 175.8.

Preparation of 6-(allyl(tert-butoxycarbonyl)amino)-4,4-dimethylhexanoic acid (19)

Lithium hydroxide monohydrate (340 mg, 8.10 mmol) was added to a solution of 18 (888 mg, 3.68 mmol) in 2:1 THF:H$_2$O (18 mL) and the reaction was heated to 60° C. After 4 h the reaction was cooled to room temperature and partitioned between Et$_2$O and H$_2$O and the organic layer separated. The aqueous phase was acidified to pH ~4 with 10% HCl and extracted with EtOAc (3×15 mL). The combined organics were washed with brine (15 mL), dried over Na$_2$SO$_4$, filtered and concentrated in vacuo to give the corresponding amino acid 6-((tert-butoxycarbonyl)amino)-4,4-dimethylhexanoic acid as a yellow crystal (912 mg, 96%) which was used in the next step without further purification. $R_f$: 0.29 (1:1, EtOAc:Hexanes with 0.5% AcOH); $^1$H NMR (400 MHz, CDCl$_3$) δ 1.37-1.43 (m, 11H), 1.58 (t, J=8.4 Hz, 2H), 2.30 (t, J=8.4 Hz, 2H), 3.11 (br s, 2H), 4.49 (br s, 1H); $^{13}$C NMR (100 MHz, CDCl$_3$) δ 26.9, 28.6, 29.5, 32.1, 36.6, 36.9, 41.6, 79.5, 156.2, 179.7.

The crude amino acid (912 mg, 3.52 mmol) was added to a slurry of 60% NaH (703 mg, 17.6 mmol) in dry THF (18 mL) at 0° C. After one-hour of stirring, allyl bromide (912 µL, 10.5 mmol) was added dropwise. After 24 h, the reaction mixture was cooled to 0° C. and quenched with water until the reaction became transparent. The reaction was acidified to pH ~3 with HCl (1 M solution) and the layers were separated. The aqueous phase was extracted with EtOAc (3×10 mL) and the combined organics washed with brine (15 mL), dried over $Na_2SO_4$, filtered and concentrated in vacuo. The crude material was purified by column chromatography ($SiO_2$, 1:1, EtOAc:hexanes with 0.5% AcOH) to give a light yellow oil 19 (712 mg, 68%). $R_f$: 0.43 (1:1, EtOAc:hexanes with 0.5% AcOH); $^1$H NMR (400 MHz, $CDCl_3$) δ 0.88 (s, 6H), 1.39-1.44 (m, 11H), 1.56 (t, J=8.0 Hz, 2H), 2.31 (t, J=8.2 Hz, 2H), 3.14 (br s, 2H), 3.80 (br s, 2H), 5.11 (d, J=11.6 Hz, 2H), 5.71-5.81 (m, 1H); $^{13}$C NMR (100 MHz, $CDCl_3$) δ 26.8, 28.7, 29.5, 32.0, 36.4, 39.5, 42.8, 49.6, 79.8, 116.8, 134.6, 155.6, 180.2.

Preparation of 2-(anthracen-9-yl)ethyl 6-(allylamino)-4,4-dimethylhexanoate (20)

19 (370 mg, 1.24 mmol) and 11 (249 mg, 1.12 mmol) were dissolved in dry $CH_2Cl_2$ (10 mL) with stirring. DIC (264 µL, 1.69 mmol) was added to the reaction solution followed by cat. DMAP. After 16 h, the white solids were filtered out and the filter cake was washed with $CH_2Cl_2$. The filtrate was condensed in vacuo and the crude material was purified by column chromatography ($SiO_2$, 0:100 to 1:19, EtOAc:$CH_2Cl_2$ gradient) to give the corresponding ester 2-(anthracen-9-yl)ethyl 6-(allyl(tert-butoxycarbonyl)amino)-4,4-dimethylhexanoate as a yellow oil (494 mg, 87%). $R_f$: 0.58 (1:19, EtOAc:$CH_2Cl_2$); FT-IR 3058, 2963, 1728, 1684 cm$^{-1}$; $^1$H NMR (400 MHz, $CDCl_3$) δ 0.87 (s, 6H), 1.39 (br s, 2H), 1.46 (s, 9H), 1.51 (t, J=8.4 Hz, 2H), 2.28 (t, J=8.2 Hz, 2H), 3.12 (br s, 2H), 3.81 (br s, 2H), 3.98 (t, J=7.8 Hz, 2H), 4.48 (t, J=7.8 Hz, 2H), 5.12 (d, J=11.6 Hz, 2H), 5.73-5.82 (m, 1H), 7.46-7.49 (m, 2H), 7.53-7.57 (m, 2H), 8.02 (d, J=8.4 Hz, 2H), 8.34 (d, J=9.2 Hz, 2H), 8.39 (s, 1H); $^{13}$C NMR (100 MHz, $CDCl_3$) δ 26.8, 27.5, 28.7, 29.8, 32.0, 36.6, 39.2, 42.8, 49.6, 53.6, 64.3, 79.6, 116.6, 124.3, 125.2, 126.2, 127.0, 129.5, 130.5, 131.7, 134.7, 155.5, 174.5; FT-ICR-MS calcd for $C_{27}H_{34}NO_2^+$ [M-t-$BuCO_2$+2H]$^+$ (m/z) 404.2584, found 404.2588.

Example 6

Preparation of Gem-Dimethyl Carbonate Compound 23

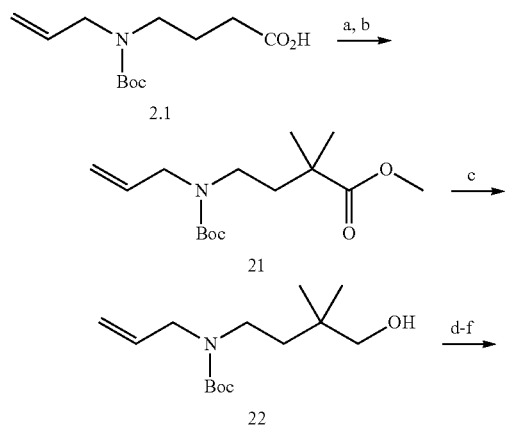

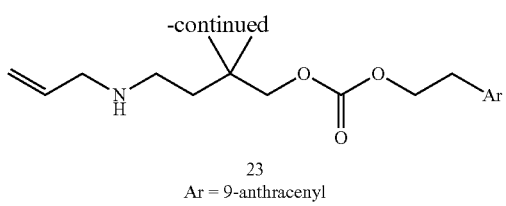

23
Ar = 9-anthracenyl $^a$Conditions: a. MeOH, DIC, cat. DMAP, rt, 80%; b. LiHMDS, MeI, THF, -78° C. to rt, 67%; c. LiBH$_4$, THF, 0° C. to rt, 73%; d. (imid)$_2$C═O, (i-Pr)$_2$NEt, CH$_2$Cl$_2$, 0° C. to rt, 92%; e. 2-(9-anthracenyl)ethanol, NaH, THF, -5° C. to rt, 48%; f. TFA, CH$_2$Cl$_2$, 0° C., 1 h, 100%.

Preparation of Methyl 4-(allyl(tert-butoxycarbonyl)amino)-2,2-dimethylbutanoate (21)

DIC (837 µL, 5.34 mmol), followed by cat. DMAP, was added to a solution of S2.1 (631 mg, 2.59 mmol) and dry MeOH (173 µL, 4.28 mmol) in dry $CH_2Cl_2$ (32 mL) at rt. After 12 h the white precipitate was filtered out and the filter cake was washed with $CH_2Cl_2$, and the filtrate was concentrated in vacuo. The crude material was purified by column chromatography ($SiO_2$, 1:1:8, EtOAc:THF:hexanes) to give the ester methyl 4-(allyl(tert-butoxycarbonyl)amino)butanoate as a pale yellow solid (532 mg, 80%). $R_f$: 0.65 (1:1:8, EtOAc:THF:hexanes); $^1$H NMR (400 MHz, $CDCl_3$) δ 1.44 (s, 9H), 1.82 (dt, J=7.0 Hz, 2H), 2.30 (t, J=7.4 Hz, 2H), 3.20 (br s, 2H), 3.65 (s, 3H), 3.79 (br s, 2H), 5.10 (d, J=12.8 Hz, 2H), 5.72-5.80 (m, 1H); $^{13}$C NMR (100 MHz, $CDCl_3$) δ 23.7, 28.6, 31.4, 45.9, 49.7, 51.8, 79.8, 116.7, 134.3, 155.7, 173.8.

The methyl ester (532 mg, 2.06 mmol) was dissolved in dry THF (10 mL) and cooled to −78° C. with stirring. A solution of Lithium bis(trimethylsilyl)amide (LiHMDS) in THF (6.20 mL of 1 M solution, 6.20 mmol) was added dropwise to the reaction solution and allowed to stir for 1 h. Methyl iodide (772 µL, 12.4 mmol) was then added dropwise and the reaction was stirred overnight, while slowly coming to rt. After 22 h, the reaction was cooled to 0° C. and quenched with water (5 mL), followed by 1 M HCl (5 mL). The phases were separated and the aqueous phase was extracted with $Et_2O$ (3×15 mL). The combined organics were washed with $NaHCO_3$ (10 mL) and brine (10 mL) and were then dried over $Na_2SO_4$, filtered and concentrated in vacuo. The crude material was purified by column chromatography ($SiO_2$, 1:4 EtOAc:hexanes) to give a pale yellow solid 21 (397 mg, 67%). $R_f$: 0.48 (1:4, EtOAc:hexanes); $^1$H NMR (400 MHz, $CDCl_3$) δ 1.18 (s, 6H), 1.44 (s, 9H), 1.74 (br s, 2H), 3.11 (br s, 2H), 3.65 (s, 3H), 3.79 (br s, 2H), 5.10 (d, J=10.8 Hz, 2H), 5.70-5.79 (m, 1H); $^{13}$C NMR (100 MHz, $CDCl_3$) δ 25.3, 28.6, 38.1, 41.1, 43.1, 49.4, 51.9, 79.7, 116.1, 134.2, 155.5, 178.0.

Preparation of tert-butyl allyl(4-hydroxy-3,3-dimethylbutyl)carbamate (22)

$LiBH_4$ (45 mg, 2.08 mmol) was added to a solution of 21 (265 mg, 0.93 mmol) in dry THF (21 mL) at 0° C. After 5 minutes of stirring the reaction was warmed to room temperature and stirred overnight. The reaction was then carefully quenched with $NH_4Cl$ (25 mL) and extracted with $Et_2O$ (3×10 mL). The combined organics were washed with brine (15 mL), dried over $Na_2SO_4$ and concentrated in vacuo. The crude material was purified by column chromatography ($SiO_2$, 1:1 EtOAc:hexanes) to give a colorless oil 22 (175 mg, 73%). $R_f$: 0.47 (1:1, EtOAc:hexanes); $^1$H NMR (400 MHz, CDCl$_3$) δ 0.86 (s, 6H), 1.43-1.49 (m, 11H), 2.89 (br s, 1H), 3.13-3.17 (m, 2H), 3.32 (s, 2H), 3.78 (br s, 2H), 5.09-5.13 (m, 2H), 5.71-5.81 (m, 1H); $^{13}$C NMR (100 MHz, CDCl$_3$) δ 24.4, 28.6, 34.7, 36.5, 42.9, 50.4, 70.8, 79.8, 116.4, 134.6, 155.8.

Preparation of 4-(allylamino)-2,2-dimethylbutyl(2-(anthracen-9-yl)ethyl) carbonate (23)

N,N-Diisopropylethylamine (304 μL, 1.74 mmol) was added to a solution of 22 (251 mg, 0.98 mmol) in dry CH$_2$Cl$_2$ (25 mL) at 0° C. 1,1'-Carbonyldiimidazole (283 mg, 1.74 mmol) was then added to the solution and it was warmed to rt. After 24 h, the reaction was washed with water (2×10 mL), brine (10 mL), was dried over Na$_2$SO$_4$, filtered and concentrated in vacuo. The crude material was purified by column chromatography (SiO$_2$, EtOAc) to give the imidazole carbamate as a colorless oil (316 mg, 92%). R$_f$: 0.61 (EtOAc); $^1$H NMR (400 MHz, CDCl$_3$) δ 1.01 (s, 6H), 1.42 (s, 9H), 1.56 (t, J=7.8 Hz, 2H), 3.21 (br s, 2H), 3.76 (br s, 2H), 4.12 (s, 2H), 5.07-5.09 (m, 2H), 5.70-5.79 (m, 1H), 7.07 (s, 1H), 7.42 (s, 1H), 8.13 (s, 1H); $^{13}$C NMR (100 MHz, CDCl$_3$) δ 24.2, 28.6, 33.7, 36.7, 42.5, 50.0, 75.9, 79.8, 116.4, 117.2, 130.9, 134.5, 137.2, 148.9, 155.4.

A solution of 2-(9-anthracenyl)ethanol (191 mg, 0.86 mmol) in dry THF (1 mL) was added dropwise to a slurry of NaH (103 mg of 60% in mineral oil, 2.57 mmol) in dry THF (5 mL) at −5° C. and stirred for 30 minutes. A solution of the imidazole carbamate (316 mg, 0.90 mmol) in dry THF (1 mL) was then added dropwise to the reaction mixture. The reaction was stirred overnight, then the mixture was filtered through Celite and the filter cake was washed with Et$_2$O. The filtrate was washed with water (2×10 mL) and the combined aqueous layers were extracted with Et$_2$O (3×10 mL). The combined organic phases were washed with brine, dried over Na$_2$SO$_4$, filtered and concentrated in vacuo. The crude material was purified by column chromatography (SiO$_2$, 1:19 EtOAc:CH$_2$Cl$_2$) to give 23 as a yellow oil (207 mg, 48%). R$_f$: 0.64 (1:19, EtOAc:CH$_2$Cl$_2$); FT-IR: 3008, 2974, 1743, 1685, 1256 cm$^{-1}$; $^1$H NMR (400 MHz, CDCl$_3$) δ 0.98 (s, 6H), 1.46 (s, 9H), 1.53 (t, J=7.8 Hz, 2H), 3.19 (br s, 2H), 3.77-3.82 (m, 2H), 3.90 (s, 2H), 4.05 (t, J=8.0 Hz, 2H), 4.50 (t, J=8.4 Hz, 2H), 5.10-5.13 (m, 2H), 5.74-5.80 (m, 1H), 7.45-7.49 (m, 2H), 7.53-7.57 (m, 2H), 8.01 (d, J=8.4 Hz, 2H), 8.34 (d, J=9.2 Hz, 2H), 8.40 (s, 1H); $^{13}$C NMR (100 MHz, CDCl$_3$) δ 24.1, 27.6, 28.7, 33.5, 37.1, 42.5, 49.7, 67.3, 76.2, 79.8, 116.2, 124.1, 125.2, 126.4, 127.2, 128.3, 129.5, 130.5, 131.7, 134.5, 155.5, 155.7; FT-ICR-MS calcd for C$_{26}$H$_{32}$NO$_3^+$ [M−t-BuCO$_2$+2H]$^+$ (m/z) 406.2377, found 406.2379.

Example 7

Alternative Preparation of Compound 23

Compound 23 can also be prepared according to the synthetic sequence outlined below.

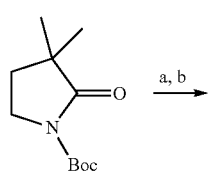

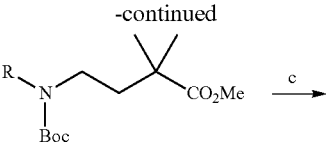
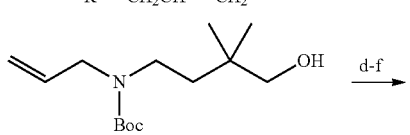
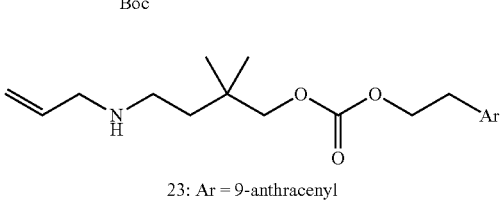

23: Ar = 9-anthracenyl

Conditions: a. NaOMe, MeOH, 0° C.; b. allyl bromide, NaH, THF, 0° C. to rt; c. LiBH$_4$, THF, rt; d. (imid)$_2$C═O, (i-Pr)$_2$NEt, CH$_2$Cl$_2$, 0° C. to rt; e. 2-(9-anthracenyl)ethanol, KOH, toluene, 60° C.; f. TFA, CH$_2$Cl$_2$, 0° C., 1 h.

Example 8

Heat Induced Release of Drug Surrogates (e.g., Alcohol 11 and 12) from Linkers

General Procedure

Figure 12:
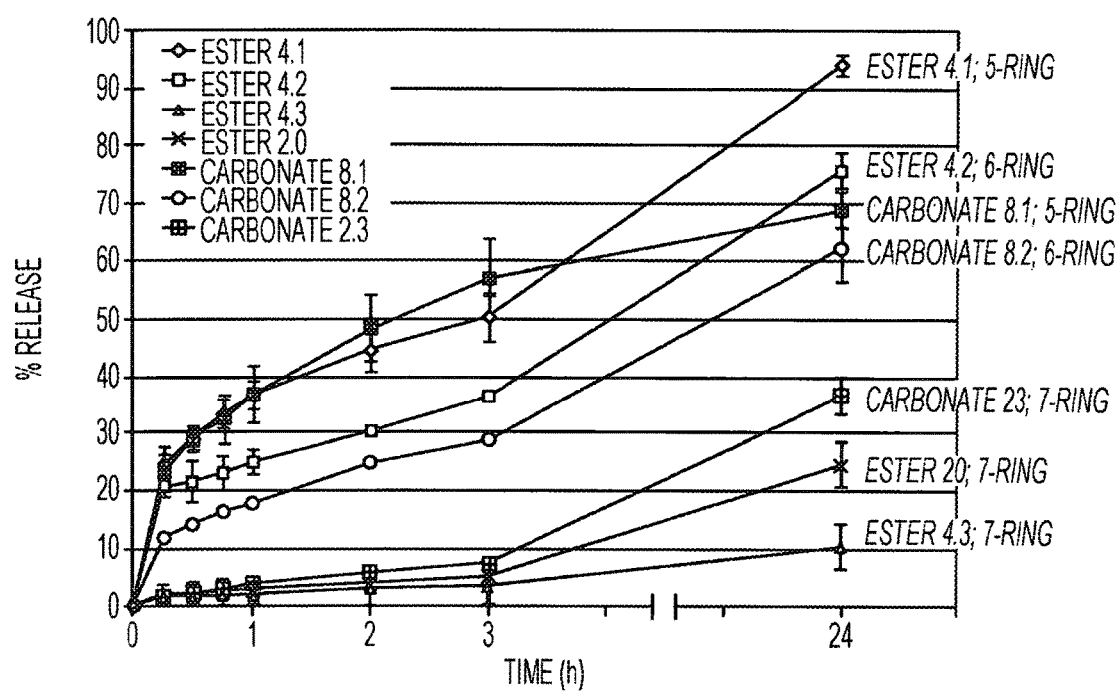
FIG. 12 illustrates the heat-induced release of alcohol 11. The substrates were heated as methanol solutions (ca. 0.01 M) at 55° C. for the indicated times. Shown are the standard deviations from the mean (n=3).
Figure 13:
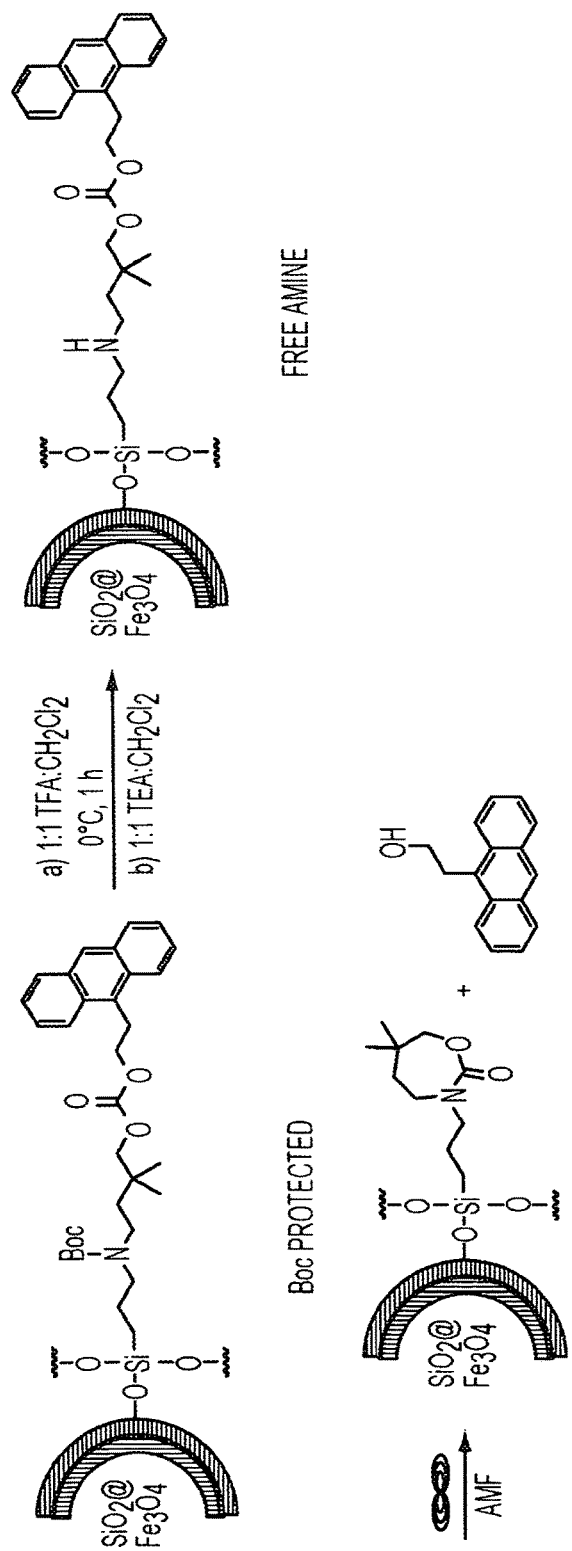
FIG. 13 illustrates the general process for the release of the drug surrogate from the nanoparticle. First, the Boc protecting group was removed under acidic conditions and basified to afford the secondary amine. Then, the nanoparticles were exposed to an AMF that caused the nanoparticles to heat, thus providing the energy needed to induce the intramolecular cyclization and release the drug surrogate.

Methanol (MeOH) was used as a solvent to provide a protic solvent capable of hydrogen bonding. The amine-containing linker compounds, formed on Boc-deprotection with basic work-up (compounds 4.1-3, 8.1-2, 9, 10), were diluted with MeOH (2 mL, ~0.01 M). An aliquot was removed to serve as a room temperature control. Heat was applied to the MeOH solutions using an oil bath. The temperature was set at 55° C., and the solutions were heated for a total of 24 h. Aliquots were taken at t=0.25, 0.50, 0.75, 1, 2, 3, and 24 h into the reaction. On sampling, the aliquots were, immediately stored at −5° C. On completion of the experiment, the samples were warmed to room temperature, filtered and dried under reduced pressure (3.5 h duration) and then returned to −5° C. Each sample was then removed individually from the freezer and diluted with 400 μL CH$_2$Cl$_2$ before injecting 50 μL into an HPLC fitted with a normal phase silica column (Waters Nova-Pak HR Silica, 6 μm, 60 Å, 3.9×300 mm prep column; 1% MeOH in CH$_2$Cl$_2$ with 0.1% Et$_3$N). HPLC analysis enabled quantification of released 11 or 12. Schemes 3 and 4 depict the intramolecular cyclization processes to release the drug surrogate (e.g., 11 or 12). Table 1 shows the percent release of alcohol 11 or amine 12 upon heating. FIG. 12 graphically illustrates the heat-induced release of alcohol 11 (Table 1). The substrates were heated as methanol solutions (ca. 0.01 M) at 55° C. for the indicated times as described above.

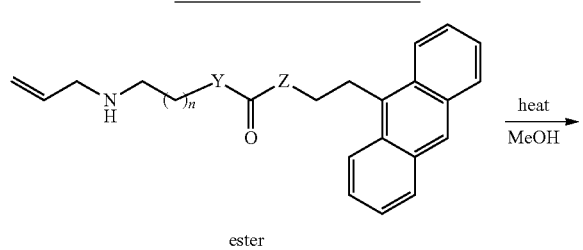

Scheme 3. Evaluation of linkers.

ester
4.1: Y = CH₂, Z = O, n = 1 (to 5-ring)
4.2: Y = CH₂, Z = O, n = 2 (to 6-ring)
4.3: Y = CH₂, Z = O, n = 3 (to 7-ring)
carbonate
8.1: Y, Z = O, n = 1 (to 5-ring)
8.2: Y, Z = O, n = 2 (to 6-ring)
amide
9: Y = CH₂, Z = NH, n = 1 (to 5-ring)
carbamate
10: Y = NH, Z = O, n = 1 (to 5-ring)

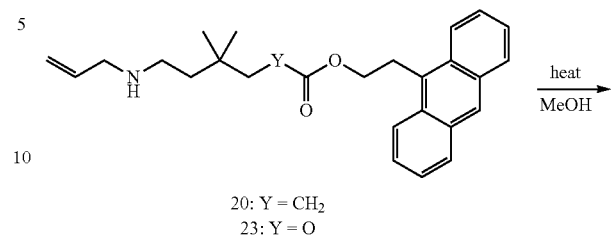

Scheme 4. Evaluation of linkers

20: Y = CH₂
23: Y = O

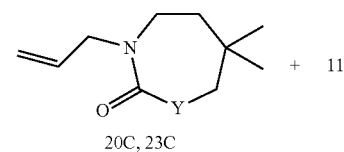

20C, 23C

TABLE 1

Heat-induced release of 11 or 12 (Schemes 3 and 4). Shown are the standard deviation from the mean (n = 3).

| Entry | Substrate (ring size) | % release after heating (55° C.) at time (h) | | | | | | | % release at rt, 3.5 h |
|---|---|---|---|---|---|---|---|---|---|
| | | 0.25 | 0.5 | 0.75 | 1 | 2 | 3 | 24 h | |
| 1 | ester 4.1 (5) | 24.6 ± 3.1 | 29.2 ± 1.7 | 33.4 ± 2.5 | 36.6 ± 2.6 | 44.4 ± 3.7 | 50.2 ± 4.2 | 94.0 ± 1.8 | 20.2 ± 3.1 |
| 2 | ester 4.2 (6) | 20.9 ± 1.9 | 21.6 ± 3.5 | 23.0 ± 3.0 | 25.0 ± 2.1 | 30.5 ± 1.3 | 36.5 ± 1.2 | 75.7 ± 3.2 | 17.0 ± 4.5 |
| 3 | ester 4.3 (7) | 2.1 ± 1.6 | 1.8 ± 1.9 | 2.1 ± 2.2 | 2.1 ± 1.8 | 3.1 ± 2.9 | 3.6 ± 3.0 | 10.4 ± 3.8 | 1.7 ± 2.0 |
| 4 | gem-ester 20 (7) | 2.0 ± 0.1 | 2.2 ± 0.1 | 2.7 ± 0.1 | 3.3 ± 0.4 | 4.1 ± 0.3 | 5.2 ± 0.8 | 24.7 ± 3.9 | 1.8 ± 0.2 |
| 5 | carbonate 8.1 (5) | 23.5 ± 1.9 | 28.9 ± 1.7 | 32.4 ± 4.0 | 36.7 ± 4.8 | 48.3 ± 5.7 | 57.0 ± 6.9 | 68.9 ± 3.0 | 18.8 ± 2.3 |
| 6 | carbonate 8.2 (6) | 12.0 ± 0.8 | 14.1 ± 0.7 | 16.4 ± 1.0 | 18.0 ± 0.7 | 24.8 ± 1.1 | 29.0 ± 1.0 | 62.1 ± 5.6 | 9.6 ± 1.1 |
| 7 | gem-carbonate 23 (7) | 1.8 ± 0.4 | 2.3 ± 0.5 | 2.9 ± 0.1 | 4.0 ± 0.3 | 5.7 ± 1.0 | 7.6 ± 0.3 | 36.6 ± 0.3 | 0.7 ± 0.1 |
| 8 | amide 9 (5) | | | | no reaction | | | | |
| 9 | carbamate 10 (5) | | | | no reaction | | | | |

-continued

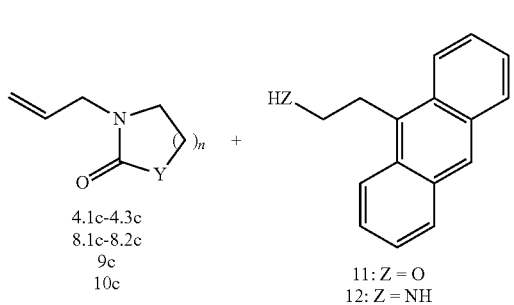

4.1c-4.3c
8.1c-8.2c
9c
10c

11: Z = O
12: Z = NH

Example 9

Preparation and Analysis of Linker Covalently Attached to SiO₂ Coated Fe₃O₄ Nanoparticles Attachment of SiO₂ Coating to Fe₃O₄ Nanoparticles.

SiO₂ coated iron oxide nanoparticles (i.e., Fe₃O₄@SiO₂) were prepared using the Stober process (Stober, W.; et al., *J. Colloid Interface Sci.* 1968, 26, 62-69) that was modified for the preparation silica-coated nanoparticles (Pinho, S.; et al., *ACS Nano* 2010, 4, 5339-5349).

Preparation of Compound 24

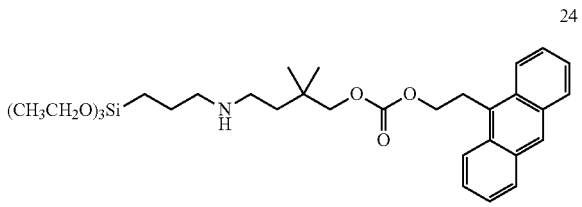

Compound 23 (150 mg, 0.30 mmol) was placed into a pressure tube with a stir-bar and the headspace was purged with nitrogen. Catalytic $PtO_2$ (Sabourault, N., et al., *Organic Letters* 2002, 4, 2117-2119) was then added, followed by triethoxysilane (55 μL, 0.30 mmol). The headspace was purged with nitrogen and the pressure tube was sealed and heated to 85° C. for two days. The reaction was then cooled to room temperature and the solution was filtered through Celite and the filter cake was washed with dry $CH_2Cl_2$. The filtrate was concentrated in vacuo to give crude 24 as a brown oil which was loaded onto the NPs without further purification.

Covalent Attachment of Linker to $Fe_3O_4@SiO_2$.

The $Fe_3O_4@SiO_2$ nanoparticles (100 mg) were suspended in a 19:1 solution of $EtOH:H_2O$ (20 mL) with sonication and were then vigorously stirred by a mechanical stirrer. A solution of the triethoxysilane-functionalized linker 24 (0.4 mmol) in EtOH (4 mL) was added dropwise to the suspended nanoparticles. The suspension was heated to 65° C. and stirred for 24 h. The nanoparticles were then collected by magnetic separation and decantation of the supernatant. The nanoparticles were then heated at 85° C. under vacuum for 2 h. The nanoparticles were then washed five-times with EtOH followed by magnetic separation and decantation to remove any unbound linker and dried under vacuum to afford the functionalized nanoparticles. Loading was verified by FTIR and the loading density was determined by TGA.

Boc Deprotection on Functionalized Nanoparticles.

The Boc protecting group was cleaved by adding $CH_2Cl_2$ (1 mL) to the protected nanoparticles (10 mg) and cooling the mixture to 0° C. TFA (1 mL) was then added and the mixture was vortexed every five minutes for 0.5 h. The nanoparticles were then collected by magnetic separation and decantation of the acidic solvent, followed by two washes with $CH_2Cl_2$. The acidic ammonium functionalized nanoparticles were then washed three times with a basic solution of 1:1 $TEA:CH_2Cl_2$ followed by three washes with $CH_2Cl_2$. The nanoparticles were dried under vacuum to afford the free amine functionalized nanoparticles.

AMF Irradiation of NPs, and Fluorescent and MALDI-TOF Analyses.

5-10 mg of nanoparticles were placed into a quartz cuvette and suspended in a 2:1 PBS:MeCN solution (75 μL) and the AMF was applied using an Ambrell EasyHeat L1 at 595 Amps with a five-turn coil in 5 minute pulses for a total of 30 minutes of AMF exposure. After each 5 minute burst the nanoparticles were removed from the solution by magnetic separation and the fluorescence of the supernatant was measured using a Molecular Devices SpectraMax M5 ($\lambda_{ex}$=360/$\lambda_{em}$=413) to determine the amount of the probe that was released. The supernatant was analyzed on a Voyager DE-Pro MALDI-TOF instrument (PE Biosystems) and the spectra were acquired in positive reflectron mode to verify that only the desired probe was being released from the nanoparticle. The MALDI sample was prepared by mixing the supernatant 1:1 with a 3:7 MeCN:0.1% TFA in water solution of 2,5-dihydroxybenzoic acid. 1 μL drop was placed on a ground steel MALDI plate and dried for analysis. The alcohol probe was the only peak observed.

Effect of Heat without AMF Radiation on NPs.

Figure 14:
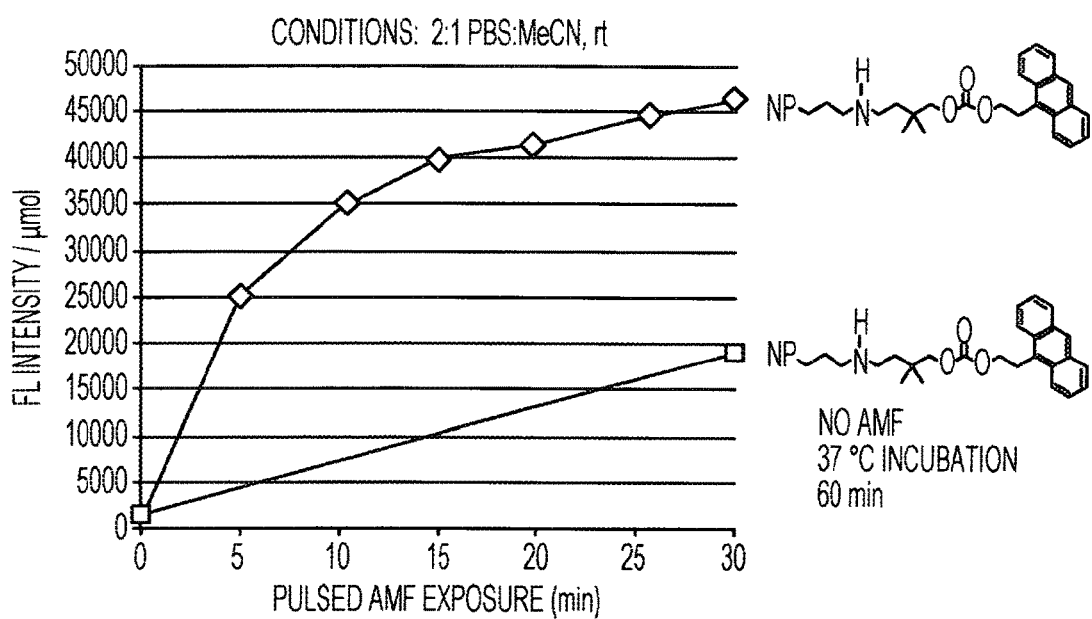
FIG. 14 illustrates the AMF-induced release of the drug surrogate (top line) and release of drug surrogate at 37° C. without AMF (bottom line).
Figure 15:
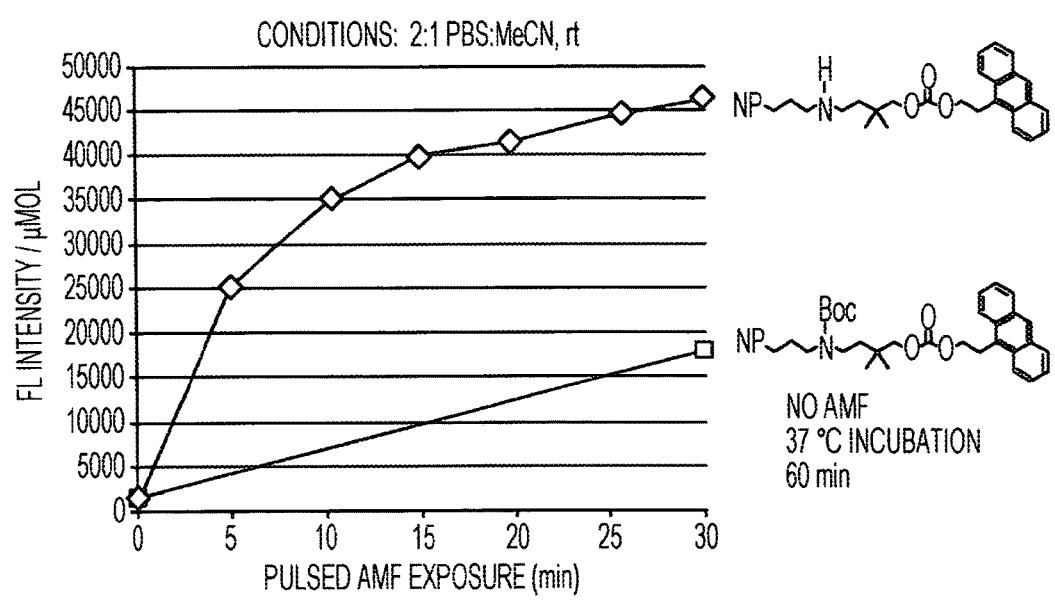
FIG. 15 illustrates AMF-induced release of the drug surrogate (top line) and release of drug surrogate from Boc-protected linker at 37° C. without AMF (bottom).
Figure 16A:
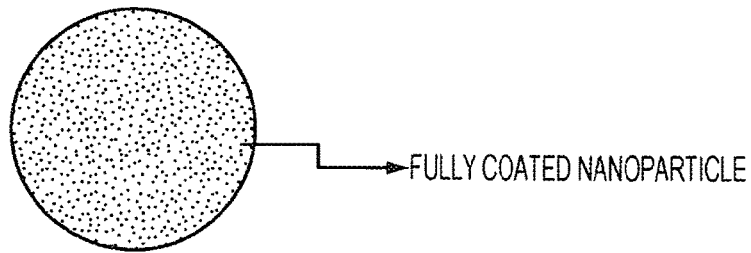
FIG. 16A illustrates a fully coated magnetic nanoparticle.
Figure 16B:
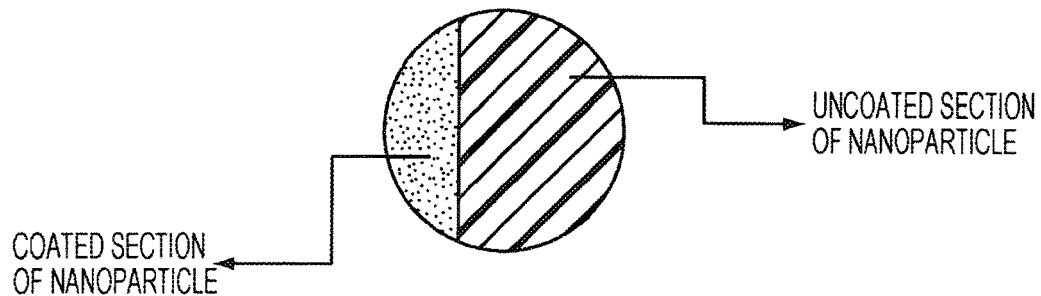
FIG. 16B illustrates a partially coated magnetic nanoparticle.
Figure 16C:
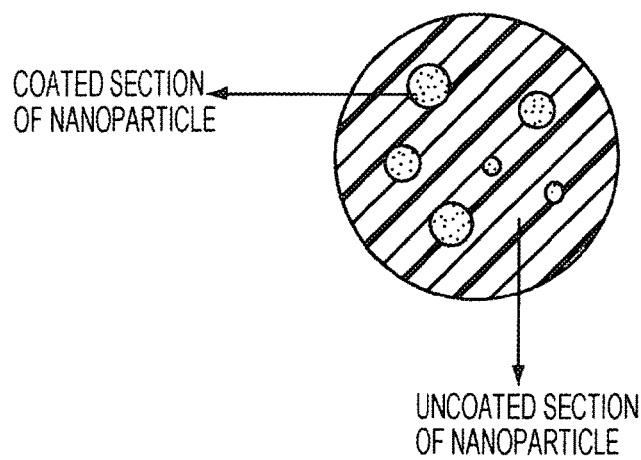
FIG. 16C illustrates a partially coated magnetic nanoparticle wherein the coating is non-contiguous (for example spotted).

FIGS. 14 and 15 demonstrate that the release from the nanoparticle without AMF is a result of hydrolysis and not due to premature cyclization. The intramolecular cyclization only occurs when an AMF is applied. This is shown by the similar fluorescence results attained from linkers with and without the Boc protecting group that prevents intramolecular cyclization.

Example 10

Preparation of Therapeutic Magnetic Nanoparticles with Therapeutic Agents Comprising a Ketone or Aldehyde Group

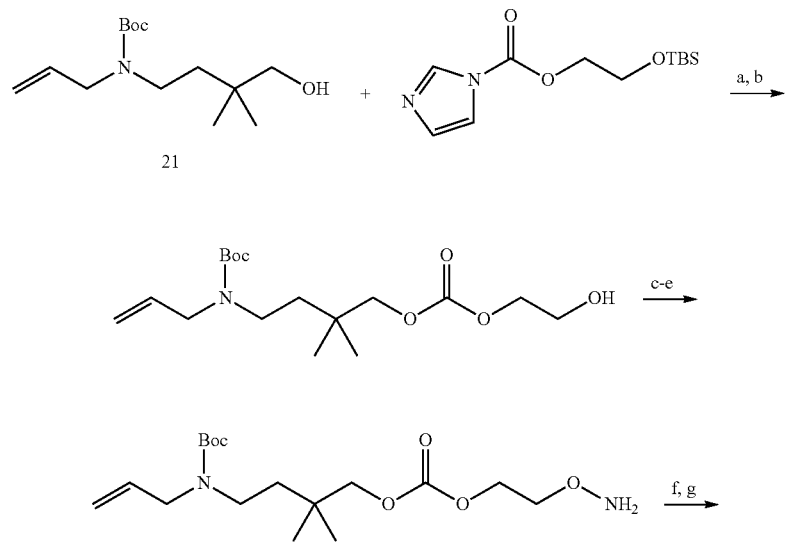

-continued

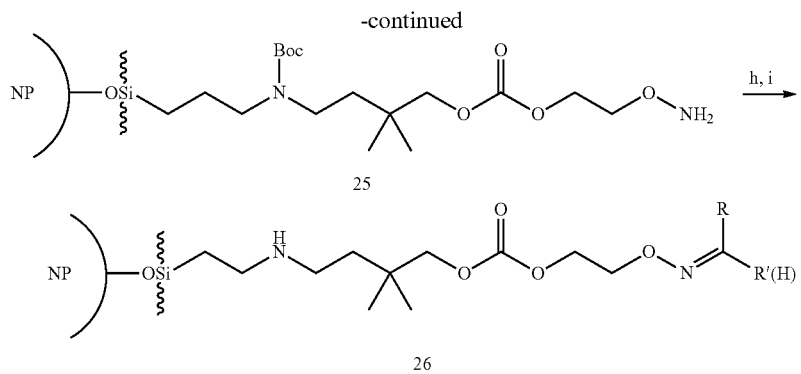

Conditions: a. DBU, MeCN, rt; b. TBAF, THF, 0° C.; c. MsCl, Et₃N, CH₂Cl₂, 0° C.;
d. N-hydroxyphthalimide, K₂CO₃, DMSO, 80° C.; e. hydrazine monohydrate, EtOH, rt;
f. (EtO)₃SiH, cat. PtO₂, 85° C.; g. NPs, EtOH, H₂O, 65° C.; h. RC(O)R' or RC(O)(H),
EtOH, rt; i. 1:1 TFA:CH₂Cl₂, 0° C. (RC(O)R' and RC(O)(H) include therapeutic agents
containing an aldehyde or a ketone)

Therapeutic magnetic nanoparticles with therapeutic agents comprising a ketone or aldehyde group can be readily prepared according the scheme directly above using chemical steps analogous to those described herein.

The ketone or aldehyde of the therapeutic agent has been converted to a prodrug of the therapeutic agent as shown in formula IIa which prodrug is attached to the linker. Accordingly, one embodiment provides a therapeutic agent which is a prodrug of the therapeutic agent and is represented by formula IIa:

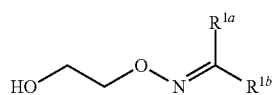

IIa wherein $R^{1a}$ and $R^{1b}$ together with the remainder of formula IIa are the prodrug of the therapeutic agent. It is to be understood that the prodrug of formula IIa represents a therapeutic agent of formula IIb (wherein $R^{1a}$ and $R^{1b}$ and the carbonyl to which they are attached represent a therapeutic agent):

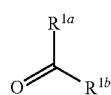

IIb wherein the ketone or aldehyde of the therapeutic agent of formula IIb has been condensed with the aminooxy moiety of HO—(CH₂)₂—O—NH₂ to arrive at the prodrug of the therapeutic agent of formula IIa.

In one embodiment a residue of a therapeutic agent (—Z—D¹) is a represented by formula IIc:

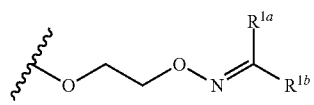

IIc wherein $R^{1a}$ and $R^{1b}$ together with the remainder of formula IIc the residue of the therapeutic agent (—Z—D¹).

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A therapeutic magnetic nanoparticle, or a salt thereof, comprising a magnetic nanoparticle covalently bonded to one or more -L-D groups wherein D is a residue of a therapeutic agent and L is a linker capable of undergoing an intramolecular cyclization;
wherein -L-D has the following formula I:

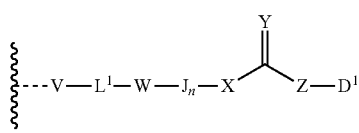

wherein;
V is —S—, the magnetic nanoparticle is coated in gold, and the dashed line represents a covalent bond between —S— and the magnetic nanoparticle coated in gold;
$L^1$ is $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene, wherein $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene are optionally substituted with one or more halogen;
each J is $C(R^b)_2$ wherein one $C(R^b)_2$ of J may be replaced by —O—, —S— or —N($R^e$)—;
(a) W is NH, X is $CR^cR^d$, and n is an integer from 0-5; or
(b) W is NH, X is O, $NR^e$ or S, and n is an integer from 1-5; or
(c) W is

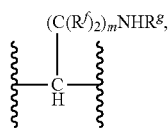

X is $CR^cR^d$, O, $NR^e$, S or absent, m is an integer from 0-5 and n is an integer from 0-5, wherein the sum of m and n is 0-5;
Y is O or S;
Z-$D^1$ is a residue of a therapeutic agent wherein Z is O, $NR^h$ or S;
each $R^b$ is independently selected from H and $(C_1-C_3)$ alkyl; or two $R^b$ groups together with the carbon to which they are attached form a $(C_3-C_7)$carbocycle;
each $R^c$ is independently selected from H and $(C_1-C_6)$ alkyl, and each $R^d$ is independently selected from H and $(C_1-C_6)$alkyl; or an $R^c$ group and an $R^d$ group together with the carbon to which they are attached form a $(C_3-C_7)$carbocycle;
each $R^e$ is independently selected from H and $(C_1-C_6)$ alkyl;
each $R^f$ is independently selected from H and $(C_1-C_6)$ alkyl, or two $R^f$ groups together with the carbon to which they are attached form a $(C_3-C_7)$carbocycle,
$R^g$ is selected from H and $(C_1-C_6)$alkyl, and
$R^h$ is selected from H and $(C_1-C_6)$alkyl.

2. The therapeutic magnetic nanoparticle of claim 1, wherein the linker capable of undergoing an intramolecular cyclization is suitable to release the therapeutic agent from the linker upon intramolecular cyclization.

3. The therapeutic magnetic nanoparticle of claim 1, wherein the linker capable of undergoing an intramolecular cyclization can form a 3-8 membered heterocyclic ring upon cyclization.

4. The therapeutic magnetic nanoparticle of claim 3, wherein the 3-8 membered ring comprises a group selected from an amide, carbamate, urea, carbamothioate, thioamide, thiocarbamate, thiourea and carbamodithioate.

5. The therapeutic magnetic nanoparticle of claim 1, wherein the magnetic nanoparticle comprises iron.

6. The therapeutic magnetic nanoparticle of claim 1, wherein $L^1$ is $(C_1-C_6)$alkylene optionally substituted with one or more halogen.

7. The therapeutic magnetic nanoparticle of claim 1, wherein:
(a) W is NH, X is $CR^cR^d$, and n is an integer from 0-5; or
(b) W is NH, X is O, $NR^e$ or S, and n is an integer from 1-5.

8. The therapeutic magnetic nanoparticle of claim 1, wherein Y is O.

9. The therapeutic magnetic nanoparticle of claim 1, wherein the portion of formula I as shown in the formula below:

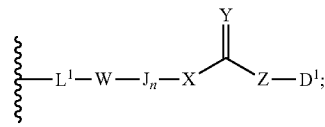

is selected from;

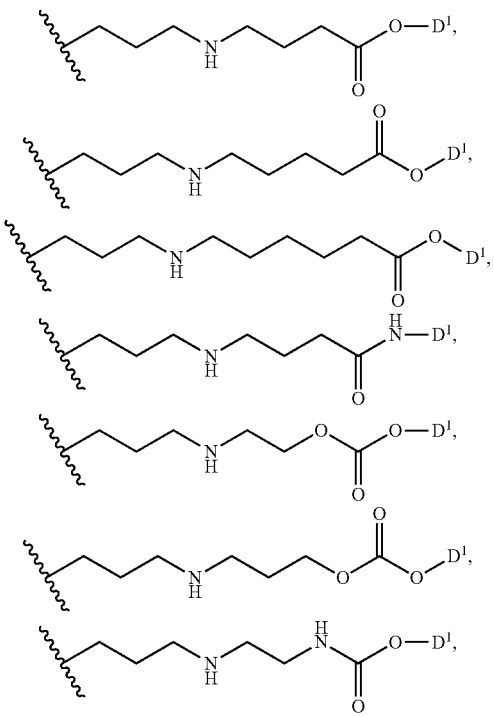

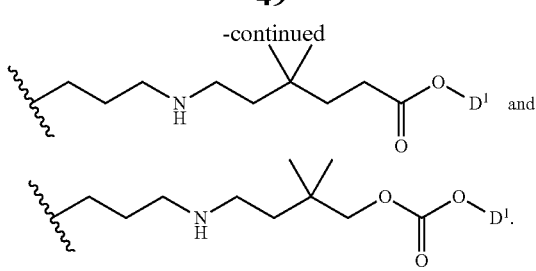 and

10. The therapeutic magnetic nanoparticle of claim 1, wherein the residue of a therapeutic agent is a residue of a chemotherapeutic agent, an antibiotic agent, an antifungal agent, an antiparasitic agent or an antiviral agent or a prodrug thereof.

11. The therapeutic magnetic nanoparticle of claim 1, wherein the residue of a therapeutic agent is a residue of Cladribine, Azacitidine, Abraxane, Adcetris, Doxorubicin, Afinitor, Vinblastine, Amifostine, Amifostine, Arabinosylcytosine, Cytarabine, Pamidronic Acid, Nelarabine, Bicalutamide, Blemycin, Bortezomib, Cabazitaxel, Irinotecan, Camptothecin, Capecitabine, Temsirolimus, Daunorubicin, Cortisone, Decitabine, Dasatinib, Dexamethasone, Prednisolone, Dexamethasone Acetate, Mitoxantrone, Docetaxel, Hydroxycarbamide, Methylprednisolone, Epirubicin, Curcumin, Estramustine, Eribulin, Etoposide, Everolimus, Raloxifene, Fulvestrant, Floxuridine, Fludarabine, Fluoxymesterone, Gemcitabine, Goserelin, Topotecan, Hydrocortisone, Hydrocortone Phosphate, Idarubicin, Ixabepilone, Vincristine, Leuprolide (Leuprorelin), Megestrol, Vinorelbine, Nelarabine, Pentostatin, Octreotide, Paclitaxel, Streptozotocin, Teniposide, Valrubicin, Vorinostat, Zoledronic Acid, Cladribine, Azacitidine, Mecaptopurine, Tioguanine, Actinomycin D, Doxorubicin, Anagrelide, Pemetrexed, Vinblastine, Melphalan, Methotrexate, Amifostine, Aminoglutethimide, Arabinosylcytosine, Cytarabine, Pamidronic Acid, Nelarabine, Axitinib, Bleomycin, Bosutinib, Folinic Acid, Leucovorin, Vandetanib, Lenalidomide, Daunorubicin, Crizotinib, Dacarbazine, Decitabine, Dasatinib, Mitoxantrone, Eribulin, Erlotinib, Fludarabine, Pralatrexate, Gefitinib, Gemcitabine, Imatinib, Goserelin, Idarubicin, Lapatinib, Vincristine, Leuprolide, Procarbazine, Methotrexate, Mitomycin, Vinorebine, Nelarabine, Nilotinib, Pentostatin, Octreotide, Pazopanib, Sunitinib, Abraxane, Actinomycin D, Doxorubicin, Afinitor, Exemestane, Carfilzomib, Daunorubicin, Cortisone, Prednisolone, Prednisone, Dexamethasone Acetate, Docetaxel, Methylprednisolone, Epirubicin, Curcumin, Everolimus, Fluoxymesterone, Hydrocortisone, Hydrocortone Phosphate, Idarubicin, Ixabepilone, Vincristine, Megestrol, Valrubicin, Mesna, 13-cis-Retinoic Acid, Isotretinoin, Alitretinoin, Melphalan, Tretinoin, Methotrexate, Anastrozole, Bendamustine, Bexarotene, Carmustine, Lomustine, Chlorambucil and Ibritumomab Tiuxetan.

12. A pharmaceutical composition comprising a therapeutic magnetic nanoparticle as described in claim 1, or a pharmaceutically acceptable salt thereof and a pharmaceutically acceptable carrier.

13. The therapeutic magnetic nanoparticle of claim 1, wherein $L^1$ is —$(CH_2)_2$—, —$(CH_2)_3$—, or —$(CH_2)_4$—.

14. The therapeutic magnetic nanoparticle of claim 1, wherein W is NH, X is $CR^cR^d$ and n is an integer from 0-5.

15. The therapeutic magnetic nanoparticle of claim 1, wherein W is —NH—, X is O, and n is an integer from 1-5.

16. The therapeutic magnetic nanoparticle of claim 1, wherein each J is $C(R^b)_2$.

17. The therapeutic magnetic nanoparticle of claim 1, wherein $J_n$ is —$(CH_2)_2$—, —$(CH_2)_3$—, —$(CH_2)_4$— or —$CH_2CH_2C(Me)_2CH_2$—.

18. A method for preparing a therapeutic magnetic nanoparticle, or a salt thereof of claim 1 comprising contacting a compound of formula II:

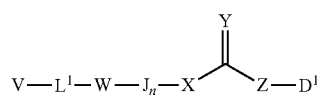

with a magnetic nanoparticle to prepare the therapeutic nanoparticle;

wherein:

V is —SH;

$L^1$ is $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene, wherein $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene is optionally substituted with one or more halogen;

each J is $C(R^b)_2$ wherein one $C(R^b)_2$ of J may be replaced by —O— —S— or —N($R^e$)—;

(a) W is NH, X is $CR^cR^d$, and n is an integer from 0-5; or (b) W is NH, X is O, $NR^e$ or S, and n is an integer from 1-5; or (c) W is

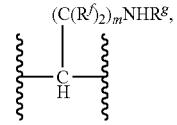

X is $CR^cR^d$, O, $NR^e$, S or absent, m is an integer from 0-5 and n is an integer from 0-5, wherein the sum of m and n is 0-5;

Y is O or S;

$Z-D^1$ is a residue of a therapeutic agent wherein Z is O, $NR^h$ or S;

each $R^b$ is independently selected from H and $(C_1-C_3)$alkyl; or two $R^b$ groups together with the carbon to which they are attached form a $(C_3-C_7)$carbocycle;

each $R^c$ is independently selected from H and $(C_1-C_6)$alkyl, and each $R^d$ is independently selected from H and $(C_1-C_6)$alkyl; or an $R^c$ group and an $R^d$ group together with the carbon to which they are attached form a $(C_3-C_7)$carbocycle;

each $R^e$ is independently selected from H and $(C_1-C_6)$alkyl;

each $R^f$ is independently selected from H and $(C_1-C_6)$alkyl; or two $R_f$ groups together with the carbon to which they are attached form a $(C_3-C_7)$carbocycle;

$R^g$ is selected from H and $(C_1-C_6)$alkyl; and $R^h$ is selected from H and $(C_1-C_6)$alkyl.

19. A method for administering a therapeutic agent to an animal comprising administering the therapeutic magnetic nanoparticle as described in claim 1, or a pharmaceutically acceptable salt thereof, to the animal.

20. A method for treating cancer, a bacterial infection, a fungal infection, a parasitic infection or an antiviral infection in an animal in need thereof comprising administering an effective amount of a therapeutic magnetic nanoparticle as described in claim 10, or a pharmaceutically acceptable salt thereof.

21. The method according to claim 20, further comprising delivering a source of heat to the therapeutic magnetic nanoparticle.

22. The method according to claim 20, further comprising applying an alternating electromagnetic field to the therapeutic magnetic nanoparticle.

23. A therapeutic magnetic nanoparticle, or a salt thereof, comprising a magnetic nanoparticle covalently bonded to one or more -L-D groups wherein D is a residue of a therapeutic agent and L is a linker capable of undergoing an intramolecular cyclization;

wherein -L-D has the following formula Ib:

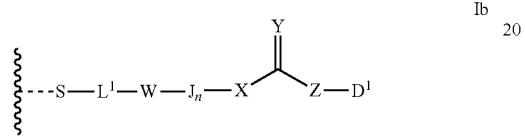

Ib wherein the dashed bond represents a covalent bond to the magnetic nanoparticle and wherein;

$L^1$ is $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene, wherein $(C_1-C_6)$alkylene, $(C_1-C_6)$heteroalkylene, $(C_2-C_6)$alkenylene, $(C_2-C_6)$alkynylene, phenylene or $(C_3-C_7)$carbocyclene are optionally substituted with one or more halogen;

each J is $C(R^b)_2$ wherein one $C(R^b)_2$ of J may be replaced by —O—, —S— or —N($R^e$)—;

(a) W is NH, X is $CR^cR^d$, and n is an integer from 0-5; or
(b) W is NH, X is O, $NR^e$ or S, and n is an integer from 1-5; or
(c) W is

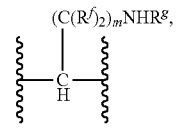

X is $CR^cR^d$, O, $NR^e$, S or absent, m is an integer from 0-5 and n is an integer from 0-5, wherein the sum of m and n is 0-5;

Y is O or S;

$Z-D^1$ is a residue of a therapeutic agent wherein Z is O, $NR^h$ or S;

each $R^b$ is independently selected from H and $(C_1-C_3)$alkyl; or two $R^b$ groups together with the carbon to which they are attached form a $(C_3-C_7)$carbocycle;

each $R^c$ is independently selected from H and $(C_1-C_6)$alkyl, and each $R^d$ is independently selected from H and $(C_1-C_6)$alkyl; or an $R^c$ group and an $R^d$ group together with the carbon to which they are attached form a $(C_3-C_7)$carbocycle;

each $R^e$ is independently selected from H and $(C_1-C_6)$alkyl;

each $R^f$ is independently selected from H and $(C_1-C_6)$alkyl; or two $R_f$ groups together with the carbon to which they are attached form a $(C_3-C_7)$carbocycle;

$R^g$ is selected from H and $(C_1-C_6)$alkyl; and
$R^h$ is selected from H and $(C_1-C_6)$alkyl.

* * * * *